US010759830B2

(12) United States Patent
Vassylyev et al.

(10) Patent No.: US 10,759,830 B2
(45) Date of Patent: Sep. 1, 2020

(54) BACTERIAL COLICIN-IMMUNITY PROTEIN PROTEIN PURIFICATION SYSTEM

(71) Applicant: THE UAB RESEARCH FOUNDATION, Birmingham, AL (US)

(72) Inventors: Dmitry Vassylyev, Vestavia Hills, AL (US); Norman Patrick Higgins, Birmingham, AL (US); Marina Vassylyeva, Vestavia Hills, AL (US); Alexey Vasiliev, Vestavia Hills, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 0 days.

(21) Appl. No.: 16/060,753

(22) PCT Filed: Dec. 9, 2016

(86) PCT No.: PCT/US2016/065843
§ 371 (c)(1),
(2) Date: Jun. 8, 2018

(87) PCT Pub. No.: WO2017/100584
PCT Pub. Date: Jun. 15, 2017

(65) Prior Publication Data

US 2018/0371010 A1 Dec. 27, 2018

Related U.S. Application Data

(60) Provisional application No. 62/265,253, filed on Dec. 9, 2015.

(51) Int. Cl.

| | |
|---|---|
| ***C12N 15/62*** | (2006.01) |
| ***C07K 1/22*** | (2006.01) |
| ***C07K 14/245*** | (2006.01) |
| ***C12P 21/02*** | (2006.01) |
| ***C12N 9/22*** | (2006.01) |
| ***C12P 21/06*** | (2006.01) |

(52) U.S. Cl.
CPC .............. *C07K 1/22* (2013.01); *C07K 14/245* (2013.01); *C12N 9/22* (2013.01); *C12N 15/62* (2013.01); *C12P 21/02* (2013.01); *C12P 21/06* (2013.01); *C07K 2319/00* (2013.01); *C07K 2319/21* (2013.01); *C07K 2319/23* (2013.01); *C07K 2319/24* (2013.01); *C07K 2319/50* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 2006/0147371 | A1 | 7/2006 | Tuszynski et al. |
| 2009/0233343 | A1 | 9/2009 | Kleanthous et al. |
| 2013/0337454 | A1 | 12/2013 | Duchateau et al. |
| 2015/0164984 | A1 | 6/2015 | Walker et al. |

FOREIGN PATENT DOCUMENTS

| | | | |
|---|---|---|---|
| DE | 102015108849 | A1 | 12/2016 |
| WO | 2006097708 | A2 | 9/2006 |

OTHER PUBLICATIONS

Juraja et al., Engineering of the *Escherichia coli* Im7 immunity protein as a loop display scaffold, Protein Engineering, Design and Selection, vol. 19 pp. 231-244 (Year: 2006).*
Nemeth et al., Fine tuning of the catalytic activity of colicin E7 nuclease domain by systematic N-terminal mutations, The Protein Society, Cvol. 23:1113-1122 (Year: 2014).*
Banerjee et al., Optimization of Recombinant *Mycobacterium tuberculosis* RNA Polymerase Expression and Purification, Tuberculosis, vol. 94, No. 4, Jul. 2014, pp. 1-8.
Cramer et al., Structural Basis of Transcription: RNA Polymerase II at 2.8 Angstrom Resolution, Science, vol. 292, No. 5523, Jun. 8, 2001, pp. 1863-1876.
Datta et al., A Set of Recombineering Plasmids for Gram-Negative Bacteria, Gene, vol. 379, Sep. 1, 2006, pp. 109-115.
European Patent Application No. 16873923.3, Partial Supplementary European Search Report dated Jun. 19, 2019, 16 pages.
European Patent Application No. 16873923.3, Extended European Search Report dated Oct. 14, 2019, 17 pages.
Fong et al., The Potential Role of Self-Cleaving Purification Tags in Commercial-Scale Processes, Trends in Biotechnology, vol. 28, No. 5, May 2010, pp. 272-279.
Garinot-Schneider et al., Identification of Putative Active-Site Residues in the DNase Domain of Colicin E9 by Random Mutagenesis, Journal of Molecular Biology, vol. 260, No. 5, Aug. 1, 1996, pp. 731-742.
Graslund et al., Protein Production and Purification, Nature Methods, vol. 5, No. 2, Feb. 2008, pp. 135-146.
Hosse et al., Kinetic Screening of Antibody-Im7 Conjugates by Capture on a Colicin E7 DNase Domain Using Optical Biosensors, Analytical Biochemistry, vol. 385, No. 2, Feb. 15, 2009, pp. 346-357.
Hunegnaw et al., Interaction Between HIV-1 Nef and Calnexin: From Modeling to Small Molecule Inhibitors Reversing HIV-Induced Lipid Accumulation, Arteriosclerosis Thrombosis and Vascular Biology, vol. 36, No. 9, Sep. 2016, pp. 1758-1771.
Kashkina et al., Elongation Complexes of Thermus Thermophilus RNA Polymerase that Possess Distinct Translocation Conformations, Nucleic Acids Research, vol. 34, No. 14, Sep. 1, 2006, pp. 4036-4045.

(Continued)

*Primary Examiner* — Mindy G Brown
(74) *Attorney, Agent, or Firm* — Kilpatrick Townsend & Stockton LLP

(57) ABSTRACT

The disclosure provides compositions and methods for purification of proteins, including multi-subunit complexes and membrane proteins. Modified colicin-DNAse domains and modified colicin immunity proteins are provided for use in purification methods. Also provided are related nucleic acids, vectors, genetically modified cells and affinity matrices.

11 Claims, 19 Drawing Sheets

Specification includes a Sequence Listing.

(56) References Cited

OTHER PUBLICATIONS

Kimple et al., Overview of Affinity Tags for Protein Purification, Current Protocols in Protein Science, vol. 73, No. 1, Unit 9.9, Aug. 2013, pp. 9.9.1-9.9.23. Knecht et al., Oligohis-Tags: Mechanisms of Binding to Ni2+-NTA Surfaces, Journal of Molecular Recognition, vol. 22, No. 4, Jul.-Aug. 2009, pp. 270-279.
Ko et al., The Crystal Structure of the DNase Domain of Colicin E7 in Complex with Its Inhibitor Im7 Protein, Structure, vol. 7, No. 1, Jan. 1999, pp. 91-102.
Kumazaki et al., Crystallization and Preliminary X-Ray Diffraction Analysis of YidC, a Membrane-Protein Chaperone and Insertase From Bacillus Halodurans, Acta Crystallographica Section F, Structural Biology Communications, vol. 70, No. 8, Aug. 2014, pp. 1056-1060.
Kumazaki et al., Structural Basis of Sec-Independent Membrane Protein Insertion by YidC, Nature, vol. 509, No. 501, May 22, 2014, pp. 516-520.
Kuznedelov et al., Recombinant Thermus Aquaticus RNA Polymerase for Structural Studies, Journal of Molecular Biology, vol. 359, No. 1, May 26, 2006, pp. 110-121.
Lichty et al., Comparison of Affinity Tags for Protein Purification, Protein Expression and Purification, vol. 41, No. 1, May 2005, pp. 98-105.
Loyola et al., Functional Analysis of the Subunits of the Chromatin Assembly Factor RSF, Molecular and Cellular Biology, vol. 23, No. 19, Oct. 2003, pp. 6759-6768.
Manjeet et al., Bacterial Chitin Binding Proteins Show Differential Substrate Binding and Synergy with Chitinases, Microbiological Research, vol. 168, No. 7, Aug. 25, 2013, pp. 461-468.
Miller et al., Rates of Ligand Binding to Periplasmic Proteins Involved in Bacterial Transport and Chemotaxis, Journal of Biological Chemistry, vol. 258, No. 22, Nov. 25, 1983, pp. 13665-13672.
Nemeth et al., Substrate Binding Activates the Designed Triple Mutant of the Colicin E7 Metallonuclease, Journal of Biological Inorganic Chemistry, vol. 19, No. 8, Aug. 26, 2014, pp. 1295-1303.
Neyer et al., Structure of RNA Polymerase I Transcribing Ribosomal DNA Genes, Nature, vol. 540, Nov. 14, 2016, pp. 1-17.
Ohana et al., HaloTag-based Purification of Functional Human Kinases from Mammalian Cells, Protein Expression and Purification, vol. 76, No. 2, Apr. 2011, pp. 154-164.
Ou et al., Conformational Changes Induced in the Endoplasmic Reticulum Luminal Domain of Calnexin by Mg-ATP and Ca2+, Journal of Biological Chemistry, vol. 270, No. 30, Jul. 28, 1995, pp. 18051-18059.
Pandey et al., Current Strategies for Protein Production and Purification Enabling Membrane Protein Structural Biology, Biochemistry and Cell Biology, vol. 94, No. 6, Dec. 2016, pp. 507-527.
International Application No. PCT/US2016/065843, International Preliminary Report on Patentability dated Jun. 21, 2018, 9 pages.
International Application No. PCT/US2016/065843, International Search Report and Written Opinion dated May 5, 2017, 14 pages.
International Application No. PCT/US2016/065843, Invitation to Pay Additional Fees and, Where Applicable, Protest Fee dated Feb. 27, 2017, 2 pages.
Petrushenko et al., Antagonistic Interactions of Kleisins and DNA with Bacterial Condensin MukB, Journal of Biological Chemistry, vol. 281, No. 45, Nov. 10, 2006, pp. 34208-34217.
Resh, Covalent Lipid Modifications of Proteins, Current Biology, vol. 23, No. 10, May 20, 2013, pp. R431-R435.
Saha et al., Comparative Study of IgG Binding to Proteins G and A: Nonequilibrium Kinetic and Binding Constant Determination with the Acoustic Waveguide Device, Analytical Chemistry, vol. 75, No. 4, Feb. 15, 2003, pp. 835-842.
Schmidt et al., The Strep-Tag System for One-step Purification and High-Affinity Detection or Capturing of Proteins, Nature Protocols, vol. 2, No. 6, 2007, pp. 1528-1535.
Schrag et al., The Structure of Calnexin, an ER Chaperone Involved in Quality Control of Protein Folding, Molecular Cell, vol. 8, No. 3, Sep. 2001, pp. 633-644.
She et al., MukEF Is Required for Stable Association of MukB with the Chromosome, Journal of Bacteriology, vol. 189, No. 19, Oct. 2007, pp. 7062-7068.
Singh et al., Exploring the Potential of Genome Editing CRISPR-Cas9 Technology, Gene, vol. 599, Jan. 30, 2017, pp. 1-8.
Svetlov et al., Purification of Bacterial RNA Polymerase: Tools and Protocols, Methods in Molecular Biology, vol. 1276, Jul. 1, 2015, pp. 13-29.
Tessema et al., Glutathione-S-Transferase-Green Fluorescent Protein Fusion Protein Reveals Slow Dissociation from High Site Density Beads and Measures Free GSH, Cytometry Part A, vol. 69, No. 5, May 2006, pp. 326-334.
Thompson et al., Identification, Production, and Use of Polyol-Responsive Monoclonal Antibodies for Immunoaffinity Chromatography, Methods in Enzymology, vol. 463, 2009, pp. 475-494.
Vassylyev et al., Crystal Structure of a Bacterial RNA Polymerase Holoenzyme at 2.6 A Resolution, Nature, vol. 417, No. 6890, Jun. 13, 2002, pp. 712-719.
Vassylyev, Elongation by RNA Polymerase: A Race Through Roadblocks, Current Opinion in Structural Biology, vol. 19, No. 6, Dec. 2009, pp. 691-700.
Vassylyev et al., Structural Basis for Substrate Loading in Bacterial RNA Polymerase, Nature, vol. 448, No. 7150, Jul. 12, 2007, pp. 163-168.
Vassylyev et al., Structural Basis for Transcription Elongation by Bacterial RNA Polymerase, Nature, vol. 448, No. 7150, Jul. 12, 2007, pp. 157-162.
Vassylyeva et al., Efficient, Ultra-High-Affinity Chromatography in a One-step Purification of Complex Proteins, Proceedings of the National Academy of Sciences of the United States of America, vol. 114, No. 26, Jun. 12, 2017, pp. E5138-E5147.
Vassylyeva et al., Purification, Crystallization and Initial Crystallographic Analysis of RNA Polymerase Holoenzyme from Thermus Thermophilus, Acta Crystallographica Section D, Biological, vol. 58, No. 9, Sep. 2002, pp. 1497-1500.
Wallis et al., Protein-Protein Interactions in Colicin E9 DNase-immunity Protein Complexes. 1. Diffusion-Controlled Association and Femtomolar Binding for the Cognate Complex, Biochemistry, vol. 34, No. 42, Oct. 24, 1995, pp. 13743-13750.
Wallis et al., Protein-Protein Interactions in Colicin E9 DNase-Immunity Protein Complexes. 2. Cognate and Noncognate Interactions That Span the Millimolar to Femtomolar Affinity Range, Biochemistry, vol. 34, No. 42, Oct. 24, 1995, pp. 13751-13759.
Wang et al., Structural Basis for Sequence-Dependent DNA Cleavage by Nonspecific Endonucleases, Nucleic Acids Research, vol. 35, No. 2, Jan. 2007, pp. 584-594.
Wegner et al., Characterization and Optimization of Peptide Arrays for the Study of Epitope-Antibody Interactions Using Surface Plasmon Resonance Imaging, Analytical Chemistry, vol. 74, No. 20, Oct. 2002, pp. 5161-5168.
Woo et al., Structural Studies of a Bacterial Condensin Complex Reveal ATP-Dependent Disruption of Intersubunit Interactions, Cell, vol. 136, No. 1, Jan. 9, 2009, pp. 85-96.

* cited by examiner

A ttRNAP Purification

Purification: (~2 hrs)
(LG Gravity; ~300mg/20ml)

| WCL Cells (g) | FT Loss (%) | Eluant PSC (mg) | EL Amount (mg) |
|---|---|---|---|
| 3 | N/A | 0.5 | 37 |

B mtRNAP Purification

Purification: (~2 hrs)
(LG Gravity; ~300mg/20ml)

| WCL Cells (g) | FT Loss (%) | Eluant PSC (mg) | EL Amount (mg) |
|---|---|---|---|
| 3 | ~20 | 2 | 29 |

FIGURE 4 (cont.)

Multi-Subunit Cytoplasmic Proteins

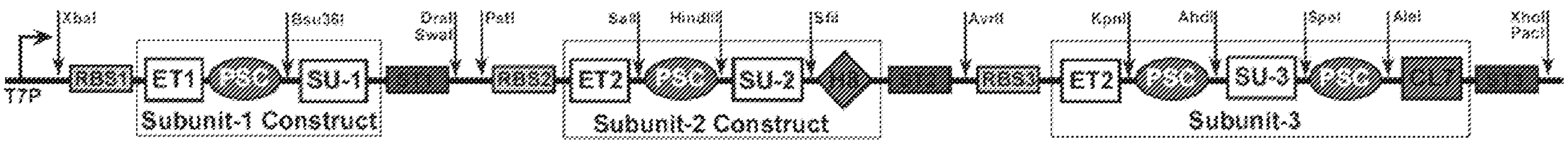

T7P - T7 promoter; RBS - ribosome binding site; Yidc-SP - modified Signal Peptide of Yidc protein;

Trx - thioredoxin, serves as expression enhancing tag; ET - developed expression enhancing tags;

SU-P/PSC - SUMO-P/PSC protease cleavage sites; H8/CL7 - His8 and CL7 affinity tags;

SU - subunits of the target multi-subunit system; [stop codon box] - stop codons; ——► - cloning restriction sites

FIGURE 6 a Comparison of available chromatography systems

| Chromatography System | | | Affinity $K_D$ (M) | Loading Buffer NaCl (M) | Capacity (mg/ml) | PP ($/mg) | Company |
|---|---|---|---|---|---|---|---|
| Name | Tag | Column Ligand | | | | | |
| Strep-Tag | Pept | Prot | $10^{-6}$ | < 0.2 | 6 | 10/12 | Qiagen/GE |
| FLAG-Tag | Pept | Prot | $10^{-9}$ | < 0.2 | 0.6 | 200/760 | Genscript/ Sigma |
| CalBD | Pept | Prot | $10^{-9}$ | < 0.3 | 0.5-1.5 | 220 | Sigma |
| Halo-Tag | Prot | SM | Covalent | < 0.2 | 7 | 10 (disposable) | Promega |
| MBP | Prot | SM | $10^{-6}$ | < 0.2 | 6-10 | 8-10 | GE |
| GST | Prot | SM | $10^{-6}$ | < 0.2 | 10 | 2 | GE |
| ChBD | Prot | SM | $10^{-6}$ | < 0.5 | 2 | 2 | NEB |
| His-Tag | Pept | $Ni^{2+}$ | $10^{-9}$ | 1+ | 15-40 | 0.8-1.5 | GE/Sigma |
| CL7/Im7 | Prot | Prot | $10^{-14}$-$10^{-17}$ | 1+ | ~14-20 | ~0.9-1.3 | Lab Prep |

a

```
CL7:   1 KRNKPGKATG KGKPVNNKWL NNAGKDLGSP VPDRIANKLR DKEFKSFDDF RKKFWEEVSK  60
CL7:  61 DPELSKQFSR NNNDRMKVGK APKTRTQDVS GKRTSFEL[illegible]H EKPISQNGGV YDMDNISVVT 120
CL7: 121 PKR[illegible]IDI[illegible]
```

b

Published Dual-plasmid Expression

| WCL Cells (g) | FT Loss (%) | Eluant PSC (mg) | EL Amount (mg) |
|---|---|---|---|
| 3 | ~30 | 0.5 | 29 |

| WCL Cells (g) | FT Loss (%) | Eluant PSC (mg) | EL Amount (mg) |
|---|---|---|---|
| 6 | ~30 | 0.5 | 20 |

SEQUENCE LISTING

```
<160> NUMBER OF SEQ ID NOS: 23

<210> SEQ ID NO 1
<211> LENGTH: 128
<212> TYPE: PRT
<213> ORGANISM: Artificial sequence
<220> FEATURE:
<223> OTHER INFORMATION: Synthetic construct

<400> SEQUENCE: 1

Lys Arg Asn Lys Pro Gly Lys Ala Thr Gly Lys Gly Lys Pro Val Asn
1               5                   10                  15

Asn Lys Trp Leu Asn Asn Ala Gly Lys Asp Leu Gly Ser Pro Val Pro
            20                  25                  30

Asp Arg Ile Ala Asn Lys Leu Arg Asp Lys Glu Phe Lys Ser Phe Asp
        35                  40                  45

Asp Phe Arg Lys Lys Phe Trp Glu Glu Val Ser Lys Asp Pro Glu Leu
    50                  55                  60

Ser Lys Gln Phe Ser Arg Asn Asn Asn Asp Arg Met Lys Val Gly Lys
65                  70                  75                  80

Ala Pro Lys Thr Arg Thr Gln Asp Val Ser Gly Lys Arg Thr Ser Phe
                85                  90                  95

Glu Leu His His Glu Lys Pro Ile Ser Gln Asn Gly Gly Val Tyr Asp
            100                 105                 110

Met Asp Asn Ile Ser Val Val Thr Pro Lys Arg His Ile Asp Ile His
        115                 120                 125


<210> SEQ ID NO 2
<211> LENGTH: 128
<212> TYPE: PRT
<213> ORGANISM: Artificial sequence
<220> FEATURE:
<223> OTHER INFORMATION: Synthetic construct

<400> SEQUENCE: 2

Lys Arg Asn Lys Pro Gly Lys Ala Thr Gly Lys Gly Lys Pro Val Gly
1               5                   10                  15

Asp Lys Trp Leu Asp Asp Ala Gly Lys Asp Ser Gly Ala Pro Ile Pro
            20                  25                  30

Asp Arg Ile Ala Asp Lys Leu Arg Asp Lys Glu Phe Lys Asn Phe Asp
        35                  40                  45

Asp Phe Arg Lys Lys Phe Trp Glu Glu Val Ser Lys Asp Pro Asp Leu
```

```
    50                  55                  60

Ser Lys Gln Phe Lys Gly Ser Asn Lys Thr Asn Ile Gln Lys Gly Lys
65                  70                  75                  80

Ala Pro Phe Ala Arg Lys Lys Asp Gln Val Gly Gly Arg Glu Arg Phe
                85                  90                  95

Glu Leu His His Asp Lys Pro Ile Ser Gln Asp Gly Gly Val Tyr Asp
            100                 105                 110

Met Asn Asn Ile Arg Val Thr Thr Pro Lys Arg His Ile Asp Ile His
        115                 120                 125


<210> SEQ ID NO 3
<211> LENGTH: 128
<212> TYPE: PRT
<213> ORGANISM: Artificial sequence
<220> FEATURE:
<223> OTHER INFORMATION: Synthetic construct

<400> SEQUENCE: 3

Lys Arg Asn Lys Pro Gly Lys Ala Thr Gly Lys Gly Lys Pro Val Gly
1               5                   10                  15

Asp Lys Trp Leu Asp Asp Ala Gly Lys Asp Ser Gly Ala Pro Ile Pro
            20                  25                  30

Asp Arg Ile Ala Asp Lys Leu Arg Asp Lys Glu Phe Lys Asn Phe Asp
        35                  40                  45

Asp Phe Arg Arg Lys Phe Trp Glu Glu Val Ser Lys Asp Pro Glu Leu
    50                  55                  60

Ser Lys Gln Phe Asn Pro Gly Asn Lys Lys Arg Leu Ser Gln Gly Leu
65                  70                  75                  80

Ala Pro Arg Ala Arg Asn Lys Asp Thr Val Gly Gly Arg Arg Ser Phe
                85                  90                  95

Glu Leu His His Asp Lys Pro Ile Ser Gln Asp Gly Gly Val Tyr Asp
            100                 105                 110

Met Asp Asn Leu Arg Ile Thr Thr Pro Lys Arg His Ile Asp Ile His
        115                 120                 125


<210> SEQ ID NO 4
<211> LENGTH: 128
<212> TYPE: PRT
<213> ORGANISM: Artificial sequence
<220> FEATURE:
<223> OTHER INFORMATION: Synthetic construct

<400> SEQUENCE: 4

Lys Arg Asn Lys Pro Gly Lys Ala Thr Gly Lys Gly Lys Pro Val Gly
1               5                   10                  15

Asp Lys Trp Leu Asp Asp Ala Gly Lys Asp Ser Gly Ala Pro Ile Pro
            20                  25                  30

Asp Arg Ile Ala Asp Lys Leu Arg Asp Lys Glu Phe Lys Ser Phe Asp
        35                  40                  45

Asp Phe Arg Lys Ala Val Trp Glu Glu Val Ser Lys Asp Pro Glu Leu
    50                  55                  60

Ser Lys Asn Leu Asn Pro Ser Asn Lys Ser Ser Val Ser Lys Gly Tyr
65                  70                  75                  80

Ser Pro Phe Thr Pro Lys Asn Gln Gln Val Gly Gly Arg Lys Val Tyr
                85                  90                  95

Glu Leu His His Asp Lys Pro Ile Ser Gln Gly Gly Glu Val Tyr Asp
            100                 105                 110
```

Met Asp Asn Ile Arg Val Thr Thr Pro Lys Arg His Ile Asp Ile His
115 120 125

<210> SEQ ID NO 5
<211> LENGTH: 72
<212> TYPE: PRT
<213> ORGANISM: Artificial sequence
<220> FEATURE:
<223> OTHER INFORMATION: Synthetic construct

<400> SEQUENCE: 5

Gly Gly Thr Ser Asp Gly Leu Glu Val Leu Phe Gln Gly Pro Asn Gly
1 5 10 15

Glu Asp Asn Gln Ser Asn His His His His His His His His Asn Gln
20 25 30

Ala Glu Asn Ser Ala Ala Asn Asn Ala Ser Asp Asp Gly Asn Gln Ser
35 40 45

Ser Asn Glu Ser Ser Ser Asp Gly Glu Gln Ala Asn Thr Asp Ser Ala
50 55 60

His Glu Gly Gly Thr Ala Gly Ser
65 70

<210> SEQ ID NO 6
<211> LENGTH: 201
<212> TYPE: PRT
<213> ORGANISM: Artificial sequence
<220> FEATURE:
<223> OTHER INFORMATION: Synthetic construct

<400> SEQUENCE: 6

Gly Gly Thr Ser Asp Gly Leu Glu Val Leu Phe Gln Gly Pro Asn Gly
1 5 10 15

Glu Asp Asn Gln Ser Asn His His His His His His His His Asn Gln
20 25 30

Ala Glu Asn Ser Ala Ala Asn Asn Ala Ser Asp Asp Gly Asn Gln Ser
35 40 45

Ser Asn Glu Ser Ser Ser Asp Gly Glu Gln Ala Asn Thr Asp Ser Ala
50 55 60

His Glu Gly Gly Thr Ala Gly Ser Lys Ser Asn Glu Pro Gly Lys Ala
65 70 75 80

Thr Gly Glu Gly Lys Pro Val Asn Asn Lys Trp Leu Asn Asn Ala Gly
85 90 95

Lys Asp Leu Gly Ser Pro Val Pro Asp Arg Ile Ala Asn Lys Leu Arg
100 105 110

Asp Lys Glu Phe Glu Ser Phe Asp Asp Phe Arg Glu Thr Phe Trp Glu
115 120 125

Glu Val Ser Lys Asp Pro Glu Leu Ser Lys Gln Phe Ser Arg Asn Asn
130 135 140

Asn Asp Arg Met Lys Val Gly Lys Ala Pro Lys Thr Arg Thr Gln Asp
145 150 155 160

Val Ser Gly Lys Arg Thr Ser Phe Glu Leu Asn His Gln Lys Pro Ile
165 170 175

Glu Gln Asn Gly Gly Val Tyr Asp Met Asp Asn Ile Ser Val Val Thr
180 185 190

Pro Lys Arg Asn Ile Asp Ile Glu Gly
195 200

<210> SEQ ID NO 7

-continued

```
<211> LENGTH: 199
<212> TYPE: PRT
<213> ORGANISM: Artificial sequence
<220> FEATURE:
<223> OTHER INFORMATION: Synthetic construct

<400> SEQUENCE: 7

Gly Gly Thr Ser Asp Gly Leu Glu Val Leu Phe Gln Gly Pro Asn Gly
1               5                   10                  15

Glu Asp Asn Gln Ser Asn His His His His His His His His Asn Gln
            20                  25                  30

Ala Glu Asn Ser Ala Ala Asn Asn Ala Ser Asp Asp Gly Asn Gln Ser
        35                  40                  45

Ser Asn Glu Ser Ser Ser Asp Gly Glu Gln Ala Asn Thr Asp Ser Ala
    50                  55                  60

His Glu Gly Gly Thr Ala Gly Ser Lys Ser Asn Glu Pro Gly Lys Ala
65                  70                  75                  80

Thr Gly Glu Gly Lys Pro Val Gly Asp Lys Trp Leu Asp Asp Ala Gly
                85                  90                  95

Lys Asp Ser Gly Ala Pro Ile Pro Asp Arg Ile Ala Asp Lys Leu Arg
            100                 105                 110

Asp Lys Glu Phe Glu Asn Phe Asp Asp Phe Arg Glu Thr Phe Trp Glu
        115                 120                 125

Glu Val Ser Asp Pro Asp Leu Ser Lys Gln Phe Lys Gly Ser Asn Lys
    130                 135                 140

Thr Asn Ile Gln Lys Gly Lys Ala Pro Phe Ala Arg Lys Lys Asp Gln
145                 150                 155                 160

Val Gly Gly Arg Glu Arg Phe Glu Leu Asn His Asp Lys Pro Ile Glu
                165                 170                 175

Gln Asp Gly Gly Val Tyr Asp Met Asn Asn Ile Arg Val Thr Thr Pro
            180                 185                 190

Lys Arg Asn Ile Asp Ile Asn
        195


<210> SEQ ID NO 8
<211> LENGTH: 200
<212> TYPE: PRT
<213> ORGANISM: Artificial sequence
<220> FEATURE:
<223> OTHER INFORMATION: Synthetic construct

<400> SEQUENCE: 8

Gly Gly Thr Ser Asp Gly Leu Glu Val Leu Phe Gln Gly Pro Asn Gly
1               5                   10                  15

Glu Asp Asn Gln Ser Asn His His His His His His His His Asn Gln
            20                  25                  30

Ala Glu Asn Ser Ala Ala Asn Asn Ala Ser Asp Asp Gly Asn Gln Ser
        35                  40                  45

Ser Asn Glu Ser Ser Ser Asp Gly Glu Gln Ala Asn Thr Asp Ser Ala
    50                  55                  60

His Glu Gly Gly Thr Ala Gly Ser Lys Ser Asn Glu Pro Gly Lys Ala
65                  70                  75                  80

Thr Gly Glu Gly Lys Pro Val Gly Asp Lys Trp Leu Asp Asp Ala Gly
                85                  90                  95

Lys Asp Ser Gly Ala Pro Ile Pro Asp Arg Ile Ala Asp Lys Leu Arg
            100                 105                 110

Asp Lys Glu Phe Glu Asn Phe Asp Asp Phe Arg Glu Thr Phe Trp Glu
```

```
        115                 120                 125

Glu Val Ser Lys Asp Pro Glu Leu Ser Lys Gln Phe Asn Pro Gly Asn
    130                 135                 140

Lys Lys Arg Leu Ser Gln Gly Leu Ala Pro Arg Ala Arg Asn Lys Asp
145                 150                 155                 160

Thr Val Gly Gly Arg Arg Ser Phe Glu Leu Asn His Asp Lys Pro Ile
                165                 170                 175

Glu Gln Asp Gly Gly Val Tyr Asp Met Asp Asn Leu Arg Ile Thr Thr
            180                 185                 190

Pro Lys Arg Asn Ile Asp Ile Asn
        195                 200


<210> SEQ ID NO 9
<211> LENGTH: 203
<212> TYPE: PRT
<213> ORGANISM: Artificial sequence
<220> FEATURE:
<223> OTHER INFORMATION: Synthetic construct

<400> SEQUENCE: 9

Gly Gly Thr Ser Asp Gly Leu Glu Val Leu Phe Gln Gly Pro Asn Gly
1               5                   10                  15

Glu Asp Asn Gln Ser Asn His His His His His His His His Asn Gln
            20                  25                  30

Ala Glu Asn Ser Ala Ala Asn Asn Ala Ser Asp Asp Gly Asn Gln Ser
        35                  40                  45

Ser Asn Glu Ser Ser Ser Asp Gly Glu Gln Ala Asn Thr Asp Ser Ala
    50                  55                  60

His Glu Gly Gly Thr Ala Gly Ser Glu Glu Glu Arg Glu Asn Asn Pro
65                  70                  75                  80

Gly Lys Ala Thr Gly Glu Gly Lys Pro Val Gly Asp Lys Trp Leu Asp
                85                  90                  95

Asp Ala Gly Lys Asp Ser Gly Ala Pro Ile Pro Asp Arg Ile Ala Asp
            100                 105                 110

Lys Leu Arg Asp Lys Glu Phe Glu Ser Phe Asp Asp Phe Arg Glu Ala
        115                 120                 125

Val Trp Glu Glu Val Ser Lys Asp Pro Glu Leu Ser Lys Asn Leu Asn
    130                 135                 140

Pro Ser Asn Lys Ser Ser Val Ser Lys Gly Tyr Ser Pro Phe Thr Pro
145                 150                 155                 160

Lys Asn Gln Gln Val Gly Gly Arg Lys Val Tyr Glu Leu Asn His Asp
                165                 170                 175

Gln Pro Met Trp Gln Gly Gly Glu Val Tyr Asp Met Asp Asn Ile Arg
            180                 185                 190

Val Thr Thr Pro Arg Arg Asn Ile Glu Ile Gly
        195                 200


<210> SEQ ID NO 10
<211> LENGTH: 87
<212> TYPE: PRT
<213> ORGANISM: Artificial sequence
<220> FEATURE:
<223> OTHER INFORMATION: Synthetic construct

<400> SEQUENCE: 10

Met Glu Leu Lys Asn Ser Ile Ser Asp Tyr Thr Glu Ala Glu Phe Val
1               5                   10                  15
```

-continued

```
Gln Leu Leu Lys Glu Ile Glu Lys Glu Asn Val Ala Ala Thr Asp Asp
            20                  25                  30

Val Leu Asp Val Leu Leu Glu His Phe Val Lys Ile Thr Glu His Pro
        35                  40                  45

Asp Gly Thr Asp Leu Ile Tyr Tyr Pro Ser Asp Asn Arg Asp Asp Ser
    50                  55                  60

Pro Glu Gly Ile Val Lys Glu Ile Lys Glu Trp Arg Ala Ala Asn Gly
65                  70                  75                  80

Lys Pro Gly Phe Lys Gln Gly
                85


<210> SEQ ID NO 11
<211> LENGTH: 85
<212> TYPE: PRT
<213> ORGANISM: Artificial sequence
<220> FEATURE:
<223> OTHER INFORMATION: Synthetic construct

<400> SEQUENCE: 11

Met Glu Leu Lys Ala Ser Ile Ser Asp Tyr Thr Glu Ala Glu Phe Leu
1               5                   10                  15

Gln Leu Val Thr Thr Ile Cys Asn Ala Asp Thr Ser Ser Glu Glu Glu
            20                  25                  30

Leu Val Lys Leu Val Thr His Phe Glu Glu Met Thr Glu His Pro Ser
        35                  40                  45

Gly Ser Asp Leu Ile Tyr Tyr Pro Lys Glu Gly Asp Asp Asp Ser Pro
    50                  55                  60

Ser Gly Ile Val Asn Thr Val Gln Gln Trp Arg Ala Ala Asn Gly Lys
65                  70                  75                  80

Ser Gly Phe Lys Gln
                85


<210> SEQ ID NO 12
<211> LENGTH: 356
<212> TYPE: PRT
<213> ORGANISM: Artificial sequence
<220> FEATURE:
<223> OTHER INFORMATION: Synthetic construct

<400> SEQUENCE: 12

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Asp Thr
            100                 105                 110

Ser Gly Thr Gly Ala Glu Gly Arg Arg Gly Glu Glu Ala Gly Lys His
        115                 120                 125

His His His His His His His Gly Lys Gly Ala Glu Glu Gly Arg Arg
    130                 135                 140
```

Gly Glu Ala Gly Leu Glu Val Leu Phe Gln Gly Pro Gly Gln Ala Ser
145 150 155 160

Gly Thr Thr Met Gly Lys Ile Glu Glu Gly Lys Gln Glu Thr Trp Asn
165 170 175

Asn Gly Asp Lys Gly Tyr Asn Gly Arg Ala Glu Asp Gly Gly Cys Gly
180 185 190

Gly Ala Ile Glu Glu Leu Glu Glu Glu Val Arg Arg His Gln Met Arg
195 200 205

Leu Met Ala Leu Gln Leu Glu Glu Gln Leu Met Gly Gly Cys Gly Asp
210 215 220

Val Gly Asp Met Glu Phe Arg Asn Ser Ile Ser Asp Tyr Thr Glu Glu
225 230 235 240

Glu Phe Val Arg Leu Leu Arg Gly Ile Glu Arg Glu Asn Val Ala Ala
245 250 255

Thr Asp Asp Arg Leu Asp Trp Met Leu Glu His Phe Val Glu Ile Thr
260 265 270

Glu His Pro Asp Gly Thr Asp Leu Ile Tyr Tyr Pro Ser Asp Asn Arg
275 280 285

Asp Asp Ser Pro Glu Gly Ile Val Glu Glu Ile Arg Glu Trp Arg Glu
290 295 300

Ala Asn Gly Arg Pro Gly Phe Lys Gln Gly Gly Ser Thr Asp Gly Gly
305 310 315 320

Asp Val Gly Glu Glu Arg Asn Arg Arg Cys Glu Glu Leu Asn Glu Glu
325 330 335

Ile Glu Glu His Arg Glu Arg Leu Arg Gln Leu Glu Glu Thr Arg Glu
340 345 350

Glu Cys Arg Thr
355

<210> SEQ ID NO 13
<211> LENGTH: 354
<212> TYPE: PRT
<213> ORGANISM: Artificial sequence
<220> FEATURE:
<223> OTHER INFORMATION: Synthetic construct

<400> SEQUENCE: 13

Met Ser Asp Lys Ile Ile His Leu Thr Asp Asp Ser Phe Asp Thr Asp
1 5 10 15

Val Leu Lys Ala Asp Gly Ala Ile Leu Val Asp Phe Trp Ala Glu Trp
20 25 30

Cys Gly Pro Cys Lys Met Ile Ala Pro Ile Leu Asp Glu Ile Ala Asp
35 40 45

Glu Tyr Gln Gly Lys Leu Thr Val Ala Lys Leu Asn Ile Asp Gln Asn
50 55 60

Pro Gly Thr Ala Pro Lys Tyr Gly Ile Arg Gly Ile Pro Thr Leu Leu
65 70 75 80

Leu Phe Lys Asn Gly Glu Val Ala Ala Thr Lys Val Gly Ala Leu Ser
85 90 95

Lys Gly Gln Leu Lys Glu Phe Leu Asp Ala Asn Leu Ala Gly Asp Thr
100 105 110

Ser Gly Thr Gly Ala Glu Gly Arg Arg Gly Glu Glu Ala Gly Lys His
115 120 125

His His His His His His His Gly Lys Gly Ala Glu Glu Gly Arg Arg
130 135 140

-continued

```
Gly Glu Ala Gly Leu Glu Val Leu Phe Gln Gly Pro Gly Gln Ala Ser
145                 150                 155                 160

Gly Thr Thr Met Gly Lys Ile Glu Glu Gly Lys Gln Glu Thr Trp Asn
                165                 170                 175

Asn Gly Asp Lys Gly Tyr Asn Gly Arg Ala Glu Asp Gly Gly Cys Gly
            180                 185                 190

Gly Ala Ile Glu Glu Leu Glu Glu Glu Val Arg Arg His Gln Met Arg
        195                 200                 205

Leu Met Ala Leu Gln Leu Glu Glu Gln Leu Met Gly Gly Cys Gly Asp
    210                 215                 220

Val Gly Asp Met Glu Phe Arg Asp Ser Ile Ser Asp Tyr Thr Glu Glu
225                 230                 235                 240

Glu Phe Leu Arg Leu Val Thr Ser Ile Cys Asn Ala Asp Thr Ser Ser
                245                 250                 255

Glu Glu Glu Leu Val Trp Met Val Thr His Phe Glu Glu Ile Thr Glu
            260                 265                 270

His Pro Ser Gly Ser Asp Leu Ile Tyr Tyr Pro Arg Glu Gly Asp Asp
        275                 280                 285

Asp Ser Pro Ser Gly Ile Val Asn Thr Val Arg Gln Trp Arg Glu Ala
    290                 295                 300

Asn Gly Arg Ser Gly Phe Gln Gln Gly Ser Thr Asp Gly Gly Asp Val
305                 310                 315                 320

Gly Glu Glu Arg Asn Arg Arg Cys Glu Glu Leu Asn Glu Glu Ile Glu
                325                 330                 335

Glu His Arg Glu Arg Leu Arg Gln Leu Glu Glu Thr Arg Glu Glu Cys
            340                 345                 350

Arg Thr
```

<210> SEQ ID NO 14
<211> LENGTH: 6361
<212> TYPE: DNA
<213> ORGANISM: Artificial sequence
<220> FEATURE:
<223> OTHER INFORMATION: Synthetic construct

<400> SEQUENCE: 14

```
acgccgaaac aagcgctcat gagcccgaag tggcgagccc gatcttcccc atcggtgatg     60

tcggcgatat aggcgccagc aaccgcacct gtggcgccgg tgatgccggc cacgatgcgt    120

ccggcgtaga ggatcgagat ctcgatcccg cgaaattaat acgactcact ataggggaat    180

tgtgagcgga taacaattcc cctctagaaa taattttgtt taaccttaag aaggagatat    240

accatgagcg ataaaattat tcacctgact gacgacagtt ttgacacgga tgtactcaaa    300

gcggacgggg cgatcctcgt cgatttctgg gcagagtggt gtggtccgtg caaaatgatc    360

gccccgattc tggatgaaat cgctgacgaa tatcagggca aactgaccgt tgcaaaactg    420

aacatcgatc aaaaccctgg cactgcgccg aaatatggca tccgtggtat cccgactctg    480

ctgctgttca aaaacggtga agtggcggca accaaagtgg gtgcactgtc taaaggtcag    540

ttgaaagagt tcctcgacgc taacctggcg ggtgacacta gtggtaccat ggtcgacggt    600

actgcaggtt ccaaaagcaa cgaaccgggt aaagcaaccg gtgagggtaa accggttaac    660

aacaaatggc tgaacaacgc cggtaaagac ctgggttccc cggttcctga ccgcatcgcg    720

aataagctgc gcgataagga atttgaatcc tttgacgatt tccgtgaaac cttttgggaa    780

gaagtctcta aagacccgga actgagcaaa cagttctccc gcaacaacaa cgaccgcatg    840
```

-continued

```
aaagtgggca aagctccgaa aacccgtact caagacgttt ctggcaaacg cactagcttt    900
gaactgaacc atcagaagcc gattgaacaa aacggcggtg tttatgatat ggacaacatc    960
tccgtggtta cgccgaaacg taacattgac atcgaaggta ctgcaggtca cgtcggtgat   1020
ggttctctgc aagattctga agttaatcag gaagctaaac cggaagttaa accggaagtt   1080
aaaccagaaa ctcacattaa cctgaaagtg agcgatggtt cttccgaaat ctttttcaag   1140
attaaaaaga ctactccgct gcgtcgtctg atggaagcat tcgcgaaacg ccaaggtaaa   1200
gaaatggatt ctctgcgctt tctgtatgac ggcattcgca ttcaggctga ccaagcaccg   1260
gaggatctgg acatggaaga taatgacatt attgaagctc atcgtgaaca gatcggtggc   1320
agcactggtc tggaagtcct gttccaaggc ccgggtcaag cttcttaatg actcgagcac   1380
caccaccacc accactgaga tccggctgct aacaaagccc gaaaggaagc tgagttggct   1440
gctgccaccg ctgagcaata actagcataa ccccttgggg cctctaaacg ggtcttgagg   1500
ggttttttgc tgaaaggagg aactatatcc ggattggcga atgggacgcg ccctgtagcg   1560
gcgcattaag cgcggcgggt gtggtggtta cgcgcagcgt gaccgctaca cttgccagcg   1620
ccctagcgcc cgctcctttc gctttcttcc cttcctttct cgccacgttc gccggctttc   1680
cccgtcaagc tctaaatcgg gggctccctt tagggttccg atttagtgct ttacggcacc   1740
tcgaccccaa aaaacttgat tagggtgatg gttcacgtag tgggccatcg ccctgataga   1800
cggtttttcg ccctttgacg ttggagtcca cgttctttaa tagtggactc ttgttccaaa   1860
ctggaacaac actcaaccct atctcggtct attcttttga tttataaggg attttgccga   1920
tttcggccta ttggttaaaa aatgagctga tttaacaaaa atttaacgcg aattttaaca   1980
aaatattaac gtttacaatt tcaggtggca cttttcgggg aaatgtgcgc ggaaccccta   2040
tttgtttatt tttctaaata cattcaaata tgtatccgct catgaattaa ttcttagaaa   2100
aactcatcga gcatcaaatg aaactgcaat ttattcatat caggattatc aataccatat   2160
ttttgaaaaa gccgtttctg taatgaagga gaaaactcac cgaggcagtt ccataggatg   2220
gcaagatcct ggtatcggtc tgcgattccg actcgtccaa catcaataca acctattaat   2280
ttcccctcgt caaaaataag gttatcaagt gagaaatcac catgagtgac gactgaatcc   2340
ggtgagaatg gcaaaagttt atgcatttct ttccagactt gttcaacagg ccagccatta   2400
cgctcgtcat caaaatcact cgcatcaacc aaaccgttat tcattcgtga ttgcgcctga   2460
gcgagacgaa atacgcgatc gctgttaaaa ggacaattac aaacaggaat cgaatgcaac   2520
cggcgcagga acactgccag cgcatcaaca atattttcac ctgaatcagg atattcttct   2580
aatacctgga atgctgtttt cccggggatc gcagtggtga gtaaccatgc atcatcagga   2640
gtacggataa aatgcttgat ggtcggaaga ggcataaatt ccgtcagcca gtttagtctg   2700
accatctcat ctgtaacatc attggcaacg ctacctttgc catgtttcag aaacaactct   2760
ggcgcatcgg gcttcccata caatcgatag attgtcgcac ctgattgccc gacattatcg   2820
cgagcccatt tatacccata taaatcagca tccatgttgg aatttaatcg cggcctagag   2880
caagacgttt cccgttgaat atggctcata acaccccttg tattactgtt tatgtaagca   2940
gacagtttta ttgttcatga ccaaaatccc ttaacgtgag ttttcgttcc actgagcgtc   3000
agaccccgta gaaaagatca aaggatcttc ttgagatcct ttttttctgc gcgtaatctg   3060
ctgcttgcaa acaaaaaaac caccgctacc agcggtggtt tgtttgccgg atcaagagct   3120
accaactctt tttccgaagg taactggctt cagcagagcg cagataccaa atactgtcct   3180
```

-continued

```
tctagtgtag ccgtagttag gccaccactt caagaactct gtagcaccgc ctacatacct   3240
cgctctgcta atcctgttac cagtggctgc tgccagtggc gataagtcgt gtcttaccgg   3300
gttggactca agacgatagt taccggataa ggcgcagcgg tcgggctgaa cggggggttc   3360
gtgcacacag cccagcttgg agcgaacgac ctacaccgaa ctgagatacc tacagcgtga   3420
gctatgagaa agcgccacgc ttcccgaagg gagaaaggcg gacaggtatc cggtaagcgg   3480
cagggtcgga acaggagagc gcacgaggga gcttccaggg ggaaacgcct ggtatcttta   3540
tagtcctgtc gggtttcgcc acctctgact tgagcgtcga tttttgtgat gctcgtcagg   3600
ggggcggagc ctatggaaaa acgccagcaa cgcggccttt ttacggttcc tggccttttg   3660
ctggcctttt gctcacatgt tctttcctgc gttatcccct gattctgtgg ataaccgtat   3720
taccgccttt gagtgagctg ataccgctcg ccgcagccga acgaccgagc gcagcgagtc   3780
agtgagcgag gaagcggaag agcgcctgat gcggtatttt ctccttacgc atctgtgcgg   3840
tatttcacac cgcatatatg gtgcactctc agtacaatct gctctgatgc cgcatagtta   3900
agccagtata cactccgcta tcgctacgtg actgggtcat ggctgcgccc cgacacccgc   3960
caacacccgc tgacgcgccc tgacgggctt gtctgctccc ggcatccgct tacagacaag   4020
ctgtgaccgt ctccgggagc tgcatgtgtc agaggttttc accgtcatca ccgaaacgcg   4080
cgaggcagct gcggtaaagc tcatcagcgt ggtcgtgaag cgattcacag atgtctgcct   4140
gttcatccgc gtccagctcg ttgagtttct ccagaagcgt taatgtctgg cttctgataa   4200
agcgggccat gttaagggcg gtttttttcct gtttggtcac tgatgcctcc gtgtaagggg   4260
gatttctgtt catgggggta atgataccga tgaaacgaga gaggatgctc acgatacggg   4320
ttactgatga tgaacatgcc cggttactgg aacgttgtga gggtaaacaa ctggcggtat   4380
ggatgcggcg ggaccagaga aaaatcactc agggtcaatg ccagcgcttc gttaatacag   4440
atgtaggtgt tccacagggt agccagcagc atcctgcgat gcagatccgg aacataatgg   4500
tgcagggcgc tgacttccgc gtttccagac tttacgaaac acggaaaccg aagaccattc   4560
atgttgttgc tcaggtcgca gacgttttgc agcagcagtc gcttcacgtt cgctcgcgta   4620
tcggtgattc attctgctaa ccagtaaggc aaccccgcca gcctagccgg gtcctcaacg   4680
acaggagcac gatcatgcgc acccgtgggg ccgccatgcc ggcgataatg gcctgcttct   4740
cgccgaaacg tttggtggcg ggaccagtga cgaaggcttg agcgagggcg tgcaagattc   4800
cgaataccgc aagcgacagg ccgatcatcg tcgcgctcca gcgaaagcgg tcctcgccga   4860
aaatgaccca gagcgctgcc ggcacctgtc ctacgagttg catgataaag aagacagtca   4920
taagtgcggc gacgatagtc atgccccgcg cccaccggaa ggagctgact gggttgaagg   4980
ctctcaaggg catcggtcga gatcccggtg cctaatgagt gagctaactt acattaattg   5040
cgttgcgctc actgcccgct ttccagtcgg gaaacctgtc gtgccagctg cattaatgaa   5100
tcggccaacg cgcggggaga ggcggtttgc gtattgggcg ccagggtggt ttttcttttc   5160
accagtgaga cgggcaacag ctgattgccc ttcaccgcct ggccctgaga gagttgcagc   5220
aagcggtcca cgctggtttg ccccagcagg cgaaaatcct gtttgatggt ggttaacggc   5280
gggatataac atgagctgtc ttcggtatcg tcgtatccca ctaccgagat atccgcacca   5340
acgcgcagcc cggactcggt aatggcgcgc attgcgccca gcgccatctg atcgttggca   5400
accagcatcg cagtgggaac gatgccctca ttcagcattt gcatggtttg ttgaaaaccg   5460
gacatggcac tccagtcgcc ttcccgttcc gctatcggct gaatttgatt gcgagtgaga   5520
tatttatgcc agccagccag acgcagacgc gccgagacag aacttaatgg gcccgctaac   5580
```

-continued agcgcgattt gctggtgacc caatgcgacc agatgctcca cgcccagtcg cgtaccgtct 5640
tcatgggaga aaataatact gttgatgggt gtctggtcag agacatcaag aaataacgcc 5700
ggaacattag tgcaggcagc ttccacagca atggcatcct ggtcatccag cggatagtta 5760
atgatcagcc cactgacgcg ttgcgcgaga agattgtgca ccgccgcttt acaggcttcg 5820
acgccgcttc gttctaccat cgacaccacc acgctggcac ccagttgatc ggcgcgagat 5880
ttaatcgccg cgacaatttg cgacggcgcg tgcagggcca gactggaggt ggcaacgcca 5940
atcagcaacg actgtttgcc cgccagttgt tgtgccacgc ggttgggaat gtaattcagc 6000
tccgccatcg ccgcttccac tttttcccgc gttttcgcag aaacgtggct ggcctggttc 6060
accacgcggg aaacggtctg ataagagaca ccggcatact ctgcgacatc gtataacgtt 6120
actggtttca cattcaccac cctgaattga ctctcttccg ggcgctatca tgccataccg 6180
cgaaaggttt tgcgccattc gatggtgtcc gggatctcga cgctctccct tatgcgactc 6240
ctgcattagg aagcagccca gtagtaggtt gaggccgttg agcaccgccg ccgcaaggaa 6300
tggtgcatgc aaggagatgg cgcccaacag tcccccggcc acggggcctg ccaccatacc 6360
c 6361

<210> SEQ ID NO 15
<211> LENGTH: 6361
<212> TYPE: DNA
<213> ORGANISM: Artificial sequence
<220> FEATURE:
<223> OTHER INFORMATION: Synthetic construct

<400> SEQUENCE: 15
acgccgaaac aagcgctcat gagcccgaag tggcgagccc gatcttcccc atcggtgatg 60
tcggcgatat aggcgccagc aaccgcacct gtggcgccgg tgatgccggc cacgatgcgt 120
ccggcgtaga ggatcgagat ctcgatcccg cgaaattaat acgactcact ataggggaat 180
tgtgagcgga taacaattcc cctctagaaa taattttgtt taactttaag aaggagatat 240
accatgagcg ataaaattat tcacctgact gacgacagtt ttgacacgga tgtactcaaa 300
gcggacgggg cgatcctcgt cgatttctgg gcagagtggt gtggtccgtg caaaatgatc 360
gccccgattc tggatgaaat cgctgacgaa tatcagggca aactgaccgt tgcaaaactg 420
aacatcgatc aaaaccctgg cactgcgccg aaatatggca tccgtggtat cccgactctg 480
ctgctgttca aaaacggtga agtggcggca accaaagtgg gtgcactgtc taaaggtcag 540
ttgaaagagt tcctcgacgc taacctggcg ggtgacacta gtggtaccat ggtcgacggt 600
actgcaggtt ccaaaagcaa cgaaccgggt aaagcaaccg gtgagggtaa accggttaac 660
aacaaatggc tgaacaacgc cggtaaagac ctgggttccc cggttcctga ccgcatcgcg 720
aataagctgc gcgataagga atttgaatcc tttgacgatt tccgtgaaac cttttgggaa 780
gaagtctcta aagacccgga actgagcaaa cagttctccc gcaacaacaa cgaccgcatg 840
aaagtgggca aagctccgaa aacccgtact caagacgttt ctggcaaacg cactagcttt 900
gaactgaacc atcagaagcc gattgaacaa aacggcggtg tttatgatat ggacaacatc 960
tccgtggtta cgccgaaacg taacattgac atcgaaggta ctgcaggtca cgtcggtgat 1020
ggttctctgc aagattctga agttaatcag gaagctaaac cggaagttaa accggaagtt 1080
aaaccagaaa ctcacattaa cctgaaagtg agcgatggtt cttccgaaat ctttttcaag 1140
attaaaaaga ctactccgct gcgtcgtctg atggaagcat tcgcgaaacg ccaaggtaaa 1200

-continued

```
gaaatggatt ctctgcgctt tctgtatgac ggcattcgca ttcaggctga ccaagcaccg   1260
gaggatctgg acatggaaga taatgacatt attgaagctc atcgtgaaca gatcggtggc   1320
agcactggtc tggaagtcct gttccaaggc ccgggtcaag cttcttaatg actcgagcac   1380
caccaccacc accactgaga tccggctgct aacaaagccc gaaaggaagc tgagttggct   1440
gctgccaccg ctgagcaata actagcataa ccccttgggg cctctaaacg ggtcttgagg   1500
ggttttttgc tgaaaggagg aactatatcc ggattggcga atgggacgcg ccctgtagcg   1560
gcgcattaag cgcggcgggt gtggtggtta cgcgcagcgt gaccgctaca cttgccagcg   1620
ccctagcgcc cgctcctttc gctttcttcc cttcctttct cgccacgttc gccggctttc   1680
cccgtcaagc tctaaatcgg gggctccctt tagggttccg atttagtgct ttacggcacc   1740
tcgaccccaa aaaacttgat tagggtgatg gttcacgtag tgggccatcg ccctgataga   1800
cggtttttcg ccctttgacg ttggagtcca cgttctttaa tagtggactc ttgttccaaa   1860
ctggaacaac actcaaccct atctcggtct attcttttga tttataaggg attttgccga   1920
tttcggccta ttggttaaaa aatgagctga tttaacaaaa atttaacgcg aattttaaca   1980
aaatattaac gtttacaatt tcaggtggca cttttcgggg aaatgtgcgc ggaaccccta   2040
tttgtttatt tttctaaata cattcaaata tgtatccgct catgaattaa ttcttagaaa   2100
aactcatcga gcatcaaatg aaactgcaat ttattcatat caggattatc aataccatat   2160
ttttgaaaaa gccgtttctg taatgaagga gaaaactcac cgaggcagtt ccataggatg   2220
gcaagatcct ggtatcggtc tgcgattccg actcgtccaa catcaataca acctattaat   2280
ttcccctcgt caaaaataag gttatcaagt gagaaatcac catgagtgac gactgaatcc   2340
ggtgagaatg gcaaaagttt atgcatttct ttccagactt gttcaacagg ccagccatta   2400
cgctcgtcat caaaatcact cgcatcaacc aaaccgttat tcattcgtga ttgcgcctga   2460
gcgagacgaa atacgcgatc gctgttaaaa ggacaattac aaacaggaat cgaatgcaac   2520
cggcgcagga acactgccag cgcatcaaca atattttcac ctgaatcagg atattcttct   2580
aatacctgga atgctgtttt cccggggatc gcagtggtga gtaaccatgc atcatcagga   2640
gtacggataa aatgcttgat ggtcggaaga ggcataaatt ccgtcagcca gtttagtctg   2700
accatctcat ctgtaacatc attggcaacg ctacctttgc catgtttcag aaacaactct   2760
ggcgcatcgg gcttcccata caatcgatag attgtcgcac ctgattgccc gacattatcg   2820
cgagcccatt tatacccata taaatcagca tccatgttgg aatttaatcg cggcctagag   2880
caagacgttt cccgttgaat atggctcata acaccccttg tattactgtt tatgtaagca   2940
gacagtttta ttgttcatga ccaaaatccc ttaacgtgag ttttcgttcc actgagcgtc   3000
agaccccgta gaaaagatca aaggatcttc ttgagatcct ttttttctgc gcgtaatctg   3060
ctgcttgcaa acaaaaaaac caccgctacc agcggtggtt tgtttgccgg atcaagagct   3120
accaactctt tttccgaagg taactggctt cagcagagcg cagataccaa atactgtcct   3180
tctagtgtag ccgtagttag gccaccactt caagaactct gtagcaccgc ctacatacct   3240
cgctctgcta atcctgttac cagtggctgc tgccagtggc gataagtcgt gtcttaccgg   3300
gttggactca agacgatagt taccggataa ggcgcagcgg tcgggctgaa cggggggttc   3360
gtgcacacag cccagcttgg agcgaacgac ctacaccgaa ctgagatacc tacagcgtga   3420
gctatgagaa agcgccacgc ttcccgaagg gagaaaggcg gacaggtatc cggtaagcgg   3480
cagggtcgga acaggagagc gcacgaggga gcttccaggg ggaaacgcct ggtatcttta   3540
tagtcctgtc gggtttcgcc acctctgact tgagcgtcga tttttgtgat gctcgtcagg   3600
```

-continued

```
ggggcggagc ctatggaaaa acgccagcaa cgcggccttt ttacggttcc tggccttttg   3660
ctggcctttt gctcacatgt tctttcctgc gttatcccct gattctgtgg ataaccgtat   3720
taccgccttt gagtgagctg ataccgctcg ccgcagccga acgaccgagc gcagcgagtc   3780
agtgagcgag gaagcggaag agcgcctgat gcggtatttt ctccttacgc atctgtgcgg   3840
tatttcacac cgcatatatg gtgcactctc agtacaatct gctctgatgc cgcatagtta   3900
agccagtata cactccgcta tcgctacgtg actgggtcat ggctgcgccc cgacacccgc   3960
caacacccgc tgacgcgccc tgacgggctt gtctgctccc ggcatccgct tacagacaag   4020
ctgtgaccgt ctccgggagc tgcatgtgtc agaggttttc accgtcatca ccgaaacgcg   4080
cgaggcagct gcggtaaagc tcatcagcgt ggtcgtgaag cgattcacag atgtctgcct   4140
gttcatccgc gtccagctcg ttgagtttct ccagaagcgt taatgtctgg cttctgataa   4200
agcgggccat gttaagggcg gttttttcct gtttggtcac tgatgcctcc gtgtaagggg   4260
gatttctgtt catgggggta atgataccga tgaaacgaga gaggatgctc acgatacggg   4320
ttactgatga tgaacatgcc cggttactgg aacgttgtga gggtaaacaa ctggcggtat   4380
ggatgcggcg ggaccagaga aaaatcactc agggtcaatg ccagcgcttc gttaatacag   4440
atgtaggtgt tccacagggt agccagcagc atcctgcgat gcagatccgg aacataatgg   4500
tgcagggcgc tgacttccgc gtttccagac tttacgaaac acggaaaccg aagaccattc   4560
atgttgttgc tcaggtcgca gacgttttgc agcagcagtc gcttcacgtt cgctcgcgta   4620
tcggtgattc attctgctaa ccagtaaggc aaccccgcca gcctagccgg gtcctcaacg   4680
acaggagcac gatcatgcgc acccgtgggg ccgccatgcc ggcgataatg gcctgcttct   4740
cgccgaaacg tttggtggcg ggaccagtga cgaaggcttg agcgagggcg tgcaagattc   4800
cgaataccgc aagcgacagg ccgatcatcg tcgcgctcca gcgaaagcgg tcctcgccga   4860
aaatgaccca gagcgctgcc ggcacctgtc ctacgagttg catgataaag aagacagtca   4920
taagtgcggc gacgatagtc atgccccgcg cccaccggaa ggagctgact gggttgaagg   4980
ctctcaaggg catcggtcga gatcccggtg cctaatgagt gagctaactt acattaattg   5040
cgttgcgctc actgcccgct ttccagtcgg gaaacctgtc gtgccagctg cattaatgaa   5100
tcggccaacg cgcggggaga ggcggtttgc gtattgggcg ccagggtggt ttttcttttc   5160
accagtgaga cgggcaacag ctgattgccc ttcaccgcct ggccctgaga gagttgcagc   5220
aagcggtcca cgctggtttg ccccagcagg cgaaaatcct gtttgatggt ggttaacggc   5280
gggatataac atgagctgtc ttcggtatcg tcgtatccca ctaccgagat atccgcacca   5340
acgcgcagcc cggactcggt aatggcgcgc attgcgccca gcgccatctg atcgttggca   5400
accagcatcg cagtgggaac gatgccctca ttcagcattt gcatggtttg ttgaaaaccg   5460
gacatggcac tccagtcgcc ttcccgttcc gctatcggct gaatttgatt gcgagtgaga   5520
tatttatgcc agccagccag acgcagacgc gccgagacag aacttaatgg gcccgctaac   5580
agcgcgattt gctggtgacc caatgcgacc agatgctcca cgcccagtcg cgtaccgtct   5640
tcatgggaga aaataatact gttgatgggt gtctggtcag agacatcaag aaataacgcc   5700
ggaacattag tgcaggcagc ttccacagca atggcatcct ggtcatccag cggatagtta   5760
atgatcagcc cactgacgcg ttgcgcgaga agattgtgca ccgccgcttt acaggcttcg   5820
acgccgcttc gttctaccat cgacaccacc acgctggcac ccagttgatc ggcgcgagat   5880
ttaatcgccg cgacaatttg cgacggcgcg tgcagggcca gactggaggt ggcaacgcca   5940
```

-continued atcagcaacg actgtttgcc cgccagttgt tgtgccacgc ggttgggaat gtaattcagc 6000
tccgccatcg ccgcttccac tttttcccgc gttttcgcag aaacgtggct ggcctggttc 6060
accacgcggg aaacggtctg ataagagaca ccggcatact ctgcgacatc gtataacgtt 6120
actggtttca cattcaccac cctgaattga ctctcttccg ggcgctatca tgccataccg 6180
cgaaaggttt tgcgccattc gatggtgtcc gggatctcga cgctctccct tatgcgactc 6240
ctgcattagg aagcagccca gtagtaggtt gaggccgttg agcaccgccg ccgcaaggaa 6300
tggtgcatgc aaggagatgg cgcccaacag tcccccggcc acggggcctg ccaccatacc 6360
c 6361

<210> SEQ ID NO 16
<211> LENGTH: 5976
<212> TYPE: DNA
<213> ORGANISM: Artificial sequence
<220> FEATURE:
<223> OTHER INFORMATION: Synthetic construct

<400> SEQUENCE: 16
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620

-continued

```
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
```

-continued

```
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgggcaaaa tcgaagaagg taaacaggaa   5100
acctggaata acggcgataa aggctataac ggtcgtgctg aagacggtct ggaagtcctg   5160
ttccaaggcc caggtcaagc ttctagcggc cgcgaaggta ctagtgatgg cctggaagta   5220
ctgtttcaag gtccgaacgg tgaagataac cagagcaacc atcaccacca tcatcatcac   5280
cacaatcagg ctgaaaactc tgccgcaaac aatgcgtctg acgacggtaa ccagagctct   5340
aacgagtctt cttccgatgg cgaacaggca aacaccgact ctgcacacga aggtggcacc   5400
gcaggttcca aaagcaacga accgggtaaa gcaactggtg agggtaaacc agttaacaac   5460
aaatggctga acaacgccgg taaagacctg ggttccccgg ttcctgaccg catcgcgaat   5520
aagctgcgcg ataaggaatt tgaatccttt gacgatttcc gtgaaacctt ttgggaagaa   5580
gtctctaaag acccggaact gagcaaacag ttctcccgca acaacaacga ccgcatgaaa   5640
gtgggcaaag ctccgaaaac ccgtactcaa gacgtttctg gcaaacgcac tagctttgaa   5700
ctgaaccatc agaagccgat tgaacaaaac ggcggtgttt atgatatgga caacatctcc   5760
gtggttacgc cgaaacgtaa catcgatatc gaaggttaat taagctgaac aagctcgagc   5820
accaccacca ccaccactga gatccggctg ctaacaaagc ccgaaaggaa gctgagttgg   5880
ctgctgccac cgctgagcaa taactagcat aaccccttgg ggcctctaaa cgggtcttga   5940
ggggtttttt gctgaaagga ggaactatat ccggat                             5976
```

<210> SEQ ID NO 17
<211> LENGTH: 6678
<212> TYPE: DNA
<213> ORGANISM: Artificial sequence
<220> FEATURE:
<223> OTHER INFORMATION: Synthetic construct

<400> SEQUENCE: 17

```
tggcgaatgg gacgcgccct gtagcggcgc attaagcgcg gcgggtgtgg tggttacgcg     60
```

-continued

```
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
```

-continued

```
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
```

```
ccggccacgg ggcctgccac catacccacg ccgaaacaag cgctcatgag cccgaagtgg   4860

cgagcccgat cttccccatc ggtgatgtcg gcgatatagg cgccagcaac cgcacctgtg   4920

gcgccggtga tgccggccac gatgcgtccg gcgtagagga tcgagatctc gatcccgcga   4980

aattaatacg actcactata ggggaattgt gagcggataa caattcccct ctagaaataa   5040

ttttgtttaa ctttaagaag gagatatacc atgaactata tgaaacgtcg tctgctgctg   5100

ttcgcaggta tcctgctgct ggtagctctg gcaggttctt ctactacgga tccaattacc   5160

tctgaatctg aaggcatttg gaaccacttt ttcgtatatc cgatgtcttg gctgattact   5220

acggtggcga acctgctgaa cggtagctac ggtctgtcca ttatcattgt caccatcctg   5280

attcgtctgg ctctgctgcc tctgacgctg aaacagcaaa aaagcatgcg tgccatgcag   5340

gtgattcgcc ctgaaatgga agctattcag aaaaagtaca aagagaaagg ttctaaagat   5400

cctaaggtac agcaagaaat gcagaaagaa ctgctgggtc tgtaccagaa acacggtgta   5460

aacccgatgg ctggctgtct gcctctgttt atccaactgc cgattctgat ggcgttctac   5520

tttgcgatta tgcgtacgga agagattcgt tatcatacgt ttctgtggtt tgatctgggt   5580

caacctgact acattctgcc ttttgttgct ggcatcacta cgtactttca gttcaaaatg   5640

acgatgagcc atcagcaaca gatgcagaaa acgaatccgt ccgattccga taacccaatg   5700

gcgaacatga tgcagatgca gatgaaagtg atgctgtatg taatgccggt tatgatcatc   5760

atcgcgggtc tgtccctgcc atccgctctg tctctgtact gggtgatcgg caacatcttt   5820

atgattattc agacgtactt tatcgtcgtt aaagcaccac cgctggaagt cgaacagacc   5880

aaacaaaaat cttccggtgg cactagtgat ggcctggaag tactgtttca aggtccgaac   5940

ggtgaagata accagagcaa ccatcaccac catcatcatc accacaatca ggctgaaaac   6000

tctgccgcaa acaatgcgtc tgacgacggt aaccagagct ctaacgagtc ttcttccgat   6060

ggcgaacagg caaacaccga ctctgcacac gaaggtggca ccgcaggttc caaaagcaac   6120

gaaccgggta aagcaactgg tgagggtaaa ccagttaaca acaaatggct gaacaacgcc   6180

ggtaaagacc tgggttcccc ggttcctgac cgcatcgcga ataagctgcg cgataaggaa   6240

tttgaatcct ttgacgattt ccgtgaaacc ttttgggaag aagtctctaa agacccggaa   6300

ctgagcaaac agttctcccg caacaacaac gaccgcatga aagtgggcaa agctccgaaa   6360

acccgtactc aagacgtttc tggcaaacgc actagctttg aactgaacca tcagaagccg   6420

attgaacaaa acggcggtgt ttatgatatg gacaacatct ccgtggttac gccgaaacgt   6480

aacatcgata tcgaaggtta attaagctga acaagctcga gcaccaccac caccaccact   6540

gagatccggc tgctaacaaa gcccgaaagg aagctgagtt ggctgctgcc accgctgagc   6600

aataactagc ataacccctt ggggcctcta aacgggtctt gaggggtttt ttgctgaaag   6660

gaggaactat atccggat                                                 6678
```

<210> SEQ ID NO 18
<211> LENGTH: 7752
<212> TYPE: DNA
<213> ORGANISM: Artificial sequence
<220> FEATURE:
<223> OTHER INFORMATION: Synthetic construct

<400> SEQUENCE: 18

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120
```

-continued

```
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
```

gttttcaccg tcatcaccga aacgcgcgag gcagctgcgg taaagctcat cagcgtggtc 2580
gtgaagcgat tcacagatgt ctgcctgttc atccgcgtcc agctcgttga gtttctccag 2640
aagcgttaat gtctggcttc tgataaagcg ggccatgtta agggcggttt tttcctgttt 2700
ggtcactgat gcctccgtgt aagggggatt tctgttcatg gggtaatga taccgatgaa 2760
acgagagagg atgctcacga tacgggttac tgatgatgaa catgcccggt tactggaacg 2820
ttgtgagggt aaacaactgg cggtatggat gcggcgggac cagagaaaaa tcactcaggg 2880
tcaatgccag cgcttcgtta atacagatgt aggtgttcca cagggtagcc agcagcatcc 2940
tgcgatgcag atccggaaca taatggtgca gggcgctgac ttccgcgttt ccagacttta 3000
cgaaacacgg aaaccgaaga ccattcatgt tgttgctcag gtcgcagacg ttttgcagca 3060
gcagtcgctt cacgttcgct cgcgtatcgg tgattcattc tgctaaccag taaggcaacc 3120
ccgccagcct agccgggtcc tcaacgacag gagcacgatc atgcgcaccc gtggggccgc 3180
catgccggcg ataatggcct gcttctcgcc gaaacgtttg gtggcgggac cagtgacgaa 3240
ggcttgagcg agggcgtgca agattccgaa taccgcaagc gacaggccga tcatcgtcgc 3300
gctccagcga aagcggtcct cgccgaaaat gacccagagc gctgccggca cctgtcctac 3360
gagttgcatg ataaagaaga cagtcataag tgcggcgacg atagtcatgc cccgcgccca 3420
ccggaaggag ctgactgggt tgaaggctct caagggcatc ggtcgagatc ccggtgccta 3480
atgagtgagc taacttacat taattgcgtt gcgctcactg cccgctttcc agtcgggaaa 3540
cctgtcgtgc cagctgcatt aatgaatcgg ccaacgcgcg gggagaggcg gtttgcgtat 3600
tgggcgccag ggtggttttt cttttcacca gtgagacggg caacagctga ttgcccttca 3660
ccgcctggcc ctgagagagt tgcagcaagc ggtccacgct ggtttgcccc agcaggcgaa 3720
aatcctgttt gatggtggtt aacggcggga tataacatga gctgtcttcg gtatcgtcgt 3780
atcccactac cgagatatcc gcaccaacgc gcagcccgga ctcggtaatg gcgcgcattg 3840
cgcccagcgc catctgatcg ttggcaacca gcatcgcagt gggaacgatg ccctcattca 3900
gcatttgcat ggtttgttga aaaccggaca tggcactcca gtcgccttcc cgttccgcta 3960
tcggctgaat ttgattgcga gtgagatatt tatgccagcc agccagacgc agacgcgccg 4020
agacagaact taatgggccc gctaacagcg cgatttgctg gtgacccaat gcgaccagat 4080
gctccacgcc cagtcgcgta ccgtcttcat gggagaaaat aatactgttg atgggtgtct 4140
ggtcagagac atcaagaaat aacgccggaa cattagtgca ggcagcttcc acagcaatgg 4200
catcctggtc atccagcgga tagttaatga tcagcccact gacgcgttgc gcgagaagat 4260
tgtgcaccgc cgctttacag gcttcgacgc cgcttcgttc taccatcgac accaccacgc 4320
tggcacccag ttgatcggcg cgagatttaa tcgccgcgac aatttgcgac ggcgcgtgca 4380
gggccagact ggaggtggca acgccaatca gcaacgactg tttgcccgcc agttgttgtg 4440
ccacgcggtt gggaatgtaa ttcagctccg ccatcgccgc ttccactttt tcccgcgttt 4500
tcgcagaaac gtggctggcc tggttcacca cgcgggaaac ggtctgataa gagacaccgg 4560
catactctgc gacatcgtat aacgttactg gtttcacatt caccaccctg aattgactct 4620
cttccgggcg ctatcatgcc ataccgcgaa aggttttgcg ccattcgatg gtgtccggga 4680
tctcgacgct ctcccttatg cgactcctgc attaggaagc agcccagtag taggttgagg 4740
ccgttgagca ccgccgccgc aaggaatggt gcatgcaagg agatggcgcc caacagtccc 4800
ccggccacgg ggcctgccac catacccacg ccgaaacaag cgctcatgag cccgaagtgg 4860

```
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ccttaagaag gagatatacc atgaactata tgaaacgtcg tctgctgctg   5100
ttcgcaggta tcctgctgct ggtagctctg gcaggttctt ctactaccga tgcagatgct   5160
agcggcaaac atcaccatca ccatcaccat cacaaatctc aagcttctgg tctgccagaa   5220
actggtgaaa acggtgatac ggatcctgac ggtcatgatg gtcatgatga cgatgtgatt   5280
gatatcgagg atgacctgga cgatgtcatt gaagaggtag aagactctaa accagatacc   5340
actgctcctc cttcttctcc gaaagttact tacaaagctc cagttccaac tggcgaagta   5400
tattttgctg attcttttga ccgtggcact ctgtctggct ggattctgtc caaagccaaa   5460
aaagacgata ccgatgatga aattgccaaa tatgatggca aatgggaggt agaggaaatg   5520
aaagagagca aactgccagg tgataaaggt ctggtcctga tgtctcgcgc caaacatcat   5580
gccatctctg ctaaactgaa caagccgttc ctgtttgaca ccaaacctct gattgttcag   5640
tatgaggtta atttccaaaa tggtattgaa tgtggtggtg cctatgtgaa actgctgtct   5700
aaaactccag aactgaacct ggatcagttc catgacaaaa cccccttatac gattatgttt   5760
ggtccagata aatgtggtga ggactataaa ctgcacttca tcttccgtca caaaaacccg   5820
aaaacgggta tctatgaaga aaaacatgct aagcgcccag atgcagatct gaaaacctat   5880
tttactgaca aaaaaactca tctgtacact ctgatcctga atccagataa tagctttgaa   5940
atcctggttg accaatctgt tgtcaatagc ggtaatctgc tgaatgacat gactcctcct   6000
gtaaatcctt ctcgtgaaat tgaggaccca gaagaccgca aaccggagga ttgggatgaa   6060
cgtccaaaaa tcccagatcc agaagctgtc aaaccagatg actgggatga agatgcccct   6120
gctaaaattc cggatgaaga ggccactaaa ccggaaggct ggctggatga tgaacctgag   6180
tacgtacctg atccagacgc agagaaacct gaagactggg acgaagacat ggatggtgaa   6240
tgggaagctc ctcagattgc caaccctcgt tgtgagtctg ctcctggttg tggtgtctgg   6300
cagcgtcctg tgattgacaa cccgaattac aaaggcaaat ggaaacctcc tatgattgac   6360
aatccgagct accagggtat ctggaaaccg cgtaaaatcc caaatccaga tttctttgaa   6420
gatctggaac ctttccgtat gactcctttt agcgctattg gtctggaact gtggtccatg   6480
acctctgaca tctttttcga caactttatc atttgtgctg atcgtcgcat tgttgatgat   6540
tgggccaatg atggttgggg cctgaaaaaa gctgctgatg gtgctgctga accaggcgtt   6600
gtgggtcaga tgatcgaagc agctgaagaa cgcccgtggc tgtgggtagt ctatattctg   6660
actgtagccc tgcctgtgtt cctggttatc ctgttctgct gcagcggcaa aaaacagacc   6720
tctggtatgg aatacaaaaa aactgatgca cctcaaccgg atgtgaagga agaggaggaa   6780
gagaaagagg aagaaaaaga taaaggtgac gaggaggagg aaggcgagga gaaactggaa   6840
gagaaacaga aaagcgatgc tgaagaagat ggtggcactg tcagccaaga agaagaggat   6900
cgtaaaccta aagcagaaga agatgaaatt ctgaacagcg gccgcgaagg tactagtaat   6960
ggtgatggcc tggaagtact gtttcaaggt ccaggtctgc ctgagaccgg taatggtgaa   7020
gataaccaga gcaacggtgc tcagaatggt atcgatggca atcaggctga aaactctgct   7080
gcaaacaatg cgtctgacga cggtaaccag agctctaacg agtcttcttc cgatggcgaa   7140
caggcaaaca ccgactctgc acacgaaggt ggcaccgcag gttccaaaag caacgaaccg   7200
ggtaaagcaa ctggtgaggg taaaccagtt aacaacaaat ggctgaacaa cgccggtaaa   7260
```

```
gacctgggtt ccccggttcc tgaccgcatc gcgaataagc tgcgcgataa ggaatttgaa   7320
tcctttgacg atttccgtga aaccttttgg gaagaagtct ctaaagaccc ggaactgagc   7380
aaacagttct cccgcaacaa caacgaccgc atgaaagtgg gcaaagctcc gaaaacccgt   7440
actcaagacg tttctggcaa acgcactagc tttgaactga accatcagaa gccgattgaa   7500
caaaacggcg gtgtttatga tatggacaac atctccgtgg ttacgccgaa acgtaacatc   7560
gatatcgaag gttaattaag ctgaacaagc tcgagcacca ccaccaccac cactgagatc   7620
cggctgctaa caaagcccga aaggaagctg agttggctgc tgccaccgct gagcaataac   7680
tagcataacc ccttggggcc tctaaacggg tcttgagggg ttttttgctg aaaggaggaa   7740
ctatatccgg at                                                        7752
```

<210> SEQ ID NO 19
<211> LENGTH: 6394
<212> TYPE: DNA
<213> ORGANISM: Artificial sequence
<220> FEATURE:
<223> OTHER INFORMATION: Synthetic construct

<400> SEQUENCE: 19

```
gcccgatctt ccccatcggt gatgtcggcg atataggcgc cagcaaccgc acctgtggcg     60
ccggtgatgc cggccacgat gcgtccggcg tagaggatcg agatctcgat cccgcgaaat    120
taatacgact cactataggg gaattgtgag cggataacaa ttcccctcta gaaataattt    180
tgtttaacct taagaaggag atataccatg agcgataaaa ttattcacct gactgacgac    240
agttttgaca cggatgtact caaagcggac ggggcgatcc tcgtcgattt ctgggcagag    300
tggtgtggtc cgtgcaaaat gatcgccccg attctggatg aaatcgctga cgaatatcag    360
ggcaaactga ccgttgcaaa actgaacatc gatcaaaacc ctggcactgc gccgaaatat    420
ggcatccgtg gtatcccgac tctgctgctg ttcaaaaacg gtgaagtggc ggcaaccaaa    480
gtgggtgcac tgtctaaagg tcagttgaaa gagttcctcg acgctaacct ggcgggtgac    540
actagtggta ccggcgctga aggccgtcgt ggtgaagaag cgggcaaaca ccatcaccat    600
caccatcacc acggtaaagg cgcggaagag ggtcgtcgcg gtgaagctgg cctggaagtc    660
ctgttccaag gcccgggtca agcttctggt accaccatgg gcaaaatcga agaaggtaaa    720
caggaaacct ggaataacgg cgataaaggc tataacggtc gtgctgaaga cggtggttgt    780
ggtggtgcta ttgaagaact ggaagaagaa gtacgtcgtc accagatgcg tctgatggcc    840
ctgcaactgg aagaacagct gatgggtggc tgtggtgacg tcggtgacat ggagttccgt    900
aactctatct ctgattacac cgaggaagaa tttgttcgcc tgctgcgcgg tattgagcgc    960
gagaatgttg cggctactga cgaccgtctg gactggatgc tggaacactt tgtcgaaatt   1020
accgaacacc cagacggcac tgacctgatt tactatccgt ctgataaccg tgatgattct   1080
ccagaaggca tcgttgaaga aattcgtgag tggcgtgagg cgaatggtcg tcctggcttc   1140
aagcagggcg gttctaccga tggcggcgac gtcggtgaag aacgtaaccg tcgttgcgaa   1200
gagctgaacg aagagatcga ggaacaccgt gaacgtctgc gtcagctgga ggaaacccgc   1260
gaagaatgtc gcaccggcac tgctaaaagc gaagagggca aacaggaaac ttctaatcat   1320
ggtgataaag gtacgaacgg tcaggcagaa gatagcggcc gctaatgact cgagcaccac   1380
caccaccacc actgagatcc ggctgctaac aaagcccgaa aggaagctga gttggctgct   1440
gccaccgctg agcaataact agcataaccc cttggggcct ctaaacgggt cttgaggggt   1500
```

-continued

```
tttttgctga aaggaggaac tatatccgga ttggcgaatg ggacgcgccc tgtagcggcg   1560
cattaagcgc ggcgggtgtg gtggttacgc gcagcgtgac cgctacactt gccagcgccc   1620
tagcgcccgc tcctttcgct ttcttccctt cctttctcgc cacgttcgcc ggctttcccc   1680
gtcaagctct aaatcggggg ctccctttag ggttccgatt tagtgcttta cggcacctcg   1740
accccaaaaa acttgattag ggtgatggtt cacgtagtgg gccatcgccc tgatagacgg   1800
tttttcgccc tttgacgttg gagtccacgt tctttaatag tggactcttg ttccaaactg   1860
gaacaacact caaccctatc tcggtctatt cttttgattt ataagggatt ttgccgattt   1920
cggcctattg gttaaaaaat gagctgattt aacaaaaatt taacgcgaat tttaacaaaa   1980
tattaacgtt tacaatttca ggtggcactt ttcggggaaa tgtgcgcgga acccctattt   2040
gtttattttt ctaaatacat tcaaatatgt atccgctcat gaattaattc ttagaaaaac   2100
tcatcgagca tcaaatgaaa ctgcaattta ttcatatcag gattatcaat accatatttt   2160
tgaaaaagcc gtttctgtaa tgaaggagaa aactcaccga ggcagttcca taggatggca   2220
agatcctggt atcggtctgc gattccgact cgtccaacat caatacaacc tattaatttc   2280
ccctcgtcaa aaataaggtt atcaagtgag aaatcaccat gagtgacgac tgaatccggt   2340
gagaatggca aaagtttatg catttctttc cagacttgtt caacaggcca gccattacgc   2400
tcgtcatcaa aatcactcgc atcaaccaaa ccgttattca ttcgtgattg cgcctgagcg   2460
agacgaaata cgcgatcgct gttaaaagga caattacaaa caggaatcga atgcaaccgg   2520
cgcaggaaca ctgccagcgc atcaacaata ttttcacctg aatcaggata ttcttctaat   2580
acctggaatg ctgttttccc ggggatcgca gtggtgagta accatgcatc atcaggagta   2640
cggataaaat gcttgatggt cggaagaggc ataaattccg tcagccagtt tagtctgacc   2700
atctcatctg taacatcatt ggcaacgcta cctttgccat gtttcagaaa caactctggc   2760
gcatcgggct tcccatacaa tcgatagatt gtcgcacctg attgcccgac attatcgcga   2820
gcccatttat acccatataa atcagcatcc atgttggaat ttaatcgcgg cctagagcaa   2880
gacgtttccc gttgaatatg gctcataaca ccccttgtat tactgtttat gtaagcagac   2940
agttttattg ttcatgacca aaatccctta acgtgagttt tcgttccact gagcgtcaga   3000
ccccgtagaa aagatcaaag gatcttcttg agatcctttt tttctgcgcg taatctgctg   3060
cttgcaaaca aaaaaaccac cgctaccagc ggtggtttgt ttgccggatc aagagctacc   3120
aactcttttt ccgaaggtaa ctggcttcag cagagcgcag ataccaaata ctgtccttct   3180
agtgtagccg tagttaggcc accacttcaa gaactctgta gcaccgccta catacctcgc   3240
tctgctaatc ctgttaccag tggctgctgc cagtggcgat aagtcgtgtc ttaccgggtt   3300
ggactcaaga cgatagttac cggataaggc gcagcggtcg ggctgaacgg ggggttcgtg   3360
cacacagccc agcttggagc gaacgaccta caccgaactg agatacctac agcgtgagct   3420
atgagaaagc gccacgcttc ccgaagggag aaaggcggac aggtatccgg taagcggcag   3480
ggtcggaaca ggagagcgca cgagggagct tccaggggga aacgcctggt atctttatag   3540
tcctgtcggg tttcgccacc tctgacttga gcgtcgattt ttgtgatgct cgtcaggggg   3600
gcggagccta tggaaaaacg ccagcaacgc ggccttttta cggttcctgg ccttttgctg   3660
gccttttgct cacatgttct ttcctgcgtt atcccctgat tctgtggata accgtattac   3720
cgcctttgag tgagctgata ccgctcgccg cagccgaacg accgagcgca gcgagtcagt   3780
gagcgaggaa gcggaagagc gcctgatgcg gtattttctc cttacgcatc tgtgcggtat   3840
ttcacaccgc atatatggtg cactctcagt acaatctgct ctgatgccgc atagttaagc   3900
```

```
cagtatacac tccgctatcg ctacgtgact gggtcatggc tgcgccccga cacccgccaa   3960
cacccgctga cgcgccctga cgggcttgtc tgctcccggc atccgcttac agacaagctg   4020
tgaccgtctc cgggagctgc atgtgtcaga ggttttcacc gtcatcaccg aaacgcgcga   4080
ggcagctgcg gtaaagctca tcagcgtggt cgtgaagcga ttcacagatg tctgcctgtt   4140
catccgcgtc cagctcgttg agtttctcca gaagcgttaa tgtctggctt ctgataaagc   4200
gggccatgtt aagggcggtt ttttcctgtt tggtcactga tgcctccgtg taagggggat   4260
ttctgttcat gggggtaatg ataccgatga aacgagagag gatgctcacg atacgggtta   4320
ctgatgatga acatgcccgg ttactggaac gttgtgaggg taaacaactg gcggtatgga   4380
tgcggcggga ccagagaaaa atcactcagg gtcaatgcca gcgcttcgtt aatacagatg   4440
taggtgttcc acagggtagc cagcagcatc ctgcgatgca gatccggaac ataatggtgc   4500
agggcgctga cttccgcgtt tccagacttt acgaaacacg gaaaccgaag accattcatg   4560
ttgttgctca ggtcgcagac gttttgcagc agcagtcgct tcacgttcgc tcgcgtatcg   4620
gtgattcatt ctgctaacca gtaaggcaac cccgccagcc tagccgggtc ctcaacgaca   4680
ggagcacgat catgcgcacc cgtggggccg ccatgccggc gataatggcc tgcttctcgc   4740
cgaaacgttt ggtggcggga ccagtgacga aggcttgagc gagggcgtgc aagattccga   4800
ataccgcaag cgacaggccg atcatcgtcg cgctccagcg aaagcggtcc tcgccgaaaa   4860
tgacccagag cgctgccggc acctgtccta cgagttgcat gataaagaag acagtcataa   4920
gtgcggcgac gatagtcatg ccccgcgccc accggaagga gctgactggg ttgaaggctc   4980
tcaagggcat cggtcgagat cccggtgcct aatgagtgag ctaacttaca ttaattgcgt   5040
tgcgctcact gcccgctttc cagtcgggaa acctgtcgtg ccagctgcat taatgaatcg   5100
gccaacgcgc ggggagaggc ggtttgcgta ttgggcgcca gggtggtttt tcttttcacc   5160
agtgagacgg gcaacagctg attgcccttc accgcctggc cctgagagag ttgcagcaag   5220
cggtccacgc tggtttgccc cagcaggcga aaatcctgtt tgatggtggt taacggcggg   5280
atataacatg agctgtcttc ggtatcgtcg tatcccacta ccgagatatc cgcaccaacg   5340
cgcagcccgg actcggtaat ggcgcgcatt gcgcccagcg ccatctgatc gttggcaacc   5400
agcatcgcag tgggaacgat gccctcattc agcatttgca tggtttgttg aaaaccggac   5460
atggcactcc agtcgccttc ccgttccgct atcggctgaa tttgattgcg agtgagatat   5520
ttatgccagc cagccagacg cagacgcgcc gagacagaac ttaatgggcc cgctaacagc   5580
gcgatttgct ggtgacccaa tgcgaccaga tgctccacgc ccagtcgcgt accgtcttca   5640
tgggagaaaa taatactgtt gatgggtgtc tggtcagaga catcaagaaa taacgccgga   5700
acattagtgc aggcagcttc cacagcaatg gcatcctggt catccagcgg atagttaatg   5760
atcagcccac tgacgcgttg cgcgagaaga ttgtgcaccg ccgctttaca ggcttcgacg   5820
ccgcttcgtt ctaccatcga caccaccacg ctggcaccca gttgatcggc gcgagattta   5880
atcgccgcga caatttgcga cggcgcgtgc agggccagac tggaggtggc aacgccaatc   5940
agcaacgact gtttgcccgc cagttgttgt gccacgcggt tgggaatgta attcagctcc   6000
gccatcgccg cttccacttt ttcccgcgtt ttcgcagaaa cgtggctggc ctggttcacc   6060
acgcgggaaa cggtctgata agagacaccg gcatactctg cgacatcgta taacgttact   6120
ggtttcacat tcaccaccct gaattgactc tcttccgggc gctatcatgc cataccgcga   6180
aaggttttgc gccattcgat ggtgtccggg atctcgacgc tctcccttat gcgactcctg   6240
```

-continued cattaggaag cagcccagta gtaggttgag gccgttgagc accgccgccg caaggaatgg 6300
tgcatgcaag gagatggcgc ccaacagtcc cccggccacg gggcctgcca ccatacccac 6360
gccgaaacaa gcgctcatga gcccgaagtg gcga 6394

<210> SEQ ID NO 20
<211> LENGTH: 15883
<212> TYPE: DNA
<213> ORGANISM: Artificial sequence
<220> FEATURE:
<223> OTHER INFORMATION: Synthetic construct

<400> SEQUENCE: 20
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380
cccttgtatt actgtttatg taagcagaca gttttattgt tcatgaccaa aatcccttaa 1440
cgtgagtttt cgttccactg agcgtcagac cccgtagaaa agatcaaagg atcttcttga 1500
gatccttttt ttctgcgcgt aatctgctgc ttgcaaacaa aaaaaccacc gctaccagcg 1560
gtggtttgtt tgccggatca agagctacca actctttttc cgaaggtaac tggcttcagc 1620
agagcgcaga taccaaatac tgtccttcta gtgtagccgt agttaggcca ccacttcaag 1680
aactctgtag caccgcctac atacctcgct ctgctaatcc tgttaccagt ggctgctgcc 1740
agtggcgata agtcgtgtct taccgggttg gactcaagac gatagttacc ggataaggcg 1800
cagcggtcgg gctgaacggg gggttcgtgc acacagccca gcttggagcg aacgacctac 1860
accgaactga gatacctaca gcgtgagcta tgagaaagcg ccacgcttcc cgaagggaga 1920

-continued

```
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggtaatga taccgatgaa    2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
```

```
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacc atgggcaaaa tcgaagaagg taaacaggaa   5100
acctggaata acggcgataa aggctataac ggtcgtgctg aagacggtct ggaagtcctg   5160
ttccaaggcc caggcacctc aggtggcacc atgggcctgg attccaagct gaaggcacca   5220
gtcttcacgg tgcgcaccca gggtcgtgag tacggtgagt tcgtcctgga accgctggag   5280
cgtggcttcg gcgtcaccct gggcaaccca ctgcgtcgca tcctcctgtc ttccatccct   5340
ggtactgcgg tcaccagcgt ctacattgag gatgtcctgc acgagttctc caccatcccg   5400
ggcgttaaag aggacgttgt agagattatc ctgaacctga aggaactggt tgttcgtttc   5460
ctgaacccga gcctgcaaac cgtgaccctg ctcctgaaag ccgaaggccc aaaggaagtt   5520
aaggcacgcg acttcctgcc agttgccgac gttgagatca tgaacccgga cctgcacatc   5580
gccaccctgg aagagggcgg tcgtctgaac atggaggtcc gcgttgatcg cggcgttggt   5640
tacgtcccgg cggaaaaaca cggcatcaag gaccgtatca acgccatccc ggtggacgcc   5700
gtcttctccc cggtgcgtcg cgtggctttc caggtggaag acactcgcct gggtcaacgc   5760
accgacctgg acaagctgac cctccgtatc tggaccgacg gctccgtcac cccgctggag   5820
gccttaaacc aggcggttga gatcctgcgt gagcacctga cctacttctc caacccgcaa   5880
gcggcagccg ttgcggcacc ggaagaggct aaagagccgg aagcgccgcc agagcaggag   5940
gaagagctgg acctgccgct ggaagagctt ggcctgtcca cccgcgttct gcacagcctg   6000
aaggaagagg gcattgagtc cgtccgcgca ctgctggcac tgaacctgaa agacctgaag   6060
aacatcccag gtattggcga acgtagcctg gaagagatca aggaagccct ggagaagaaa   6120
ggcttcaccc tgaaagagta atgaatttaa atagtaaata tggcctcaaa taacgtaaaa   6180
acccgcttcg gcgggttttt ttatgggggg agtttaggga aagagcattt gtcagaatca   6240
agcatcaatg actgcagact taagaaggag atataccatg agcgataaaa ttaatcacca   6300
gactgacgac agttatgaca cggatgtaga caaagcggac ggcgcgaacc aggtcgacta   6360
ctccgcagag ctggaagtcc tgttccaagg ccctggtcaa gcttctggtg cggacggtgg   6420
tatggaaatc aaacgtttcg gtcgcatccg tgaagttatc ccgctgccgc cgctgaccga   6480
aatccaggtg gaatcctacc gccgtgcgct gcaagccgat gtcccgccgg agaaacgtga   6540
gaacgtcggc atccaggcgg ccttccgtga aaccttcccg attgaagaag aggacaaggg   6600
caaaggcggt ctggttctgg acttcctgga ataccgcctg ggcgaaccac cgtttccgca   6660
```

-continued

```
ggacgagtgc cgtgagaaag acctgaccta tcaggctccg ctgtacgccc gtctgcaact   6720
gatccacaaa gacacgggcc tgatcaagga agacgaggtc ttcctgggtc acatcccgct   6780
gatgaccgag gacggttcct tcatcatcaa cggtgccgac cgtgtcatcg tttcccagat   6840
ccatcgctcc ccgggtgtct acttcacccc agatccggcg cgcccaggtc gctacatcgc   6900
ctctatcatt ccgctgccga aacgtggccc gtggattgac ctcgaagtgg aaccgaacgg   6960
cgttgtctcc atgaaggtca acaaacgtaa gttcccgctg gttctgctgc tgcgtgtcct   7020
gggttacgac caggaaaccc tggcacgcga gctgggcgct tacggcgagc tggtacaggg   7080
cctgatggac gagtctgtct tcgctatgcg cccggaagag gctctgatcc gcctgttcac   7140
cctgctgcgc ccgggtgatc caccgaaacg tgacaaggct gtggcctacg tctacggcct   7200
gatcgctgac ccgcgccgtt acgacctggg cgaagccggt cgttacaagg cggaagagaa   7260
actgggtatc cgcctgtctg gtcgcaccct ggctcgcttt gaggacggtg agttcaaaga   7320
cgaggtcttc ctgccgaccc tgcgttacct gttcgccctg accgccggtg ttccgggcca   7380
cgaggtggac gacattgacc atctgggcaa ccgccgcatc cgcaccgtgg gtgagctgat   7440
gaccgaccag ttccgtgtgg gtctggctcg cctggcacgt ggtgttcgtg agcgtatgct   7500
gatgggctct gaggacagcc tgaccccggc taagctggtc aacagccgtc cgctggaagc   7560
cgctatccgt gaattcttca gccgcagcca gctgtcccag ttcaaagacg agactaaccc   7620
gctgtcctct ctgcgtcaca aacgtcgcat ctccgctctg ggtccaggtg gtctgactcg   7680
cgaacgtgcg ggttttgacg tgcgcgacgt tcaccgcacc cactacggtc gcatctgccc   7740
ggttgaaacc cctgaaggcg ccaacatcgg cctgatcacc tccctggcgg cttacgcccg   7800
tgtggacgag ctcggcttca tccgcacccc gtatcgccgt gttgtgggcg gtgtggtcac   7860
cgacgaagtg gtctacatga cggccaccga agaggaccgc tacaccatcg cccaggccaa   7920
caccccgctg gagggtaacc gtatcgcggc agaacgcgtc gttgctcgtc gcaagggtga   7980
acctgttatc gttagccctg aacaggttga gttcatggat gtctccccga agcaggtctt   8040
ctccgtgaac accaacctga ttccgttcct ggagcacgac gacgccaacc gtgccctgat   8100
gggctccaac atgcagaccc aagccgtgcc gctgatccgt gcacaggctc cggtggtgat   8160
gacgggcctg gaagagcgtg tcgttcgcga ctccctggca gccctgtacg ccgaagagga   8220
tggcgaagtt gccaaggttg acggcaaccg catcgtcgtt cgctacgaag acggtcgcct   8280
ggttgagtat ccgctgcgtc gcttctaccg ctccaaccag ggtacggccc tggatcagcg   8340
tccgcgtgtg gttgtgggtc agcgtgtgcg caaaggtgac ctgctggctg acggcccagc   8400
ctccgagaac ggcttcctgg ccctgggtca gaacgtcctg gttgccatca tgccgtttga   8460
cggttacaac tttgaggacg ccatcgtcat cagcgaagag ctgctgaaac gcgacttcta   8520
cacctccatc cacattgagc gctacgagat tgaggctcgt gacaccaaac tgggcccgga   8580
acgtatcacc cgtgacatcc cgcacctgtc cgaagcagcc ctgcgtgacc tggacgagga   8640
aggcgttgtc cgcatcggcg ctgaggtcaa accaggcgac atcctggttg gtcgtaccag   8700
cttcaagggc gaatccgagc cgaccccaga ggaacgtctg ctgcgctcca tcttcggcga   8760
gaaagctcgc gacgttaagg acacctccct gcgcgttccg ccaggcgaag gcggtatcgt   8820
tgtacgtacc gtccgtctgc gtcgtgggga tccgggtgtg gagctgaagc cgggtgtgcg   8880
tgaggtcgta cgtgtctacg ttgcccagaa gcgcaagctg caagttggcg acaagctggc   8940
caaccgccac ggtaacaagg gtgtggttgc caaaatcctg ccggtggagg acatgccgca   9000
```

-continued

```
cctgccagac ggtactccgg tggacgtgat cctgaacccg ctgggcgtcc caagccgtat   9060
gaacctgggt cagatcctgg aaacccacct gggcctggcc ggttacttcc tgggccagcg   9120
ctacatctct ccgatctttg acggtgccaa ggagccggag atcaaagagc tgctggctca   9180
ggcctttgag gtctacttcg gcaagcgcaa aggcgaaggc ttcggcgttg acaagcgtga   9240
ggtggaagtc ctgcgccgtg cggaaaagct gggcctggtc accccgggca aaaccccgga   9300
agagcaactg aaggaactgt tcctgcaagg caaggttgtc ctgtacgacg gccgcacggg   9360
cgaaccgatt gagggcccga tcgtcgttgg tcagatgttc atcatgaagc tgtaccacat   9420
ggttgaggac aagatgcacg ctcgctccac gggtccgtac tccctgatca cccagcaacc   9480
gctgggcggt aaggcccagt tcggcggtca gcgcttcggt gagatggagg tctgggcact   9540
ggaggcctac ggtgcggctc acaccctgca agagatgctg accctgaaat ccgacgacat   9600
tgagggccgt aacgctgcct acgaggccat catcaagggt gaagacgttc cggaaccgag   9660
cgtcccggag tccttccgcg tgctggtgaa agagctgcaa gcactggccc tggacgttca   9720
gaccctggac gagaaagaca acccggttga catctttgag ggtctggcct ccaaacgtgg   9780
ccaagaaggc caaaatcacc atcaccatca ccattaatga cctaggataa ttctcgctca   9840
aacaggtcac tgctgtcggg ttaaaacccg gcagcggatt gtgctaaatt cgagcaccgt   9900
cgatctcgat cccgcgaaat tgtagaaata attttgttta actttaagaa ggagatatac   9960
catgggcaac aaagaaattt tgggtgaaga tgaagccgaa tccaatgaaa aggcgcaagc  10020
aggcgagaag aattacgagg ccttgggtac cctggaagtt ctgtttcagg gtccgggcga  10080
ctctgcgtct ggtatgaaaa aagaggttcg taaggttcgc atcgctctgg cctccccgga  10140
aaagatccgc tcctggagct atggcgaggt tgagaaaccg gagactatca actaccgcac  10200
cctgaagccg gaacgtgacg gcctgtttga cgagcgcatc ttcggcccga tcaaggacta  10260
cgagtgcgcc tgcggcaagt acaaacgcca gcgctttgag ggcaaagttt gcgagcgttg  10320
cggtgttgag gtgacgaagt ctatcgtccg ccgctaccgc atgggtcaca ttgagctggc  10380
caccccggct gcccacatct ggttcgtcaa ggatgtcccg tccaagatcg gtactctgct  10440
ggacctgtcc gccaccgagc tggaacaggt cctgtacttc agcaagtaca tcgtcctgga  10500
cccgaagggt gccatcctga acggtgtccc ggtggagaaa cgccagctgc tgaccgacga  10560
agagtatcgc gagctgcgct acggcaaaca ggagacgtac ccgctgccac cgggtgttga  10620
cgcgctggtg aaagacggtg aagaggttgt aaagggccag gagctggctc cgggcgttgt  10680
cagccgcctg gacggcgtgg ccctgtatcg cttcccgcgt cgcgttcgtg tggagtacgt  10740
gaagaaagaa cgcgccggtc tgcgtctgcc actggctgcc tgggttgaga aagaagccta  10800
caagccgggc gaaatcctgg ccgagctgcc ggagccgtac ctgttccgtg ccgaggaaga  10860
gggcgttgtt gagctgaaag agctggaaga aggcgctttc ctggtcctgc gtcgcgagga  10920
cgaacctgtt gccacctact tcctgccagt gggcatgact ccgctggtgg tccacggtga  10980
gatcgtggaa aagggccagc cactggccga agccaaaggc ctgctgcgca tgccacgcca  11040
ggttcgcgcc gcacaggtgg aagcggaaga ggaaggcgag acggtctacc tgaccctgtt  11100
cctggagtgg acggagccta aagactaccg cgtccagcca catatgaacg ttgttgtccc  11160
ggaaggtgca cgcgttgagg cgggcgacaa gatcgttgcc gccattgacc cggaagaaga  11220
ggtcatcgcc gaagccgagg gcgttgtcca cctgcacgag ccagccagca tcctggtggt  11280
caaagcccgt gtctacccgt ttgaggacga cgtggaggtt tccactggcg atcgcgttgc  11340
accgggtgat gtcctggccg acggtggcaa ggtcaaaagc gacgtttacg gccgcgttga  11400
```

```
ggtggatctg gtccgcaacg tggtccgtgt ggtggaatcc tacgacattg acgcccgcat  11460
gggtgccgag gccatccagc agctgctgaa agagctggac ctggaggccc tggagcgcga  11520
actgctggaa gagatgaaac acccatctcg cgcacgtcgc gctaaggccc gtaaacgcct  11580
ggaggttgtc cgtgccttcc tggactctgg taaccgtccg gagtggatga tcctggaagc  11640
cgtcccggtc ctgccaccgg acctgcgtcc gatggtccag gtggacggcg gtcgctttgc  11700
cacgagcgac ctgaacgacc tgtaccgtcg cctgatcaac cgcaacaacc gtctgaaaaa  11760
gctgctggcc cagggcgctc ctgagatcat catccgcaac gagaaacgta tgctgcaaga  11820
agcggttgac gccctgctgg acaacggtcg tcgcggcgct ccagttacca acccgggctc  11880
cgaccgtcca ctgcgtagcc tgaccgatat cctgtccggc aaacagggcc gcttccgcca  11940
gaacctgctg ggcaagcgtg tggactactc tggccgtagc gtgatcgtgg ttggtccgca  12000
gctgaagctg caccagtgcg gcctgccgaa acgtatggcc ctggaactgt tcaagccgtt  12060
cctgctgaag aagatggaag agaaaggcat cgcccccgaac gtcaaggcgg cgcgtcgtat  12120
gctggaacgc cagcgtgaca tcaaagacga ggtttgggac gccctggagg aagttatcca  12180
cggcaaagtt gtcctgctga accgcgcccc aaccctgcac cgcctgggca tccaggcctt  12240
ccaaccggtc ctggtggaag gtcagtccat ccagctgcac ccgctggtct gcgaggcctt  12300
caacgccgac tttgacggtg accagatggc tgtacatgtc ccactgtcct ccttcgccca  12360
ggccgaagcc cgcatccaga tgctgtccgc ccacaacctg ctgtctccag cctccggtga  12420
accactggcc aaaccgagcc gtgacatcat cctgggcctg tactacatca cccaggttcg  12480
caaagagaag aaaggcgctg gtctggagtt cgccaccccca gaagaagccc tggcagccca  12540
cgaacgcggc gaagttgccc tgaacgcccc gatcaaagtg gcgggccgtg aaaccagcgt  12600
gggtcgtctg aagtacgtct tcgccaaccc ggacgaagcc ctgctggccg ttgcccacgg  12660
catcgtggac ctgcaagacg tggtcaccgt ccgctacatg ggcaaacgtc tggagacgag  12720
cccgggtcgc atcctgttcg cccgcatcgt ggccgaagcg gtggaagacg agaaggttgc  12780
ctgggagctg atccagctgg acgttccgca ggagaagaac tccctgaaag accttgtcta  12840
ccaggccttc ctgcgcctgg gtatggagaa aaccgcccgt ctgctggacg ccctgaagta  12900
ctacggcttc accttctcca ccactagcgg catcaccatc ggcattgacg acgccgtgat  12960
cccggaagag aaaaagcagt acctggagga agcggaccgc aaactgctgc aaattgaaca  13020
ggcctacgag atgggcttcc tgaccgaccg tgagcgttac gaccagatcc tgcaactgtg  13080
gaccgaaacc acggagaaag tcacccaggc ggtcttcaag aacttcgaag aaaactaccc  13140
attcaacccg ctgtacgtca tggcccagtc cggtgcacgt ggcaacccgc agcagatccg  13200
ccagctgtgc ggtctgcgtg gcctgatgca gaaaccgtct ggcgaaacct ttgaggttcc  13260
ggttcgctct tccttccgcg aaggcctgac cgtcctggag tacttcatct cctctcacgg  13320
tgcccgtaaa ggcggtgcgg ataccgcact gcgtaccgcc gactccggct acctgacccg  13380
caaactggtg gacgtcaccc acgagatcgt ggtgcgtgaa gcggactgcg gcaccaccaa  13440
ctacatctcc gttccgctgt tccagccaga cgaagtgacc cgctccctgc gcctgcgtaa  13500
acgcgcggac attgaggccg gcctgtacgg tcgtgtcctg gcccgtgaag tggaggtcct  13560
gggtgttcgc ctggaagagg gtcgctacct gtctatggac gacgttcacc tgctgatcaa  13620
agccgctgaa gccggtgaga tccaggaagt tccggttcgc agcccgctga cctgccagac  13680
ccgctacggt gtttgccaga agtgctacgg ttacgacctg tctatggccc gtccagtctc  13740
```

```
catcggcgaa gcggtgggca tcgtggcagc ccagtccatc ggcgaaccag gcacccaatt  13800
gaccatgcgt accttccata cgggtggcgt ggctggtgca gcggacatca cccagggtct  13860
cccgcgtgtc attgagctgt ttgaggcccg tcgcccgaaa gccaaagcgg tgatctccga  13920
gattgacggt gttgttcgca ttgaggaaac ggaggaaaag ctgtccgtct tcgttgagtc  13980
cgagggcttc tccaaagagt acaagctgcc gaaagaggcg cgtctgctgg tcaaggatgg  14040
cgactacgtt gaagcgggcc agccactgac ccgtggtgcc attgacccgc atcagctgct  14100
ggaagccaag ggcccggaag cggttgaacg ctatctggtt gaagagatcc agaaagtcta  14160
ccgcgcccag ggcgttaaac tgcacgacaa acacattgag atcgttgtcc gtcagatgat  14220
gaagtacgtg gaagtcaccg acccgggtga cagccgcctg ctggaaggcc aggttctgga  14280
gaaatgggat gtcgaagccc tgaacgagcg tctgatcgcc gaaggcaaga ccccagtggc  14340
ctggaaaccg ctgctgatgg gtgtcacgaa gagcgccctg tccaccaaaa gctggctgtc  14400
cgcggctagc ttccagaaca ccacccacgt cctgaccgaa gcggccatcg ccggtaagaa  14460
agacgagctg atcggcctga aggagaacgt catcctgggc cgtctgatcc cggcaggtac  14520
tggttctgac ttcgtccgct ttacccaggt ggtggaccag aaaaccctga aggccattga  14580
ggaagcccgc aaagaggcgg ttgaggccaa ggaacgtcca gccgctcgtc gcggcgtcaa  14640
acgcgaacag ccgggcaaac aggctggcgg ccgcacttct ggcaacggtg atcagggcct  14700
ggaggtcctg ttccagggcc cgcagggtga aaactctggc acttctggca ccgacaatgg  14760
ctcttccgat ggcctggaag tgctgtttca aggcccagca ggtaattctg cgtctagcgg  14820
ttctggtggc ggtgctgaac caggtattga taaactgttc ggcatggttg attctaaata  14880
ccgtctgact gttgtggtag ccaaacgtgc gcagcaactg ctgcgtcacg gtttcaaaaa  14940
caccgttctg gaaccggaag aacgccctaa aatgcagacc ctggaaggcc tgttcgatga  15000
tccgaatgcc gtcacttggg ctatgaaaga actgctgact ggtcgcctgg tgtttggtga  15060
aaatctggtt ccggaagatc gtctgcaaaa agaaatggaa cgtctgtacc cggttgaacg  15120
tgaagaaact gctggcacta gtgatggcaa cggtgaagat aaccagggcc tggaagtact  15180
gtttcaaggt ccgcagggtg aaaactctgg ctctggcgac ggcgatggtg gcgagtcttc  15240
ttccgatggc acgctggagg tgctgttcca gggtcctggc ggtgactctg cacacgaagg  15300
tggcaccgca ggttccaaaa gcaacgaacc gggtaaagca actggtgagg gtaaaccagt  15360
taacaacaaa tggctgaaca acgccggtaa agacctgggt tccccggttc ctgaccgcat  15420
cgcgaataag ctgcgcgata aggaatttga atcctttgac gatttccgtg aaaccttttg  15480
ggaagaagtc tctaaagacc cggaactgag caaacagttc tcccgcaaca acaacgaccg  15540
catgaaagtg ggcaaagctc cgaaaacccg tactcaagac gtttctggca aacgcactag  15600
ctttgaactg aaccatcaga agccgattga acaaaacggc ggtgtttatg atatggacaa  15660
catctccgtg gttacgccga aacgtaacat cgatatcgaa ggttaattaa gctgaacaag  15720
ctcgagcacc accaccacca ccactgagat ccggctgcta acaaagcccg aaaggaagct  15780
gagttggctg ctgccaccgc tgagcaataa ctagcataac cccttggggc ctctaaacgg  15840
gtcttgaggg gttttttgct gaaaggagga actatatccg gat                   15883
```

<210> SEQ ID NO 21
<211> LENGTH: 15484
<212> TYPE: DNA
<213> ORGANISM: Artificial sequence
<220> FEATURE:
<223> OTHER INFORMATION: Synthetic construct

<400> SEQUENCE: 21

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
```

-continued

```
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
```

tctcgacgct ctcccttatg cgactcctgc attaggaagc agcccagtag taggttgagg 4740
ccgttgagca ccgccgccgc aaggaatggt gcatgcaagg agatggcgcc caacagtccc 4800
ccggccacgg ggcctgccac catacccacg ccgaaacaag cgctcatgag cccgaagtgg 4860
cgagcccgat cttccccatc ggtgatgtcg gcgatatagg cgccagcaac cgcacctgtg 4920
gcgccggtga tgccggccac gatgcgtccg gcgtagagga tcgagatctc gatcccgcga 4980
aattaatacg actcactata ggggaattgt gagcggataa caattcccct ctagaaataa 5040
ttttgtttaa ccttaagaag gagatatacc atgctgatct ctcagcgccc gaccctgtcc 5100
gaagatgtcc tgaccgacaa ccgttcccag ttcgtgatcg aaccgctgga accgggtttc 5160
ggctacaccc tgggcaattc tctgcgtcgc accctgctgt cttccattcc gggtgcggcc 5220
gttaccagca ttcgcatcga tggtgtactg cacgaattta ccacggttcc gggtgtcaaa 5280
gaagatgtca ccgaaatcat cctgaatctg aaaagcctgg ttgtatcttc cgaggaagac 5340
gaaccggtta ccatgtatct gcgcaaacag ggtccgggtg aagttaccgc cggcgacatc 5400
gtgccgccag caggtgttac cgtgcacaac ccgggcatgc acatcgccac gctgaacgat 5460
aaaggcaaac tggaagtcga gctggttgtc gaacgtggcc gtggctatgt tccggcggtg 5520
caaaaccgcg cttccggtgc cgaaattggt cgcattccag tcgattccat ctactctccg 5580
gttctgaaag tgacctacaa agtggacgcc acccgtgtcg aacagcgtac ggactttgac 5640
aaactgatcc tggacgttga aaccaaaaat tctatcagcc cgcgcgacgc gctggcgtcc 5700
gctggcaaaa cgctggtcga actgttcggc ctggcacgcg aactgaacgt cgaagccgaa 5760
ggcatcgaaa tcggtccatc cccggccgaa gccgatcaca ttgcgtcttt cgccctgccg 5820
atcgacgatc tggatctgac ggttcgttcc tacaactgcc tgaaacgcga aggcgttcac 5880
accgtgggcg aactggtagc gcgcaccgaa tccgacctgc tggacatccg caactttggt 5940
cagaaatcca tcgacgaagt gaaaatcaaa ctgcaccagc tgggcctgtc tctgaaagac 6000
agcccgccga gcttcgaccc gtccgaagtc gcgggctacg acgtagccac cggcacctgg 6060
tccaccgaag gtgcgtatga cgaacaggat tacgccgaaa ccgaacagct gtaatgaatt 6120
taaatagtaa atatggcctc aaataacgta aaaacccgct tcggcgggtt tttttatggg 6180
gggagtttag ggaaagagca tttgtcagaa tcaagcatca atgactgcag acttaagaag 6240
gagatatacc atgagcgata aaattaatca ccagactgac gacagttatg acacggatgt 6300
agacaaagcg gacggcgcga accaggtcga ctactccgca gagctggaag tcctgttcca 6360
aggccctggt caagcttctg gtgcggacgg tggtatgctg gaaggttgca tcctggcaga 6420
ttcccgccag agcaaaactg ccgcttctcc ttctccgtct cgcccgcaat cttccagcaa 6480
taactccgta ccgggcgcgc caaaccgtgt ctccttcgct aaactgcgcg aaccactgga 6540
agttccgggt ctgctggatg ttcagaccga ttcctttgaa tggctgatcg gttctccgcg 6600
ctggcgcgaa tccgcagccg aacgtggtga tgtcaaccca gtgggtggcc tggaagaagt 6660
gctgtacgaa ctgtctccga tcgaggactt ctccggttct atgtctctgt ccttctctga 6720
ccctcgtttc gacgatgtca aagcaccagt agacgagtgc aaagacaaag acatgacgta 6780
tgcggctcca ctgtttgtca ccgccgagtt catcaacaac aacaccggtg aaatcaaatc 6840
tcagacggtg ttcatgggtg acttcccgat gatgaccgag aaaggcacgt tcatcatcaa 6900
cggtactgaa cgtgtagttg tcagccagct ggtgcgttct ccgggtgtgt acttcgacga 6960
aaccattgac aaatccaccg acaaaacgct gcatagcgtc aaagtgatcc cgagccgcgg 7020

-continued

```
tgcgtggctg gagtttgatg tcgataaacg cgacaccgtc ggcgtgcgca tcgaccgcaa   7080
acgccgtcaa ccggtcaccg ttctgctgaa agcgctgggt tggaccagcg aacagattgt   7140
cgaacgtttc ggtttctccg agatcatgcg ttctacgctg gagaaagaca acactgtagg   7200
caccgatgaa gcgctgctgg acatctaccg caaactgcgt ccgggcgaac caccgaccaa   7260
agaatctgcg cagacgctgc tggaaaacct gttcttcaaa gagaaacgct acgacctggc   7320
ccgcgtcggt cgctataagg tcaacaaaaa actgggtctg catgtcggcg agcctatcac   7380
gtcttctacg ctgaccgaag aggatgtcgt ggccaccatc gaatatctgg tccgcctgca   7440
cgaaggtcag accacgatga ccgttccggg tggcgtcgaa gttccggttg aaaccgatga   7500
cattgaccac ttcggcaacc gtcgcctgcg tactgtcggc gaactgatcc aaaaccagat   7560
ccgtgtcggc atgtctcgta tggagcgtgt tgtccgtgag cgtatgacca cccaggatgt   7620
tgaagcgatc actccgcaaa ctctgatcaa cattcgtccg gtggtcgccg cgatcaaaga   7680
attcttcggc acctctcagc tgagccaatt tatggatcag aacaacccgc tgtctggtct   7740
gacccacaaa cgtcgcctgt ctgcgctggg tccaggcggt ctgtctcgtg agcgtgccgg   7800
tctggaagtc cgcgacgttc acccgtctca ttacggccgt atgtgcccga tcgaaacccc   7860
tgaaggtcca aacatcggtc tgatcggctc tctgtctgtt tacgcgcgtg tcaacccgtt   7920
cggtttcatc gagaccccgt accgcaaagt tgttgacggc gtagttagcg acgaaatcgt   7980
gtacctgacc gcagacgaag aagaccgcca cgtcgttgca caggccaatt ctccaatcga   8040
tgcggacggt cgcttcgtcg aaccgcgcgt tctggtccgt cgcaaagcgg gcgaagttga   8100
atacgtgccg tcttctgaag tagactacat ggacgtttct ccacgccaga tggtgtccgt   8160
ggcaaccgct atgattccgt ttctggaaca cgatgacgcc aaccgtgccc tgatgggtgc   8220
aaacatgcag cgccaggcgg ttccgctggt ccgtagcgaa gccccgctgg ttggcaccgg   8280
tatggaactg cgcgcagcga tcgacgcagg cgatgtcgtt gtagccgaag aaagcggcgt   8340
catcgaagaa gtgtctgccg actacatcac tgtgatgcac gataacggca cccgtcgtac   8400
ctaccgtatg cgcaagtttg cccgttccaa ccacggcact tgcgccaacc agtgcccaat   8460
cgtggacgcg ggtgaccgtg ttgaggccgg ccaggttatc gccgatggtc catgtactga   8520
cgacggcgaa atggcgctgg gcaaaaacct gctggttgcc atcatgccgt gggaaggcca   8580
caactacgaa gacgcgatca ttctgtccaa ccgcctggtc gaagaagacg ttctgacctc   8640
tatccacatc gaagaacatg agatcgatgc tcgcgacacc aaactgggtg cggaagagat   8700
cacccgcgac attccgaaca tctccgacga agttctggcc gacctggatg aacgtggcat   8760
tgtacgtatt ggtgccgaag ttcgcgacgg tgacatcctg gtcggcaaag tcaccccgaa   8820
aggtgagact gaactgacgc cggaagaacg tctgctgcgt gccatcttcg gtgagaaagc   8880
acgcgaagtg cgcgacactt ctctgaaagt gccgcacggc gaatccggca aagttatcgg   8940
cattcgtgtt ttttcccgcg aagacgaaga tgagctgcct gcaggtgtca atgaactggt   9000
tcgtgtgtat gtagctcaga aacgcaaaat ctccgatggt gataaactgg ctggccgtca   9060
cggcaacaaa ggcgtaatcg gcaaaatcct gccggttgaa gacatgccgt tcctggccga   9120
cggcaccccg gttgacatta ttctgaacac ccacggcgta ccgcgtcgta tgaacatcgg   9180
ccagattctg gaaacccacc tgggttggtg tgcccacagc ggctggaaag tcgatgcagc   9240
caaaggtgtt ccggactggg ctgcccgtct gccagacgaa ctgctggaag cgcaaccgaa   9300
cgccattgtg tctacgccgg tattcgacgg tgcccaggaa gccgaactgc agggcctgct   9360
gtcttgcacg ctgcctaacc gcgatggtga cgttctggta gatgccgacg gcaaagccat   9420
```

-continued

```
gctgttcgac ggtcgcagcg gcgaaccgtt cccgtacccg gtcacggttg gctacatgta   9480
tatcatgaaa ctgcaccatc tggtggacga caaaatccac gcccgctcca ccggtccgta   9540
ctctatgatc acccagcagc cgctgggcgg taaagcgcag ttcggtggcc agcgtttcgg   9600
tgaaatggaa tgctgggcaa tgcaggcata cggtgctgcc tacactctgc aggaactgct   9660
gaccatcaaa tccgatgaca ctgttggccg cgttaaagtg tacgaagcga tcgtcaaagg   9720
tgaaaacatc ccggaaccgg gcatcccgga atctttcaaa gtgctgctga aagaactgca   9780
gagcctgtgc ctgaacgtcg aagtgctgtc ctctgacggt gcggcgatcg aactgcgtga   9840
aggtgaagat gaagacctgg aacgtgccgc agccaacctg ggtatcaatc tgtcccgcaa   9900
cgaatccgca tctgtcgaag atctggcggg ccaagaaggc caaaatcacc atcaccatca   9960
ccattaatga cctaggataa ttctcgctca aacaggtcac tgctgtcggg ttaaaacccg  10020
gcagcggatt gtgctaaatt cgagcaccgt cgatctcgat cccgcgaaat tgtagaaata  10080
attttgttta actttaagaa ggagatatac catgggcaac aaagaaattt tgggtgaaga  10140
tgaagccgaa tccaatgaaa aggcgcaagc aggcgagaag aattacgagg ccttgggtac  10200
cctggaagtt ctgtttcagg gtccgggcga ctctgcgtct ggtatgctgg atgtcaactt  10260
ctttgatgaa ctgcgtatcg gtctggctac cgcagaagac atccgtcaat ggtcctatgg  10320
cgaagtcaaa aaaccggaaa cgatcaacta tcgcacgctg aaaccggaga aagacggcct  10380
gttctgcgag aaaatcttcg gtccaactcg cgattgggaa tgctactgcg gcaaatacaa  10440
acgtgtgcgc ttcaaaggca tcatctgcga acgctgcggc gtcgaagtta cccgcgccaa  10500
agttcgtcgt gaacgtatgg gccacatcga actggccgcg ccagtcaccc atatctggta  10560
cttcaaaggt gtgccttctc gtctgggtta tctgctggac ctggccccga aagacctgga  10620
gaaaatcatc tacttcgctg catatgttat cacctctgta gacgaagaaa tgcgccacaa  10680
tgaactgtcc acgctggaag ccgaaatggc ggttgaacgc aaagccgtcg aagaccagcg  10740
cgacggcgaa ctggaagccc gtgcgcaaaa actggaagcc gacctggccg agctggaagc  10800
agaaggcgcc aaagccgatg cgcgtcgcaa agttcgcgac ggtggcgaac gcgaaatgcg  10860
ccagatccgt gaccgcgcac agcgtgaact ggaccgtctg gaagacatct ggagcacttt  10920
caccaaactg gcgccaaaac agctgatcgt tgacgaaaac ctgtatcgcg aactggtcga  10980
tcgctacggc gaatacttca ccggtgccat gggcgcggaa tctatccaga aactgatcga  11040
aaacttcgac atcgacgccg aagccgaatc tctgcgtgat gtcatccgta acggcaaagg  11100
tcagaaaaaa ctgcgcgccc tgaaacgtct gaaagtggtt gctgcgttcc aacagtctgg  11160
caactctccg atgggcatgg ttctggacgc agtcccggtt atcccaccgg agctccgccc  11220
gatggttcag ctggacggtg gccgtttcgc cacgtccgac ctgaacgacc tgtaccgccg  11280
tgtaatcaac cgcaacaatc gtctgaagcg tctgatcgat ctgggtgctc cggaaatcat  11340
tgtcaacaac gaaaaacgta tgctgcagga atccgttgac gcgctgttcg acaatggccg  11400
tcgcggtcgt cctgtcactg gtccgggcaa ccgtccgctg aaatctctgt ccgatctgct  11460
gaaaggcaaa cagggccgtt tccgtcagaa cctgctgggc aaacgtgtcg attactctgg  11520
ccgtagcgtc atcgtagtcg gccctcagct gaaactgcat cagtgcggtc tgcctaaact  11580
gatggcgctg gaactgttca aaccgttcgt tatgaaacgt ctggtagacc tgaaccatgc  11640
gcagaacatc aaaagcgcca aacgcatggt tgaacgccag cgccctcaag tgtgggatgt  11700
gctggaagaa gtcatcgccg agcacccggt gctgctgaac cgcgcaccaa ccctgcaccg  11760
```

```
tctgggtatc caggcgttcg aaccaatgct ggttgaaggc aaagccattc agctgcaccc  11820
gctggtatgt gaagcgttca atgccgactt cgatggtgac cagatggctg tacacctgcc  11880
tctgagcgcc gaagcgcagg ccgaagctcg cattctgatg ctgtcttcca acaacatcct  11940
gtctccggca tctggtcgtc cgctggccat gccgcgtctg gacatggtga ccggtctgta  12000
ctatctgacc accgaggtcc ctggtgacac cggcgaatac cagccagcca gcggtgatca  12060
cccggaaact ggtgtctact cttctccggc cgaagcgatc atggcagccg accgtggtgt  12120
tctgagcgtg cgtgccaaaa tcaaagtgcg tctgacccag ctgcgtccac cggtcgaaat  12180
cgaagccgaa ctgtttggcc acagcggctg gcagccgggc gatgcgtgga tggccgaaac  12240
cacgctgggc cgtgtgatgt tcaacgaact gctgccgctg ggttatccgt tcgtcaacaa  12300
acagatgcac aagaaagtgc aggctgccat catcaacgac ctggccgaac gttacccgat  12360
gatcgttgtc gcccagaccg tcgataaact gaaagatgcc ggcttctatt gggccacccg  12420
cagcggcgta acggtttcta tggccgacgt tctggttcct cctcgcaaaa aggaaatcct  12480
ggaccactac gaagaacgcg cggacaaagt cgaaaagcag tttcagcgtg gcgctctgaa  12540
ccacgacgaa cgcaacgaag cgctggtaga aatttggaaa gaagccaccg acgaagtcgg  12600
tcaggcgctg cgtgaacact acccagacga taacccgatc attaccattg tcgattccgg  12660
tgccaccggc aacttcaccc agactcgtac tctggcaggt atgaaaggtc tggtaaccaa  12720
cccgaaaggt gagttcatcc cgcgtccggt caaatcctcc ttccgtgaag gcctgaccgt  12780
tctggaatac ttcatcaaca cccatggcgc tcgtaaaggt ctggcggaca ccgcgctgcg  12840
caccgccgat tccggctacc tgacccgtcg cctggtagac gtctcccagg acgttatcgt  12900
tcgcgaacac gattgccaga ccgaacgcgg catcgtagtc gaactggctg aacgtgcacc  12960
agacggcacg ctgatccgcg acccgtacat cgaaacctct gcctacgcgc gtaccctggg  13020
caccgacgca gtcgatgagg ctggcaacgt catcgtcgaa cgtggtcaag acctgggcga  13080
tccggaaatt gacgctctgc tggctgctgg tattacccag gtcaaagtgc gttctgtact  13140
gacgtgtgcc accagcaccg gcgtttgcgc gacctgctac ggtcgttcca tggccaccgg  13200
caaactggtc gatatcggtg aagccgtcgg catcgtagcc gctcagtcca tcggcgaacc  13260
tggcacccaa ttgaccatgc gcacctttca tcagggtggc gtcggtgaag acatcaccgg  13320
tggtctgcca cgtgttcagg aactgtttga agcccgtgtt ccgcgtggca aagcgccgat  13380
cgccgatgtc accggccgtg ttcgtctgga agacggcgaa cgtttctaca aaatcaccat  13440
cgttcctgac gatggcggtg aagaagttgt ctacgacaaa atctccaaac gtcagcgtct  13500
gcgtgtgttc aaacacgaag acggttccga acgtgtgctg tccgatggcg accacgtcga  13560
ggtaggccag cagctgatgg aaggcagcgc ggatccacat gaagtgctgc gtgttaaagg  13620
cccacgcgaa gtacagattc acctggttcg cgaagtccag gaagtctacc gcgcccaagg  13680
tgtttctatc cacgacaaac acatcgaagt aatcgttcgc cagatgctgc gccgtgttac  13740
catcattgac tctggctcta cggagtttct gcctggcagc ctgatcgatc gcgcggaatt  13800
tgaagcagaa aaccgccgtg tagttgccga aggcggtgaa cctgcggccg gtcgtccggt  13860
actgatgggc atcacgaaag cgtctctggc caccgactct tggctgtctg cggctagctt  13920
tcaggaaacc actcgcgttc tgaccgatgc tgcgatcaac tgccgcagcg acaaactgaa  13980
cggtctgaaa gaaaacgtga tcatcggcaa actgatcccg gccggtactg gtatcaaccg  14040
ctatcgcaac atcgcggtac agcctaccga agaagcccgc gctgcagcgt acaccatccc  14100
gtcttatgaa gatcagtact acagcccgga ctttggtgca gccaccggtg ctgccgtccc  14160
```

```
gctggatgac tacggctaca gcgactatcg tggcggccgc actggttctg gcaacggtga  14220

agataaccag ggcctggagg tcctgttcca gggcccgcag ggtgaaaact ctggctctgg  14280

cgacggcgat ggtggcgagt cttcttccga tggcacgctg gaagtgctgt ttcaaggccc  14340

aactggtaat tctgcgtcta gcggtgatga acagaacgca ggttctggtg gcggtatgtc  14400

tatcagccag tccgatgcga gcctggcagc agtcccagcc gttgatcagt tcgatccgtc  14460

ttccggtgca tctggtggct atgacacccc gctgggcatt accaatccgc ctattgacga  14520

actgctggac cgcgtttcta gcaaatacgc cctggtgatc tatgcggcaa aacgtgcccg  14580

tcagatcaac gattactaca accagctggg cgaaggcatc ctggaatatg ttggtccgct  14640

ggttgaaccg ggtctgcaag aaaaaccgct gtccatcgcg ctgcgcgaga tccacgccga  14700

tctgctggaa cacaccgaag gcgaaggtac tgctggcact agtgatggca acggtgaaga  14760

taaccagggc ctggaagtac tgtttcaagg tccgcagggt gaaaactctg gctctggcga  14820

cggcgatggt ggcgagtctt cttccgatgg cacgctggag gtgctgttcc agggtcctgg  14880

cggtgactct gcacacgaag gtggcaccgc aggttccaaa agcaacgaac cgggtaaagc  14940

aactggtgag ggtaaaccag ttaacaacaa atggctgaac aacgccggta aagacctggg  15000

ttccccggtt cctgaccgca tcgcgaataa gctgcgcgat aaggaatttg aatcctttga  15060

cgatttccgt gaaacctttt gggaagaagt ctctaaagac ccggaactga gcaaacagtt  15120

ctcccgcaac aacaacgacc gcatgaaagt gggcaaagct ccgaaaaccc gtactcaaga  15180

cgtttctggc aaacgcacta gctttgaact gaaccatcag aagccgattg aacaaaacgg  15240

cggtgtttat gatatggaca acatctccgt ggttacgccg aaacgtaaca tcgatatcga  15300

aggttaatta agctgaacaa gctcgagcac caccaccacc accactgaga tccggctgct  15360

aacaaagccc gaaaggaagc tgagttggct gctgccaccg ctgagcaata actagcataa  15420

ccccttgggg cctctaaacg ggtcttgagg ggttttttgc tgaaaggagg aactatatcc  15480

ggat                                                               15484
```

<210> SEQ ID NO 22
<211> LENGTH: 8
<212> TYPE: PRT
<213> ORGANISM: Artificial sequence
<220> FEATURE:
<223> OTHER INFORMATION: Synthetic construct

<400> SEQUENCE: 22

Leu Glu Val Leu Phe Gln Gly Pro
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: X
<222> LOCATION: (2)..(2)
<223> OTHER INFORMATION: X=any natural amino acid
<220> FEATURE:
<221> NAME/KEY: X
<222> LOCATION: (3)..(3)
<223> OTHER INFORMATION: X=any natural amino acid
<220> FEATURE:
<221> NAME/KEY: X
<222> LOCATION: (5)..(5)
<223> OTHER INFORMATION: X=any natural amino acid -continued

```
<220> FEATURE:
<221> NAME/KEY: X
<222> LOCATION: (7)..(7)
<223> OTHER INFORMATION: X=glycine or serine

<400> SEQUENCE: 23

Glu Xaa Xaa Tyr Xaa Gln Xaa
1               5
```

BACTERIAL COLICIN-IMMUNITY PROTEIN PROTEIN PURIFICATION SYSTEM

This application claims the benefit of U.S. Provisional Application No. 62/265,253, filed Dec. 9, 2015, which is hereby incorporated in its entirety by this reference.

BACKGROUND

Most commercially available purification tools are not useful for complex biological systems. Thus, protein purification can be an unpredictable, multi-step process. Protein purification of multi-subunit complexes and membrane proteins is particularly challenging as currently available approaches are time-consuming and fail to consistently provide samples of high quality, high yield and high purity (HHH).

SUMMARY

The present disclosure relates to purification of proteins, including multi-subunit complexes and membrane proteins. Provided herein are non-naturally occurring polypeptides and methods of using one or more of the polypeptides in purification methods. Also provided are related nucleic acids, vectors, genetically modified cells and affinity matrices.

More specifically, provided herein are polypeptides comprising a wild-type colicin-DNAse domain modified to comprise one or more mutations selected from the group consisting of a mutation that reduces DNAse activity, a mutation that decreases DNA binding and a mutation that increases thermostability of the polypeptide. The polypeptides optionally comprises a heterologous polypeptide that is operably linked to a cleavable polypeptide sequence, wherein the cleavable polypeptide sequence links the heterologous polypeptide with the colicin-DNAse domain.

Further provided are polypeptides comprising a colicin immunity protein, wherein the immunity protein comprises one or mutations that increase thermostability of the polypeptide.

The methods provided herein include a) transfecting in a cell culture medium a cell with a vector, wherein the vector comprises a nucleic acid encoding a first polypeptide under conditions in which the first polypeptide is expressed, wherein the first polypeptide is a polypeptide comprising a heterologous protein and a wild-type colicin-DNAse domain modified to comprise one or more mutations, wherein the heterologous protein and the modified colicin-DNAse domain are linked by a cleavable polypeptide sequence; b) harvesting the cell culture medium comprising the expressed first polypeptide; c) lysing the cells to obtain a supernatant comprising the expressed first polypeptide; d) contacting the supernatant with an affinity matrix comprising a substrate and a second polypeptide, wherein the second polypeptide comprises a colicin immunity protein with one or more mutations, e) washing the matrix to remove biological molecules non-specifically bound to the first expressed polypeptide and the matrix; and f) eluting the heterologous protein from the matrix, comprising enzymatically cleaving the heterologous protein from the first polypeptide.

Also provided are methods that include a) transfecting in cell culture medium a cell with a vector comprising a nucleic acid encoding a first polypeptide under conditions in which the first polypeptide is expressed, wherein the first polypeptide is a polypeptide comprising a heterologous protein and a wild-type colicin-DNAse domain modified to comprise one or more mutations, wherein the heterologous protein and the modified colicin-DNAse domain are linked by a cleavable polypeptide sequence; b) harvesting the cell culture medium comprising the expressed first polypeptide comprising the heterologous protein; c) contacting the harvested cell culture medium with an affinity matrix, wherein the affinity matrix comprises a substrate and a second polypeptide comprising a colicin immunity protein with one or more mutations; d) washing the matrix to remove biological molecules non-specifically bound to the expressed first polypeptide and the matrix; and e) eluting the heterologous protein from the matrix, comprising enzymatically cleaving the heterologous protein from the first polypeptide.

DESCRIPTION OF THE DRAWINGS

FIG. 5C shows an SDS gradient gel stained with Coomassie Blue. The M lane contains highly purified Biorad protein markers. Bands in the product lane (P) were excised and identified by mass spectroscopy. MukF, E, and B proteins were present in ratios that agree with the model on the left. However, the percentage of protein released from a second column in which 90% of the tags were cleaved at a Precision Protease cleavage site showed that, in this case, each complex has approximately 10 tags and all must be cleaved to release protein from the column.

DETAILED DESCRIPTION

Figure 1:
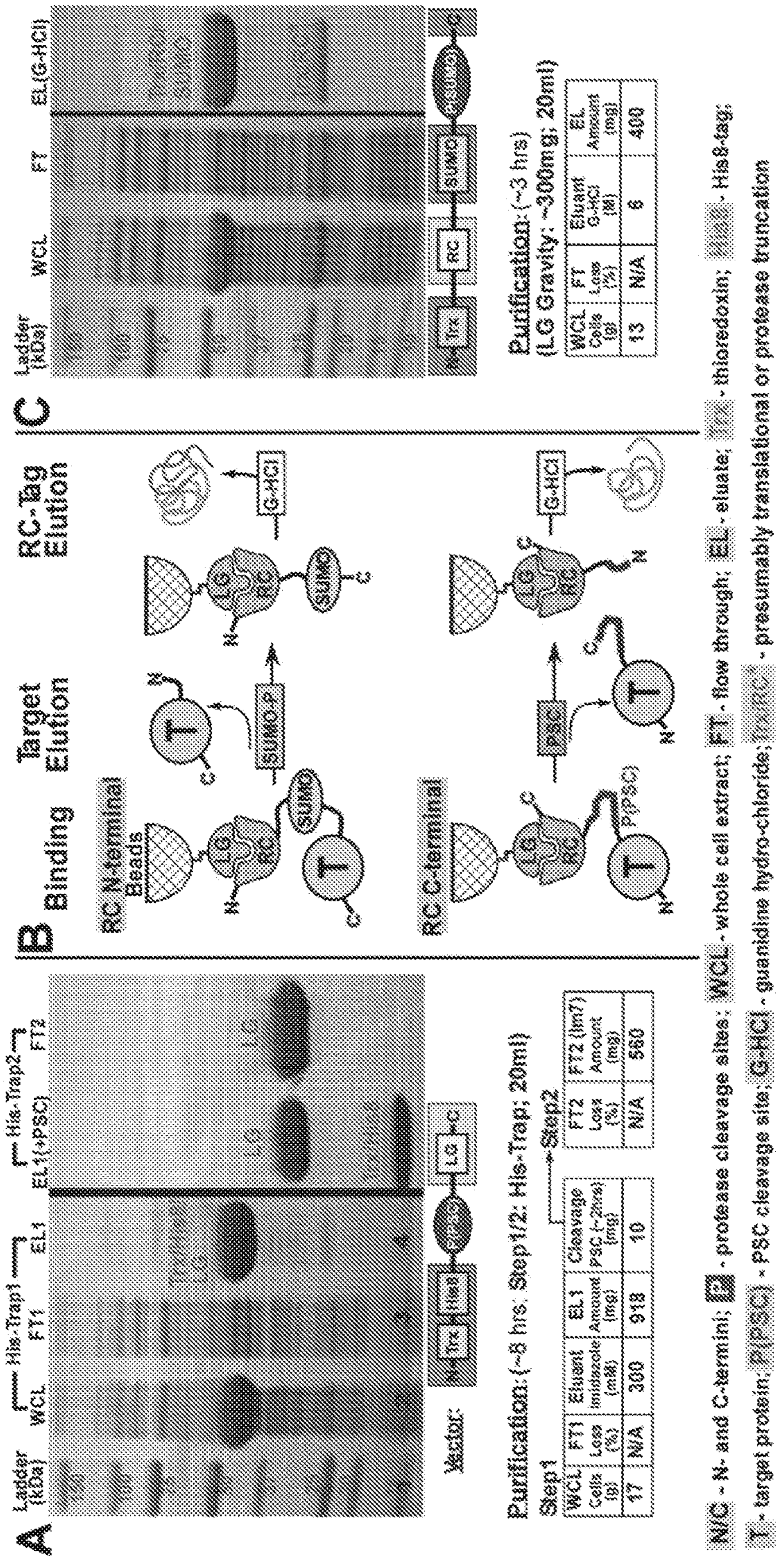
FIG. 1A shows the expression and purification of an immunity protein 7 (Im7 (LG)) that can be immobilized on a substrate and used in a single column protein purification system.
FIG. 1B shows a schematic of purification of tagged proteins using an Im7 column.
FIG. 1C shows the expression and purification a 45 kDa protein (Trx→RC→SUMO). RC-LG (Im7) receptor, CL7-tag.

Provided herein are compositions and purification methods for purifying any protein of interest, including multi-subunit complexes and membrane proteins, with high quality, high yield and high purity.

Protein purification is an essential, primary step in numerous studies, including proteomics and structural genomics. Most of these studies require three dimensional (3D) structures of the biological targets of interest, which can provide mechanistic insights into their functional properties. Given that obtaining a 3D structure often requires large quantities of highly purified proteins, purification tools that conform to the high yield, high purity and high activity rule (HHH rule) are necessary. Recently, studies of huge multi-subunit complexes (MSC) (transcription and translation machineries, for example) and membrane proteins (MPs) have emerged as a major focus of proteomics and its structural counterpart. Most commercially available purification tools are based on relatively small, monomeric proteins, and are not always useful for complex biological systems. Thus, protein purification has remained an unpredictable, time consuming, multi-step process, rather than a routine technical task.

MSCs and MPs are particularly challenging as the purification processes usually take more time, compared to functional and/or structural studies, and often cannot provide HHH-grade samples.

At present, there are no commercially available affinity systems that completely satisfy the HHH-rule. Most commercial columns provide modest yields of only a few milligrams due to a number of factors, including the use of a small amount of antibody, chitin, biotin, etc.; poor loading or slow binding; and high $k_{on}$ affinity (maltose binding protein (MBP) or glutathione synthase (GST)) of the active groups. The latter (MBP and GST) are also sensitive to high salt (over 200 mM NaCl) during loading, which can affect the final purity of the target. High salt particularly affects the nucleic acid (NA) binding protein complexes, which constitute a large pool of the biologically and industrially significant systems. In fact, the His-Trap ($Ni^{2+}$-based) approach is the only affinity approach with the H-yield capacity, and, for this reason, is the most popular purification technique among researchers in the field as well as in commercial applications.

However, this approach has a number of limitations that can affect the H-purity/H-activity components of the HHH-rule. For example, His-Trap columns are sensitive to reducing agents (β-ME, DTT, over 2-4 mM) and metal chelating agents (EDTA, over 1 mM). Further, column affinity is target-dependent, which requires adjustments of conditions for each new project. There can also be relatively high, non-specific affinity to DNA and cellular proteins, including many MPs. In addition, excessive amounts of $Ni^{2+}$ ions can affect conformation and the activity of a target protein. These restrictions typically result in only 60-80% purity for the over-expressed NA-binding MSCS (for example, a multi-subunit RNA polymerase) and 50-70% purity for the MP in a one-step purification through His-Trap columns. Consistently, the His-tag labelled naturally expressed proteins are substantially less pure due to a very poor signal-to-noise ratio. Since most of the other chromatography techniques are even less specific than His-trap, i.e. more target-dependent, the final H-purity is achieved through a combination of sequential purification steps using various commercial columns specific to each particular protein. Columns using anion/cation exchange, gel-filtration, heparin, DNA-agarose, etc. necessarily increase the time required for the entire process. Costs are also increased, as researchers must purchase and maintain a number of commercial chromatography systems, some of which can cost thousands of dollars. In summary, no chromatography system currently exists that allows for predictable and efficient one-step or multi-tag purification of complex MSC or MP targets using overexpression or natural expression protein preparation protocols.

The systems provided herein overcome the challenges of existing commercial products. Using the systems and methods described herein about 97-100% purity of most intact (untruncated) targets was obtained in a one-step purification. Importantly, large scale HHH-purifications of a number of the most challenging and biologically significant MSCs and MPs was successfully performed. The purification systems provided herein offer several advantages that provide significant improvements over commercially available chromatography systems. For example, these systems are not sensitive to high salt (tested up to 1.5M NaCl), metal-chelating and reducing agents, (for example, EDTA and β-mercaptoethanol, up to 20 mM tested) or detergents. Since detergents are unavoidable during purification of MPs, lack of sensitivity of detergents ensures binding affinity and purity. These systems are also fast binding systems, which allows for flow rates of about 5 ml/min. No loss in binding capacity was observed at these flow rates, which is essential for efficient purification of proteins from natural expression systems, where large lysate volumes are often used to achieve high yield. Ultra-high affinity was achieved with receptor/ligand (RC/LG) complexes (for example, CL7/Im7 complexes) that dissociate only in 6M GuHCl. Tests showed no detectable non-specific binding to all untagged cellular molecules. High affinity is crucial for successful purification of naturally expressed proteins, as they all possess poor signal-to-noise-ratio during purification. These systems are also high capacity systems that can be used to purify proteins of up to 80 kDa in size, in quantities of 400 mg or more using the 20 ml column. These systems can also employ multiple RC/LG complexes.

There are at least four known homologous (CL/Im) systems (see below), which, in spite of overall high structural and sequence similarity, possess essentially distinct binding sites and, therefore, demonstrate big losses in binding affinities (6 to 9 orders of magnitude in $K_m$, in particular, with $k_{off}$ approaching to 0) towards the non-cognate partners. This property of the (CL/Im) complexes allows for construction of at least four original, cross-resistant chromatography systems, in which distinct, modified CL DNAse domains may be used for tagging different subunits of MSC. The multi-tag approach can be used to avoid impurities related to possible translational/proteolytic truncations and/or to account for an imbalance in the expression levels of the individual subunits, which often occurs if the MSC is overexpressed, in particular, in a foreign cell or organism.

Polypeptides Comprising a Modified Colicin-DNAse Domain

Provided herein are polypeptides comprising a wild-type colicin-DNAse domain modified to comprise one or more mutations. The mutations are selected from the group consisting of a mutation that reduces DNAse activity, a mutation that decreases DNA binding and a mutation that increases thermostability of the polypeptide. Optionally, one or more mutations decrease DNAse activity, one or more mutations decrease DNA binding and/or one or more mutations increase thermostability. In any of the polypeptides provided herein, the wild-type colicin DNAse domain can be a wild-type colicin DNAse domain from any *Escherichia coli* colicin, including but not limited to, a wild-type colicin DNAse domain from colicin E7 (CL7), colicin E2 (CL2), colicin E7 (CL7) or colicin E9 (CL9). For example, the wild-type DNAse domain can be amino acids 446-573 of CL7, as set forth under GenBank Accession No. YP_009060493.1. A wild-type DNAse domain can also be an amino acid sequence from colicin E2 (CL2) (Genbank Accession No. YP_002221664.1), colicin E8 (CL8) (GenBank Accession No. YP_002993419.1) or colicin E9 (CL9) GenBank Accession No. YP_002533537.1) that corresponds to amino acids 446-573 of GenBank Accession No. YP_009060493.1. The wild-type DNAse domain can also be a wild-type DNAse domain comprising an N-terminal truncation of one, two, three, four or five amino acids.

A wild-type colicin DNAse domain binds to DNA and possesses DNAse enzymatic activity. Therefore, a mutation that reduces DNA binding activity and/or DNAse enzymatic activity is a mutation that reduces DNA binding activity and/or enzymatic activity of the wild-type colicin DNAse domain. The mutation can also reduce DNA binding activity and/or DNAse enzymatic activity of the polypeptide comprising the modified DNAse, domain, as compared to a polypeptide comprising a wild-type DNAse domain.

Optionally, in the polypeptides described throughout, one or more mutations are non-naturally occurring mutations.

The reduction or decrease in DNA binding activity refers to complete elimination or partial reduction. Thus, the reduction can be about a 10%, 20%, 30%, 40%, 50%, 60%, 70%, 80%, 90%, 100% reduction, or any percent reduction in between 10% and 100%, in DNA binding activity as compared to the DNA binding activity of the wild-type colicin DNAse domain. Similarly, the reduction or decrease in DNAse enzymatic activity can be partial or complete, including, for example, a 10%, 20%, 30%, 40%, 50%, 60%, 70%, 80%, 90%, 100%, or any percent reduction in between 10% and 100% reduction, in DNAse enzymatic activity as compared to the wild-type colicin DNAse domain. For example, and not to be limiting, the reduction or decrease in DNA binding activity can be a reduction of at least 10% DNA binding affinity and the reduction in enzymatic activity can be at least a 50% reduction in enzymatic activity.

The wild-type colicin-DNAse domain can be modified to comprise one or more mutations that increase the thermostability of the polypeptide as compared to the thermostability of the polypeptide in the absence of the modification, i.e., one or more mutations, in the wild-type DNAse domain. Optionally, for any of the polypeptides described throughout, an increase in thermostability results in a polypeptide that is stable at temperatures of about 60° C. or greater. For example, the polypeptide is stable at about 60° C., 70° C., 80° C. or greater, including, for example about 60-80° C.

In the polypeptides provided herein, a single mutation or a set of mutations can change one or more properties of the polypeptide simultaneously. For example, a mutation or set of mutations can reduce DNA binding and DNAse activity, a mutation or set of mutations can reduce DNA binding and increase thermostability of the polypeptide, a mutation or set of mutations can reduce DNAse enzymatic activity and increase thermostability of the polypeptide, or a mutation or set of mutations can reduce DNAse enzymatic activity, reduce DNA binding and increase thermostability.

As set forth above, polypeptides comprising a wild-type colicin-DNAse domain modified to comprise one or more mutations can comprise a wild-type CL7 DNAse domain (SEQ ID NO: 1), a wild-type CL2 DNAse domain (SEQ ID NO: 2), a wild-type CL8 DNAse domain (SEQ ID NO: 3) or a wild-type CL9 DNAse domain (SEQ ID NO: 4) with one or more mutations that reduces DNAse activity, that decreases DNA binding and/or increases thermostability of the polypeptide.

For example, and not to be limiting, the polypeptide can comprise SEQ ID NO: 1 with one or more mutations, wherein the one or more mutations are at one or more amino acids selected from the group consisting of R2, K4, K11, K45, K51, K52, H99, S105, H124 and H128. Optionally, the one or more mutations comprise one or more mutations selected from the group consisting of R2S/Z, K4E/Z, K11E/Z, K45E/Z, K51E, K52T/Z, H99N/Z, S105E/Z, H124N/Z and H128E/Z mutation in SEQ ID NO: 1, wherein Z is any natural amino acid except for glycine (G), cysteine (C), proline (P), lysine (K) or arginine (R). Optionally, the mutations comprise R2S, K4E, K11E, K45E, K51E, K52T, H99N, S105E, H124N and H128E mutations in SEQ ID NO: 1.

In another example, the polypeptide can comprise SEQ ID NO: 2 with one or more mutations, wherein the one or more mutations are at one or more amino acids selected from the group consisting of R2, K4, K11, K45, K51, K52, H99, S105, H124 and H128. Optionally, one or more amino acids at positions, 2, 4, 11, 45, 51, 52, 99, 105, 124 and 128 can be replaced with any natural amino acid except for glycine (G), cysteine (C), proline (P), lysine (K) or arginine (R). Optionally, the one or more mutations comprise one or more mutations selected from the group consisting of R2S, K4E, K11E, K45E, K51E, K52T, H99N, S105E, H124N and H128E. Optionally, the mutations comprise a R2S, a K4E, a K11E, a K45E, a K51E, a K52T, a H99N, a S105E, a H124N and a H128E mutation in SEQ ID NO: 2.

In another example, the polypeptide can comprise SEQ ID NO: 3 with one or more mutations, wherein the one or more mutations are at one or more amino acids selected from the group consisting of R2, K4, K11, K45, R51, K52, H99, S105, H124 and H128. Optionally, one or more amino acids at positions, 2, 4, 11, 45, 51, 52, 99, 105, 124 and 128 can be replaced with any natural amino acid except for glycine (G), cysteine (C), proline (P), lysine (K) or arginine (R). Optionally, the one or more mutations comprise one or more mutations selected from the group consisting of R2S, K4E, K11E, K45E, R51E, K52T, H99N, S105E, H124N and H128E. Optionally, the mutations comprise R2S, K4E, K11E, K45E, R51E, K52T, H99N, S105E, H124N and H128E mutations in SEQ ID NO: 3.

In another example, the polypeptide can comprise SEQ ID NO: 4 with one or more mutations, wherein the one or more mutations are at one or more amino acids selected from the group consisting of R2, K4, K11, K45, K51, A52, H99, S105, H124 and H128. Optionally, one or more amino acids at positions, 2, 4, 11, 45, 51, 52, 99, 105, 124 and 128 can be replaced with any natural amino acid except for glycine (G), cysteine (C), proline (P), lysine (K) or arginine (R). Optionally, the one or more mutations comprise one or more mutations selected from the group consisting of R2S, a K4E, a K11E, a K45E, a K51E, a A52T, a H99N, a S105E, H124N and H128E. Optionally, the mutations comprise R2S, K4E, K11E, K45E, K51E, A52T, H99N, S105E, H124N and H128E mutations in SEQ ID NO: 4.

Polypeptides that are at least about 80%, 85%, 90%, 95% or 99% identical to SEQ ID NO: 1, SEQ ID NO: 2, SEQ ID NO: 3 or SEQ ID NO: 4 can also be modified as set forth herein. For example, a polypeptide comprising an amino acid sequence that is at least about 80%, 85%, 90%, 95%, or 99% identical to SEQ ID NO: 1, SEQ ID NO: 2, SEQ ID NO: 3 or SEQ ID NO: 4 comprising one or more mutations at one or more amino acids selected from the amino acids at positions 2, 4, 11, 45, 51, 52, 99, 105, 124 and 128 are provided herein. For example, a polypeptide comprising an amino acid sequence that is at least about 80%, 85%, 90%, 95%, or 99% identical to SEQ ID NO: 1 comprising one or more mutations at one or more amino acids selected from the group consisting of R2, K4, K11, K45, K51, K52, H99, S105, H124 and H128 is provided herein. A polypeptide comprising an amino acid sequence that is at least about 80%, 85%, 90%, 95%, or 99% identical to SEQ ID NO: 2 comprising one or more mutations at one or more amino acids selected from the group consisting of R2, K4, K11, K45, K51, K52, H99, S105, H124 and H128 is also provided herein. Further provided is a polypeptide comprising an amino acid sequence that is at least about 80%, 85%, 90%, 95%, or 99% identical to SEQ ID NO: 3 comprising one or more mutations at one or more amino acids selected from the group consisting of R2, K4, K11, K45, R51, K52, H99, S105, H124 and H128. Also provided is a polypeptide comprising an amino acid sequence that is at least about 80%, 85%, 90%, 95%, or 99% identical to SEQ ID NO: 4 comprising one or more mutations at one or more amino acids selected from the group consisting of R2, K4, K11, K45, K51, A52, H99, S105, H124 and H128.

Those of skill in the art readily understand how to determine the identity of two polypeptides or nucleic acids. For example, the identity can be calculated after aligning the two sequences so that the identity is at its highest level. Another way of calculating identity can be performed by published algorithms. Optimal alignment of sequences for comparison can be conducted using the algorithm of Smith and Waterman *Adv. Appl. Math.* 2: 482 (1981), by the alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/bl2seq/bl2.html), or by inspection.

The polypeptides comprising a wild-type colicin-DNAse domain modified to comprise one or more mutations, can further comprise a cleavable polypeptide sequence in operable linkage with the colicin-DNAse domain, wherein the cleavable polypeptide sequence is at least about fifty amino acids in length. For example, the cleavable polypeptide sequence can be about 10 to about 75 amino acids in length, or greater. For example, the cleavable polypeptide sequence can be about 10, 15, 20, 25, 30, 35, 40, 45, 50, 55, 60, 65, 70, 75 amino acids or greater. Optionally, the cleavable polypeptide sequence comprises SEQ ID NO: 5. Optionally the cleavable polypeptide sequence is resistant to cellular proteases. The cleavable polypeptide sequence can be operably linked to the N-terminus or the C-terminus of the modified colicin-DNAse domain and can be used to link the modified colicin-DNAse domain with other polypeptide sequences, including a protein of interest, for example, a heterologous protein.

Optionally, the cleavable polypeptide sequence comprises a protease cleavage site and a histidine tag sequence. Examples of protease cleavage sites include, but are not limited to, a PreScission protease cleavage site (LEVLFQGP)(SEQ ID NO: 22) that is cleaved by PreScission protease (GE Life Sciences, Pittsburgh, Pa.), a SUMO domain that is cleaved by SUMO protease or a TEV protease cleavage site (for example, EXXYXQG/S)(SEQ ID NO: 23), wherein X is any natural amino acid). The histidine tag sequence can comprise about four to about ten histidine residues in succession. For example, the histidine tag sequence can be four, five, six, seven, eight, nine or ten consecutive histidine residues.

Optionally, the polypeptides comprising a wild-type colicin-DNAse domain are modified to comprise one or more mutations and include a cleavable polypeptide sequence in operable linkage with the colicin-DNAse domain. For example, the polypeptide comprises SEQ ID NO: 6 (a modified CL7 DNAse domain in operable linkage with a cleavable polypeptide sequence), SEQ ID NO: 7 (a modified CL2 DNAse domain in operable linkage with a cleavable polypeptide sequence), SEQ ID NO: 8 (a modified CL8 DNAse domain in operable linkage with a cleavable polypeptide sequence) or SEQ ID NO: 9 (a modified CL9 DNAse domain in operable linkage with a cleavable polypeptide sequence).

Optionally, the polypeptides comprising a wild-type colicin-DNAse domain modified to comprise one or more mutations and a cleavable polypeptide sequence in operable linkage with the colicin-DNAse domain can further comprise a heterologous protein operably linked to the cleavable polypeptide sequence, wherein the cleavable polypeptide sequence links the heterologous polypeptide with the colicin-DNAse domain. In the polypeptides comprising a heterologous protein, the cleavable polypeptide sequence can link the modified colicin-DNAse domain to the N-terminus of the heterologous protein or to the C-terminus of the heterologous protein.

As used throughout, a heterologous protein is a protein that is not naturally associated with a wild-type colicin-DNAse domain or portion thereof. Generally, the heterologous protein is not normally produced by a cell in which the nucleic acid encoding a polypeptide comprising the heterologous protein is introduced. However, the heterologous protein can be naturally produced by a cell in which a nucleic acid encoding a polypeptide comprising the heterologous protein is introduced, such that the protein is both produced naturally and recombinantly by the cell.

The heterologous protein can be a eukaryotic or prokaryotic protein. The heterologous protein can be a full-length protein or a fragment thereof. The heterologous protein can be from a pathogen, such as, a parasite, a fungus, a bacteria, a virus or a prion. The heterologous protein can be a cytoplasmic protein, a membrane protein or a multi-subunit protein. The heterologous protein can be an enzyme, a hormone, a growth factor, a cytokine, an antibody or a portion thereof, a structural protein or a receptor, to name a few. The heterologous protein can also be a vaccine protein or a protein that is specifically expressed in a disease state, for example, a cancer-specific protein.

Polypeptides Comprising a Modified Colicin Immunity Protein

Further provided herein are polypeptides comprising a colicin immunity protein, wherein the immunity protein comprises one or mutations that increase thermostability of the polypeptide. Optionally, the colicin immunity protein is Im7 with one or more mutations. For example, the polypeptide can comprise SEQ ID NO: 10 with one or more mutations. Optionally, the polypeptide comprises SEQ ID NO: 10 with one or more mutations at one or more amino acid positions selected from the group consisting of L3, K4, A13, Q17, K20, E21, K24, V33, V36, L37, K43, K70, K73, A77 and K81. Optionally, the one or more mutations are selected from the group consisting of L3F, K4R, A13E, Q17R, K20R, E21G, K24R, V33R, V36W, L37M, K43E, K70E, K73R, A77E and K81R in SEQ ID NO: 10. Optionally, the mutations comprise L3F, K4R, A13E, Q17R, K20R, E21G, K24R, V33R, V36W, L37M, K43E, K70E, K73R, A77E and K81R in SEQ ID NO: 10. Optionally, the colicin immunity protein is Im9 with one or more mutations. For example, the polypeptide can comprise SEQ ID NO: 11 with one or more mutations.

Optionally, the polypeptide comprises SEQ ID NO: 11 with one or more mutations at one or more amino acid positions selected from the group consisting of L3, K4, A5, A13, Q17, T21, K35, L36, M43, K57, Q72, A76, K80 and K84. Optionally, the one or more mutations are selected from the group consisting of L3F, K4R, A5D, A13E, Q17R, T21S, K35W, L36M, M43I, K57R, Q72R, A76E, K80R and K84Q in SEQ ID NO: 11. Optionally, the mutations comprise L3F, K4R, A5D, A13E, Q17R, T21S, K35W, L36M, M43I, K57R, Q72R, A76E, K80R and K84Q in SEQ ID NO: 11.

The polypeptides comprising a modified colicin immunity protein can further comprise a cleavable polypeptide sequence in operable linkage with the colicin immunity protein domain. The cleavable polypeptide sequence is described above. The cleavable polypeptide sequence can be operably linked to the N-terminus or the C-terminus of the modified immunity protein. Optionally, the cleavable polypeptide sequence comprises a protease cleavage site and a histidine tag sequence. Examples of protease cleavage sites and histidine tag sequences are described above.

Optionally, the polypeptide further comprises a polypeptide sequence comprising a thioredoxin tag, wherein the cleavable polypeptide sequence links the thioredoxin tag and the colicin immunity protein. Optionally, the polypeptide further comprises amino acid sequences comprising a cysteine-containing coiled-coil, wherein the amino acid sequences flank the colicin immunity protein. By flanking is meant immediately adjacent on each end of the colicin immunity protein or juxtaposed in close proximity. Optionally, the polypeptide comprises SEQ ID NO: 12 or SEQ ID NO: 13.

The polypeptides comprising a modified colicin immunity protein and/or the polpeptides comprising a DNAse domain can be immobilized on a solid support. For example, and not to be limiting, the solid support can be a magnetic bead, an agarose-based resin or an agarose bead. In other examples, the solid support comprises non-agarose chromatography media, monoliths or nanoparticles. For example, the chromatography media can be, e.g., methacrylate, cellulose, or glass. In other examples, the nanoparticles are gold nanoparticles or magnetic nanoparticles.

Further provided is an affinity matrix comprising a substrate and one or more of the polypeptides provided herein, wherein the one or more polypeptides are conjugated or crosslinked to the substrate. For example, one or more polypeptides, or a plurality of polypeptides comprising a modified immunity protein, can be conjugated to the substrate. The substrate can, for example, a magnetic bead, an agarose-based resin or an agarose bead.

Purification Systems

The polypeptides comprising a modified colicin DNAse domain and the polypeptides comprising a modified immunity protein form a high affinity complex with a binding affinity that approaches the binding affinities of a covalent bond ($K_m$~$10^{-14}$-$10^{-7}$). For example, a modified CL7 DNAse domain specifically binds to a modified Im7 protein. In another example, a modified CL9 DNAse domain specifically binds to an Im9 protein.

The purification methods provided herein rely on this interaction to efficiently purify heterologous proteins. When tagged heterologous proteins i.e., heterologous proteins linked by a cleavable polypeptide to polypeptides comprising a modified colicin DNAse domain, are contacted with polypeptides comprising a modified immunity protein, the modified colicin DNAse domain binds to the polypeptides comprising the modified immunity protein. Once bound to the polypeptides comprising the modified immunity protein, via the modified colicin DNAse domain, the heterologous protein can be cleaved from the complex by enzymatically cleaving the heterologous protein from the polypeptide comprising the modified colicin DNAse domain. Therefore, systems comprising a polypeptide comprising a modified colicin DNAse domain that specifically binds to polypeptides comprising a modified immunity protein are provided herein.

Nucleic Acids

Further provided is a nucleic acid encoding any one of the polypeptides provided herein. Modifications in the amino acid sequences in the polypeptides provided herein can arise as allelic variations (e.g., due to genetic polymorphism), may arise due to environmental influence (e.g., due to exposure to ultraviolet radiation), or other human intervention (e.g., by mutagenesis of cloned DNA sequences), such as induced point, deletion, insertion, and substitution mutants. The mutations are not limited to the mutations described above, as additional modifications can be made. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to about 6 residues are deleted at any one site within the protein molecule. Amino acid substitutions are typically of single residues, but can occur at a number of different locations at once; insertions usually will be on the order of about from 1 to about 10 amino acid residues; and deletions will range from about 1 to about 30 residues. Deletions or insertions preferably are made in adjacent pairs, i.e., a deletion of 2 residues or insertion of 2 residues. Substitutions, deletions, insertions or any combination thereof can be combined to arrive at a final construct. The mutations may or may not place the sequence out of reading frame and may or may not create complementary regions that could produce secondary mRNA structure. Substitutional modifications are those in which at least one residue has been removed and a different residue inserted in its place.

Modifications, including the specific amino acid substitutions disclosed herein, are made by known methods. By way of example, modifications are made by site specific mutagenesis of nucleotides in the DNA encoding the polypeptide, thereby producing a DNA encoding the modification, and thereafter expressing the DNA in recombinant cell culture to produce the encoded polypeptides. Techniques for making substitution mutations at predetermined sites in DNA having a known sequence are well known, for example M13 primer mutagenesis and PCR mutagenesis.

The amino acids in the polypeptides described herein can be any of the 20 naturally occurring amino acids, D-stereoisomers of the naturally occurring amino acids, unnatural amino acids and chemically modified amino acids. Unnatural amino acids (that is, those that are not naturally found in proteins) are also known in the art, as set forth in, for example, Zhang et al. "Protein engineering with unnatural amino acids," Curr. Opin. Struct. Biol. 23(4): 581-587 (2013); Xie et al. "Adding amino acids to the genetic repertoire," 9(6): 548-54 (2005)); and all references cited therein. B and γ amino acids are known in the art and are also contemplated herein as unnatural amino acids.

As used herein, a chemically modified amino acid refers to an amino acid whose side chain has been chemically modified. For example, a side chain can be modified to comprise a signaling moiety, such as a fluorophore or a radiolabel. A side chain can also be modified to comprise a new functional group, such as a thiol, carboxylic acid, or amino group. Post-translationally modified amino acids are also included in the definition of chemically modified amino acids.

Also contemplated are conservative amino acid substitutions. By way of example, conservative amino acid substitutions can be made in one or more of the amino acid residues of any of the polypeptides provided herein. One of skill in the art would know that a conservative substitution is the replacement of one amino acid residue with another that is biologically and/or chemically similar. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

By way of example, when an arginine to serine is mentioned, also contemplated is a conservative substitution for the serine (e.g., threonine). Nonconservative substitutions, for example, substituting a proline with glycine are also contemplated.

Those of skill in the art readily understand how to determine the identity of two polypeptides or nucleic acids. For example, the identity can be calculated after aligning the two sequences so that the identity is at its highest level. Another way of calculating identity can be performed by published algorithms. Optimal alignment of sequences for comparison can be conducted using the algorithm of Smith and Waterman, *Adv. Appl. Math.* 2: 482 (1981); by the alignment algorithm of Needleman and Wunsch, *J. Mol. Biol.* 48: 443 (1970); by the search for similarity method of Pearson and Lipman, *Proc. Natl. Acad. Sci. U.S.A.* 85: 2444 (1988); by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information (http://www.ncbi.nlm.nih.gov/blast/bl2seq/bl2.html); or by inspection.

The same types of identity can be obtained for nucleic acids by, for example, the algorithms disclosed in Zuker, *Science* 244:48-52, 1989; Jaeger et al. *Proc. Natl. Acad. Sci. USA* 86:7706-7710, 1989; Jaeger et al. *Methods Enzymol.* 183:281-306, 1989 that are herein incorporated by this reference for at least material related to nucleic acid alignment. It is understood that any of the methods typically can be used and that, in certain instances, the results of these various methods may differ, but the skilled artisan understands if identity is found with at least one of these methods, the sequences would be said to have the stated identity.

For example, as used herein, a sequence recited as having a particular percent identity to another sequence refers to sequences that have the recited identity as calculated by any one or more of the calculation methods described above. For example, a first sequence has 80 percent identity, as defined herein, to a second sequence if the first sequence is calculated to have 80 percent identity to the second sequence using the Zuker calculation method even if the first sequence does not have 80 percent identity to the second sequence as calculated by any of the other calculation methods. As yet another example, a first sequence has 80 percent identity, as defined herein, to a second sequence if the first sequence is calculated to have 80 percent identity to the second sequence using each of calculation methods (although, in practice, the different calculation methods will often result in different calculated identity percentages).

Vectors

Further provided is a vector comprising a nucleic acid set forth herein. The vector can direct the in vivo or in vitro synthesis of any of the polypeptides described herein. The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene (See generally, Sambrook et al. Molecular Cloning: A Laboratory Manual, $4^{th}$ ed., Cold Spring Harbor Laboratory Press, Cold Spring Harbor, 2012). The vector, for example, can be a plasmid. The vectors can contain genes conferring hygromycin resistance, ampicillin resistance, gentamicin resistance, neomycin resistance or other genes or phenotypes suitable for use as selectable markers, or methotrexate resistance for gene amplification.

There are numerous other *E. coli* expression vectors known to one of ordinary skill in the art, which are useful for the expression of the nucleic acid insert. Other microbial hosts suitable for use include bacilli, such as *Bacillus subtilis*, and other enterobacteriaceae, such as *Salmonella, Senatia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. Additionally, yeast expression can be used. Provided herein is a nucleic acid encoding a polypeptide of the present invention, wherein the nucleic acid can be expressed by a yeast cell. More specifically, the nucleic acid can be expressed by *Pichia pastoris* or *S. cerevisiae.*

Mammalian cells also permit the expression of proteins in an environment that favors important post-translational modifications such as folding and cysteine pairing, addition of complex carbohydrate structures, and secretion of active protein. Vectors useful for the expression of active proteins in mammalian cells are known in the art and can contain genes conferring hygromycin resistance, genticin or G418 resistance, or other genes or phenotypes suitable for use as selectable markers, or methotrexate resistance for gene amplification. A number of suitable host cell lines capable of secreting intact human proteins have been developed in the art, and include the CHO cell lines, HeLa cells, COS-7 cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc.

The expression vectors described herein can also include the nucleic acids as described herein and under the control of an inducible promoter such as the tetracycline inducible promoter or a glucocorticoid inducible promoter. The nucleic acids of the present invention can also be under the control of a tissue-specific promoter to promote expression of the nucleic acid in specific cells, tissues or organs. Any regulatable promoter, such as a metallothionein promoter, a heat-shock promoter, and other regulatable promoters, of which many examples are well known in the art are also contemplated. Furthermore, a Cre-loxP inducible system can also be used, as well as a Flp recombinase inducible promoter system, both of which are known in the art.

Insect cells also permit the expression of the polypeptides. Recombinant proteins produced in insect cells with baculovirus vectors undergo post-translational modifications similar to that of wild-type mammalian proteins.

Cells

Also provided is a cell comprising a vector provided herein, wherein the cell is a suitable host cell for the expression of a nucleic acid encoding any of the polypeptides contemplated herein. The host cell can be a prokaryotic cell, including, for example, a bacterial cell. More particularly, the bacterial cell can be an *E. coli* cell. Alternatively, the cell can be a eukaryotic cell, including, for example, a Chinese hamster ovary (CHO) cell, a COS-7 cell, a HELA cell, an avian cell, a myeloma cell, a *Pichia* cell, an insect cell or a plant cell. A number of other suitable host cell lines have been developed and include myeloma cell lines, fibroblast cell lines, and a variety of tumor cell lines such as melanoma cell lines. The vectors containing the nucleic acid segments of interest can be transferred into the host cell by well-known methods, which vary depending on the type of cellular host. For example. calcium chloride transformation is commonly utilized for prokaryotic cells, whereas calcium phosphate, DEAE dextran, Lipofectamine, or lipofectin mediated transfection, electroporation or any method now known or identified in the future can be used for other eukaryotic cellular hosts.

Compositions and Methods for Purification

Also provided herein is a method of purifying a heterologous protein comprising a) transfecting in a cell culture medium a cell with a vector, wherein the vector comprises a nucleic acid encoding a first polypeptide under conditions in which the first polypeptide is expressed, wherein the first polypeptide is a polypeptide comprising a heterologous protein and a wild-type colicin-DNAse domain modified to comprise one or more mutations, wherein the heterologous protein and the modified colicin-DNAse domain are linked by a cleavable polypeptide sequence; b) harvesting the cell culture medium comprising the expressed first polypeptide; c) lysing the cells to obtain a supernatant comprising the expressed first polypeptide; d) contacting the supernatant with an affinity matrix comprising a substrate and a second polypeptide, wherein the second polypeptide comprises a colicin immunity protein with one or more mutations, e) washing the matrix to remove biological molecules non-specifically bound to the first expressed polypeptide and the matrix; and f) eluting the heterologous protein from the matrix, comprising enzymatically cleaving the heterologous protein from the first polypeptide.

Also provided is a method of purifying a heterologous protein comprising a) transfecting in cell culture medium a cell with a vector comprising a nucleic acid encoding a first polypeptide under conditions in which the first polypeptide is expressed, wherein the first polypeptide is a polypeptide comprising a heterologous protein and a wild-type colicin-DNAse domain modified to comprise one or more mutations, wherein the heterologous protein and the modified colicin-DNAse domain are linked by a cleavable polypeptide sequence; b) harvesting the cell culture medium comprising the expressed first polypeptide comprising the heterologous protein; c) contacting the harvested cell culture medium with an affinity matrix, wherein the affinity matrix comprises a substrate and a second polypeptide comprising a colicin immunity protein with one or more mutations; d) washing the matrix to remove biological molecules non-specifically bound to the expressed first polypeptide and the matrix; e) eluting the heterologous protein from the matrix, comprising enzymatically cleaving the heterologous protein from the first polypeptide.

The cells that express the heterologous protein can be any cell that is suitable for the expression of the polypeptide comprising the heterologous protein, including any cell described herein. Heterologous proteins can also be purified from cells comprising a genome that has been genetically modified to express the polypeptide comprising the heterologous protein, i.e., a fusion protein comprising a modified colicin DNAse domain, a cleavable polypeptide linker and a heterologous protein.

Optionally, the purification methods can further comprise, after enzymatic cleavage of the heterologous polypeptide, eluting the first polypeptide, i.e., the modified colicin DNAse tag that is bound to the second polypeptide, i.e., the polypeptide comprising the modified colicin immunity protein, on the matrix and reactivating the matrix comprising the second polypeptide. For example, and not to be limiting, the first polypeptide can be eluted with 6M guanidine hydrochloride (G-HCl). The matrix comprising the second polypeptide, for example, an Im7 column can be reactivated by a one hour gradient refolding of Im7 during which where G-HCl is replaced with an appropriate buffer, as set forth in the Examples.

In the methods of purifying a heterologous protein, the cell culture medium comprising the expressed first polypeptide can be contacted with an affinity matrix comprising a second polypeptide comprising a colicin immunity protein under conditions that include salt concentrations of about 0.5M to about 2.0M. For example, the salt concentration can be about 0.5M, 0.6M, 0.7M, 0.8M, 0.9M, 1.0M, 1.1M, 1.2M, 1.3M, 1.4M, 1.5M or any concentration in between these concentrations. Salts such as NaCl and KCl can be used in any of the methods provided herein. Other salts are available to those of skill in the art. Based on the teachings of the specification, one of skill in the art would know how to select and use a salt and appropriate concentrations for purification of a protein of interest.

In the methods of purifying a heterologous protein, the affinity matrix can be any material to which a ligand, for example, a colicin immunity protein described herein, can be attached. The affinity matrix can include a solid support to which the colicin immunity protein can be attached. Examples of solid supports include, but are not limited to, beads, chips, capillaries or a filter comprising synthetic polymers (for example, polyvinyl alcohol, polyhydroxyalkyl acrylates, polyhydroxyalkyl methacrylates, polyacrylamides, polymethacrylamides), agarose, cellulose, dextran, polyacrylamide, latex or controlled pore glass.

In the methods of purifying a heterologous protein, the colicin immunity protein can be, for example, Im7 or Im9. Optionally, the polypeptide comprises SEQ ID NO: 10 with one or more mutations as described above.

Optionally, the colicin immunity protein is Im9 with one or more mutations as described above. For example, the polypeptide can comprise SEQ ID NO: 11 with one or more mutations as described above.

The polypeptides comprising a modified colicin immunity protein can further comprise a cleavable polypeptide sequence in operable linkage with the colicin immunity protein domain, wherein the cleavable polypeptide sequence is as described above. The cleavable polypeptide sequence can be operably linked to the N-terminus or the C-terminus of the modified immunity protein. Optionally, the cleavable polypeptide sequence comprises a protease cleavage site and a histidine tag sequence. Examples of protease cleavage sites and histidine tag sequences are described above.

Optionally, the polypeptide further comprises a polypeptide sequence comprising a thioredoxin tag, wherein the cleavable polypeptide sequence links the thioredoxin tag and the colicin immunity protein. Optionally, the polypeptide further comprises amino acid sequences comprising a cysteine-containing coiled-coil, wherein the amino acid sequences flank the colicin immunity protein. Optionally, the polypeptide as used in the methods comprises SEQ ID NO: 12 or SEQ ID NO: 13.

Genetic Modification of Cells

Provided herein is a method of genetically modifying the genome of a cell to encode a chimeric polypeptide comprising a protein of interest and a modified colicin DNAse domain comprising: a) introducing into a population of cells (i) a guide RNA (gRNA) comprising a first nucleotide sequence that hybridizes to a target DNA in the genome of the cell, wherein the target DNA is the coding sequence or a nucleic acid sequence adjacent to the N-terminus or the C-terminus of the coding sequence for the protein of interest, and a second nucleotide sequence that interacts with a site-directed nuclease; (ii) a recombinant site-directed nuclease, wherein the site-directed nuclease comprises an RNA-binding portion that interacts with the second nucleotide sequence of the gRNA, wherein the site-directed nuclease specifically binds and cleaves the target DNA to create a double-stranded break before the N-terminus or after the C-terminus of the coding sequence for the protein; and (iii) a donor nucleic acid sequence comprising (i) a third nucleotide sequence that encodes the polypeptide of any of claims 16-19 and (ii) a fourth nucleotide sequence that hybridizes to a genomic sequence flanking the double stranded break in the target DNA, wherein (a)(i), (a)(ii) and (a)(iii) are introduced into the cells under conditions that allow homology-directed repair and integration of the third nucleotide sequence into the target DNA to form a genetically modified cell.

Methods for site-specific modification of a target DNA in a population of cells are known in the art. For example, the nuclease, guide RNA and donor nucleic acid sequence can be introduced into the cells under conditions that allow homology-directed repair (HDR) and integration of a donor nucleotide, for example, a ssODN or double stranded nucleotide sequence into the target DNA. The nuclease, guide RNA and donor nucleic acid sequence can be introduced into the cell via nucleoporation. Methods for nucleoporation are known in the art. See, for example, Maasho et al. "Efficient gene transfer into the human natural killer cell line, NKL, using the amaxa nucleofection system," *Journal of Immunological Methods* 284(1-2): 133-140 (2004); and Aluigi et al. "Nucleofection is an efficient non-viral transduction technique for human bone marrow derived mesenchymal stem cells," Stem Cells 24(2): 454-461 (2006)), both of which are incorporated herein in their entireties by this reference.

Optionally, in the methods of genetically modifying cells using a site-directed nuclease, (a)(i), (a)(ii), and (a)(iiii) are introduced into the population of cells by transfecting the cells with one or more vectors comprising the guide RNA, the nucleic acid sequence encoding the nuclease, and the donor nucleic acid. Optionally, the nuclease is Cas9. Methods for site-specific modification using CRISPR/Cas9 systems are known in the art (See, for example, Smith et al. "Efficient and allele-specific genome editing of disease loci in human iPSCs," *Mol. Ther.* 23(3): 570-7 (2015); and Jo et al. "CRISPR/Cas9 system as an innovative genetic engineering tool: Enhancements in sequence specificity and delivery methods," *Biochim Biophys Acta* 1856(2): 234-243 (2015)).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed, that while specific reference of each various individual and collective combinations and permutations of these compounds may not be explicitly disclosed, each is specifically contemplated and described herein. For example, it is understood that when combinations, subsets, interactions, purification conditions etc. are disclosed in Examples I and II, that while specific reference of each various individual and collective combinations and permutations of these combinations, subsets, interactions, purification conditions may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

Example I

Described herein are purification systems that employ a synthetic protein tag (a polypeptide comprising a modified colicin DNAse domain) that has extraordinary affinity for a single receptor protein (a colicin immunity protein). Two cross-resistant, affinity purification systems were developed using genetic modifications of ultra-high affinity homologous receptor/ligand (RC/LG) complexes. The affinity of these complexes (km~$10^{-14}$-$10^{-17}$ M) approaches that of a covalent bond, which makes this purification system a powerful and unique tool for purifying large proteins, in significant quantities, in a single step. With the systems provided herein, it is possible to isolate cellular components with a level of purity that allows mass spectroscopy analysis of the contents.

Preparation of Colicin Immunity Protein 7 (Im7) Immobilization Unit (IU)

Expression

*E. coli*, BL21 DE cells transformed with a vector comprising a nucleic acid encoding genetically modified Im7 were used. The cells were grown in about 1-2 liters of TB medium, at 37° C., to an OD of about 0.8-0.9. Then, the temperature was decreased to 18-20° C. and expression was induced with 0.1-1 mM IPTG and the cells were allowed to grow overnight (20-24 hrs). The culture was centrifuged for about 20 mins. at 6,000 g and the cell pellet was stored at −80° C.

Purification

All procedures were carried out at 4° C. The cell pellet was suspended in lysis buffer (Buf-A; 0.5M NaCl 20 mM Tris pH 8, 5% Glycerol, 0.1 mM PMSF—added each 30 min) with a ratio of 10 ml Buf-A for 1 g cells and sonicated for about 30-40 mins, for about 100 ml of lysate. The lysate was heat sonicated at 70° C. for 45-50 min., and then centrifuged at 40,000 g for about 20 mins. Finally, the supernatant (SN) was filtered through a 45 μm filter. The filtered SN was loaded on the His-trap column (20 ml, GE Healthcare) at a flow rate of 5 ml/min with addition of 10-20 mM imidazole (IMZ). The column was washed with Buf-A in the presence of 30-50 mM IMZ and then the sample was eluted with 300 mM IMZ (FIG. 1A). The eluted sample was dialyzed against Buf-A with addition of His-tagged SUMO Protease (SUMO-P; ~1 mg SUMO-P for 30-50 mg Im7 IU) for 4-6 hrs (or overnight). Then, the His-trap step was repeated, and the cleaved and ready to use Im7 IU was collected in a flow-through (FT) fraction (FIG. 1A).

Immobilization of Im7 on Beads

SulfoLink coupling resin from Thermo Fisher was used according to the protocol provided by Thermo Fisher, as described below, (with scale up) (FIG. 1B) to covalently link the Im7 construct to agarose beads.

Protocol for Immobilization (Thermo Fisher)

The peptide or protein to be immobilized must have free (reduced) sulfhydryls. Ellman's Reagent (Thermo Fisher, Product No. 22582) was used to determine if the peptide or protein contains free sulfhydryls. To make sulfhydryl groups available for coupling, disulfide bonds were cleaved with a reducing agent). If a sulfhydryl-containing reducing agent is used, desalting or dialysis is performed to remove the reducing agent before immobilization.

For peptide samples, Tris(2-carboxyethyl)phosphine (TCEP, Product No. 77720) efficiently reduces peptides but does not interfere with iodoacetyl coupling, requiring no removal of excess reagent before immobilization. TCEP is stable in aqueous solution and selectively reduces disulfide bonds. 0.1-1 mg of peptide are dissolved or diluted in 2 mL of Coupling Buffer and add TCEP to a final concentration of 25 mM TCEP.

For protein samples, 1-10 mg of protein are dissolved or diluted with 1 mL of buffer (0.1M sodium phosphate, 5 mM EDTA-Na; pH 6.0). The protein solution is added to 6 mg of 2-MEA (50 mM). The mixture is incubated at 37° C. for 1.5 hours. 2-MEA is removed by performing two passes through a Thermo Scientific Zeba Spin Desalting Column (see Related Thermo Scientific Products) using the Coupling Buffer.

Procedure for Immobilizing a Peptide or Protein Having Free Sulfhydryls

Additional Materials Required

- Column: Choose a glass or plastic column size appropriate for the volume of SulfoLink Resin to be used. The Disposable Column Trial Pack (Product No. 29925) contains accessories plus two each of three different column sizes, appropriate for 0.5-10 mL resin bed volumes. Alternatively, several centrifuge-ready Thermo Scientific Pierce Columns are available for resin bed volumes from 25 μl to 10 mL.
- Coupling Buffer: 50 mM Tris, 5 mM EDTA-Na; pH 8.5. Prepare a volume equal to 20 times the volume of SulfoLink Resin to be used.
- Quenching Reagent: L-cysteine.HCl (Product No. 44889)
- Wash Solution: 1M sodium chloride (NaCl)
- Storage Buffer: Phosphate-buffered saline (PBS) or other suitable buffer containing 0.05% sodium azide (NaN3)

Preparation of SulfoLink Resin Column

SulfoLink Coupling Resin and all other reagents are equilibrated to room temperature. The bottle is stirred or swirled to evenly suspend the resin, and then a wide-bore pipette is used to transfer an appropriate volume of the 50% resin slurry to an empty column. For example, 2 mL of resin slurry is transferred to obtain a 1 mL resin bed. The column is then equilibrated with four resin-bed volumes of Coupling Buffer and the bottom column cap is replaced. When using gravity-flow columns, the resin bed does not become dry at any time throughout the procedure. More solution is added or the bottom cap on the column is replaced whenever the buffer drains down to the top of the resin bed.

Couple Peptide/Protein to Resin

Prepared (i.e., reduced) peptide/protein is dissolved in Coupling Buffer and added to the column. 1-2 mL of peptide or protein solution per milliliter of SulfoLink Coupling Resin is used. If desired, a small amount of the peptide or protein solution is retained for later comparison to the coupling reaction flow-through fraction to estimate coupling efficiency. The top cap is replaced and the column is mixed (by rocking or end-over-end mixing) at room temperature for 15 minutes. The column is stood upright and incubated at room temperature for an additional 30 minutes without mixing. The top and bottom column caps are sequentially removed and the solution is allowed to drain from the column into a clean tube. The columns is placed over a new collection tube and the column is washed with three resin-bed volumes of Coupling Buffer. The coupling efficiency is determined by comparing the protein/peptide concentrations (e.g., by absorbance at 280 nm) of the noncoupled fraction to the starting sample.

Block Nonspecific Binding Sites on Resin

The bottom cap on the column is replaced. A solution of 50 mM L-Cysteine.HCl is prepared in Coupling Buffer. One resin-bed volume of 50 mM cysteine solution is added to the column. This is mixed for 15 minutes at room temperature, and the reaction is incubated without mixing for an additional 30 minutes.

Washing the Column

The top and bottom caps are sequentially removed and the column is allowed to drain. The column is washed with at least six resin-bed volumes of Wash Solution (1M NaCl) and then washed with two resin-bed volumes of degassed Storage Buffer.

Preparation of Trx-CL7-SUMO Protein

Expression

*E. coli*, BL21 DE cells were transformed with a vector comprising a nucleic acid encoding thioredoxin (Trx), a modified CL7 DNAse domain and a SUMO domain (cleaved by SUMO protease). The cells were grown in about 1-2 liters of TB medium, at 37° C., to an OD of about 0.8-0.9. Then, the temperature was decreased to 18-20° C. and expression was induced with 0.1-1 mM IPTG and the cells were allowed to grow overnight (20-24 hrs). The culture was centrifuged for about 20 mins. at 6,000 g and the cell pellet was stored at −80° C.

Purification

All procedures were carried out at 4° C. The cell pellet was suspended in lysis buffer (Buf-A; 0.5M NaCl 20 mM Tris pH 8, 5% Glycerol, 0.1 mM PMSF—added each 30 min) with a ratio of 10 ml Buf-A for 1 g cells and sonicated for about 30-40 mins, for about 100 ml of lysate. The lysate was heat sonicated at 70° C. for 45-50 min., and then centrifuged at 40,000 g for about 20 mins. Finally, the supernatant (SN) was filtered through a 45 μm filter. The filtered SN was loaded on the Im7 column (20 ml) at a flow rate of 2-4 ml/min. The column was washed with high salt (1.5M NaCl; 2-3 column volumes) followed by low salt (0M NaCl; 2-3 column volumes). The protein was eluted with 6M guanidine hydrochloride (G-HCl) (FIG. 1B). The Im7 column was reactivated with a one hour gradient refolding of Im7 where G-HCl was replaced with Buf-A (FIG. 1C). Reactivation restored 100% capacity as revealed by an identical purification yield of about 410 mg for the model proteins after the Im7 column was used over 100 times.

Bacterial Multi-Subunit RNA Polymerases (RNAPs)

Two RNAPs (5 protein subunits; $\alpha_2\beta\beta'\omega$, MW~400 kDa) were expressed and purified via essentially the same expression and one step purification protocols—*T. thermophilus* (ttRNAP) and *M. tuberculosis* (mtRNAP). In these examples, the cleavable (by PreScission protease, PSC) CL7-tag is located at the C-terminal end of the largest β'-subunit of the RNAP. In both cases, the overall purification process takes about 4-5 hours, resulting in about 30 mg of catalytically active protein. By comparison, purification of untagged ttRNAP, of the same quality and yield, required five different chromatography columns and the process took about six to seven days.

Expression

*E. coli*, BL21 DE or BL21 STAR cells transformed with a multisubunit vector comprising nucleic acids encoding subunits of ttRNAP or mtRNAP (See FIG. 4), were used. The cells were grown in about 1-2 liters of TB medium, at 37° C., to an OD of about 0.8-1.0. Then, expression was induced with 0.1-1 mM IPTG and the cells were allowed to grow for 3-5 hours. The culture was centrifuged for about 20 mins. at 6,000 g and the cell pellet was stored at −80° C.

Purification

Figure 2:
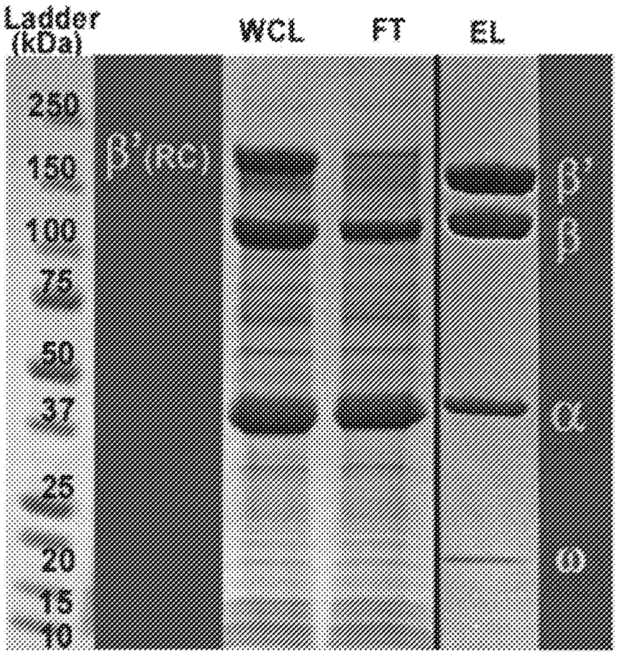
FIG. 2A shows the expression and purification of a multi-subunit RNA polymerase from *T. thermophilus*.
FIG. 2B shows the expression and purification of a multi-subunit RNA polymerase from *M. tuberculosis*. Each of these proteins consists of five protein subunits ($\alpha_2$,$\beta$,$\beta'$,$\omega$) with the total MW of ~400 kDa.
Figure 2:
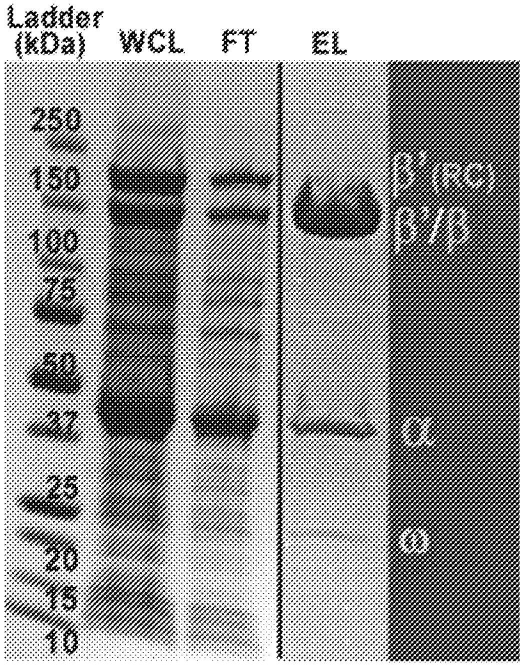

All procedures were carried out at 4° C. The cell pellet was suspended in lysis buffer (Buf-A; 0.5M NaCl 20 mM Tris pH 9, 5% Glycerol, 0.1 mM PMSF—added each 30') with a ratio of 10 ml Buf-A for 1 g cells and the cells were disrupted with a French Press (about 16,000-20,000 psi, in 3 cycles). The lysate was centrifuged at 40,000 g for about 20 mins. Finally, the supernatant (SN) was filtered through a 45 μm filter. The filtered SN was loaded on the Im column (20 ml) at a flow rate of 2-4 ml/min. The column was washed with 2-3 alternate cycles of high salt (1.5M NaCl; 2-3 column volumes) followed by low salt (0M NaCl; 2-3 column volumes). Then, about 0.1-0.2 mg of PSC solution in Buf-A (for about 30-40 mg RNAP) was added. RNAP was eluted after about 1-3 hours (FIG. 2). The CL7-tag which remains bound to the Im7-column was washed out with 6M G-HCl. The Im7 column was reactivated with a 1 hour gradient replacing G-HCl for Buf-A.

Transmembrane Proteins

Two trans-membrane proteins, bacterial membrane integrase Yidc (MW~32 kDa) and human chaperone Calnexin (CNX, ~66 kDa) were expressed and purified via essentially the same expression and one step purification protocols. In these examples, the cleavable (by PSC) CL7-tag is located at the C-terminal end of each protein.

Expression

*E. coli*, BL21 DE or BL21 STAR cells transformed with a single subunit membrane protein vector comprising a nucleic acid encoding nucleic acid encoding CNX or Yidc (See FIG. 4), were used. The cells were grown in about 1-2 liters of TB medium, at 37° C., to an OD of about 0.8-0.9. Then, the temperature was decreased to 18-20° C. and expression was induced with 0.1-1 mM IPTG. After induction, the cells were allowed to grow overnight (20-24 hours). The culture was centrifuged for about 20 mins. at 6,000 g and the cell pellet was stored at −80° C.

Purification

All procedures were carried out at 4° C. The cell pellet was suspended in lysis buffer (Buf-A; 0.35M NaCl 20 mM Tris pH 8, 5% Glycerol, 0.1 mM PMSF—added each 30 min) with a ratio of 20 ml Buf-A for 1 g cells and the cells were disrupted with a French Press (about 16,000-20,000 psi, in 3 cycles). The lysate was centrifuged at 40,000 g for about 20 mins. Finally, the supernatant (SN) was filtered through a 45 μm filter.

DNA was eliminated using polyethylene-emine (PE) precipitation. Essentially, 0.06% PE was added to the lysate in 3 steps (0.02% PE for one step), mixing the precipitant for ~5-10 min. between each step of PE addition. The PE-treated sample was centrifuged for 15-20 min at 4,000-8,000 g. The SN was disposed and the pellet was resuspended in Buf-A1 (0.6M NaCl, 20 mM Tris pH 8, 5% Glycerol, 1.5% dodecyl-maltopyranoside, DDM) and mixed for about 30-40 mins. The sample was centrifuged again and the salt concentration was increased to 1M NaCl. The resulting SN was loaded on to the Im7 Column.

Figure 3:
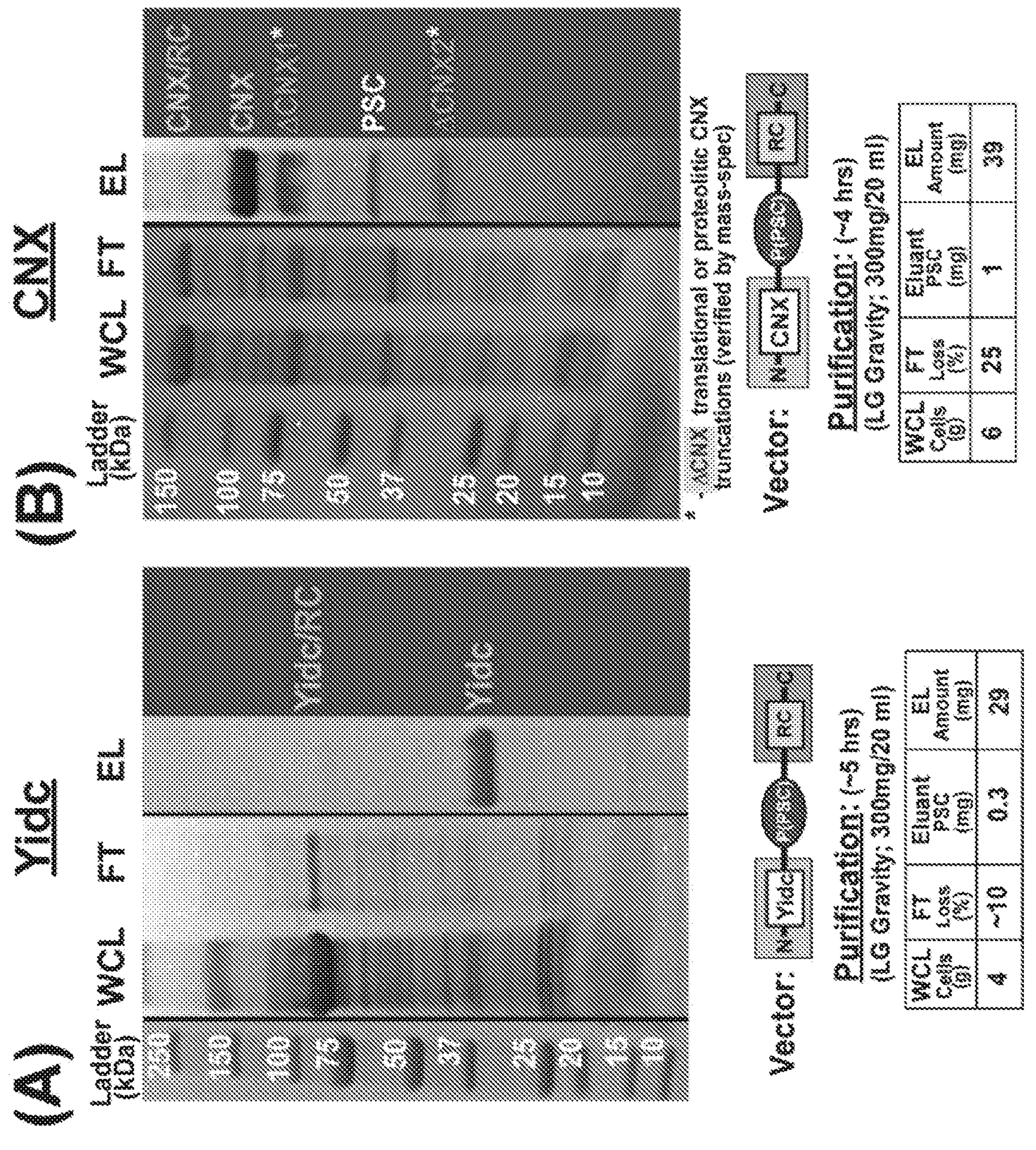
FIG. 3A shows the expression and purification of Yidc, a transmembrane bacterial integrase.
FIG. 3B shows the expression and purification of calnexin, a transmembrane human chaperone protein.

The PE-SN was loaded on the Im column (20 ml) at a flow rate of 1-2 ml/min. The column was washed with 2-3 alternate cycles of high salt (1.5M NaCl; 2-3 column volumes) followed by low salt (0M NaCl; 2-3 column volumes) buffers. Then, about 0.1-0.2 mg of PSC (for about 20-40 mg protein target) in Buf-A2 (0.5M NaCl, 20 mM Tris pH 8, 5% glycerol, 0.1% DDM) was added. The target protein was eluted after about 1-3 hours (FIG. 2). The CL7-tag which remains bound to the Im7-column was washed out with 6M G-HCl (FIG. 3). The Im7 column was reactivated with a 1 hour gradient replacing G-HCl for Buf-A.

Purification of Condensin

Figure 5:
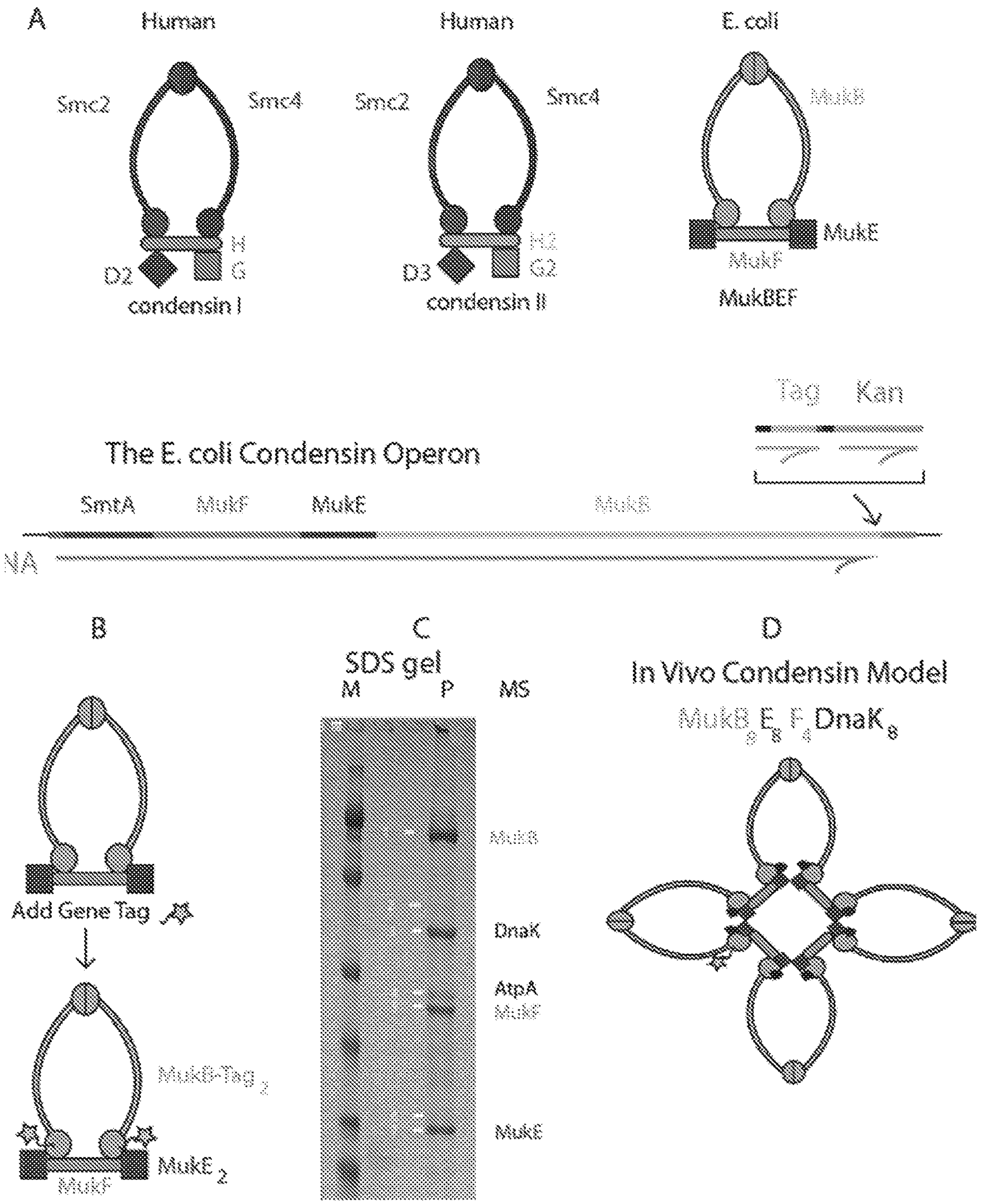
FIG. 5A shows the structural similarity of bacterial (*E. coli*) and mammalian (human) condensins (condensin I and condensin II). The genetic structure of the *E. coli* and *Salmonella Typhimurium* DNA condensin (or MukFEB operons) is also shown. Transcription initiates near the smtA gene, which encodes an S-adenosyl methionine transferase. All four genes of this operon are translationally coupled to the previous gene. A ribosome translates every protein without dissociating from mRNA. The One Column tag was introduced by inserting a module precisely after the last amino acid of MukB creating a MukB-Tag fusion. Selecting for kanamycin resistance facilitates this genetic method.
FIG. 5B shows the expected structure of a MukFEB condensin was two MukB and MukE subunits with only one copy of MukF.
FIG. 5C shows the results of condensin purification using the One Column approach. Four grams of protein dissolved in 200 ml of buffer was applied to a 1.5 ml One Column. After extensive washing with 100 column volumes of high and then low salt buffer, all proteins were released from the column by applying 6 M Guanidine H-Cl, yielding 750 μg of a highly purified fraction.
FIG. 5D shows a MukB octamer structure.

A *Salmonella typhimurium* DNA condensing complex, which was expected to have a MW of 583 kDa, turned out to have a molecular weight of >2,000 kDa. Condensins are highly conserved protein machines that fold and compact chromosomal DNA in bacterial and mammalian cells into self-adherent nucleoids and chromosomes, respectively. The structural similarity of bacterial and mammalian condensins is illustrated in FIG. 5A. In humans, there are two essential complexes. Condensin I and condensin II share a large subunit heterodimer of SMC2 and SMC4 but have different proteins associated with the terminal AAA-ATPase domain. In chromosome function condensin I compacts DNA along in the long axis while condensin II compacts DNA loops perpendicular to the long axis. In all organisms studied to date, condensins prove to be exceedingly difficult to reassemble from the known protein subunits. In *E. coli* and *Salmonella* the large subunit (MukB 175 kDa) is a homodimer that interacts with MukE and MukF via the AAA-ATPase motor. The mukB gene was modified in the chromosome by inserting the CL7 tag through a flexible protein linker to the C-terminus of the MukB (FIG. 5A). The expected structure of a MukFEB condensing is shown in FIG. 5B. 6 L of bacterial cells grown to late log phase (4 grams of packed cell paste) were prepared for cell lysis. Purification was carried out with a 1.5 ml mini-column of Im7 beads. After loading 200 ml of lysate onto the column, washing was carried out with 200 volumes of alternating high and low salt buffer. The column was eluted first by Prescission protease cleavage, which released only 20% of the protein, and then eluted with 6M G HCl, which released the >80%, which still retained at least one CL7 tag after proteolytic digestion. The isolated condensin complex was as pure as the Biorad markers for the condensin proteins (FIG. 5C). In addition to the expected proteins, MukB, MukE and MukF, two other proteins were detected. The molecular chaperone, DnaK was present in levels equivalent to MukB and MukE. This protein may be involved in changing a MukB dimer into a MukB octamer. A model for in vivo condensin structure of the 80% of the molecules retained on the column after proteolytic treatment is shown in FIG. 5D.

Vectors

Figure 4:
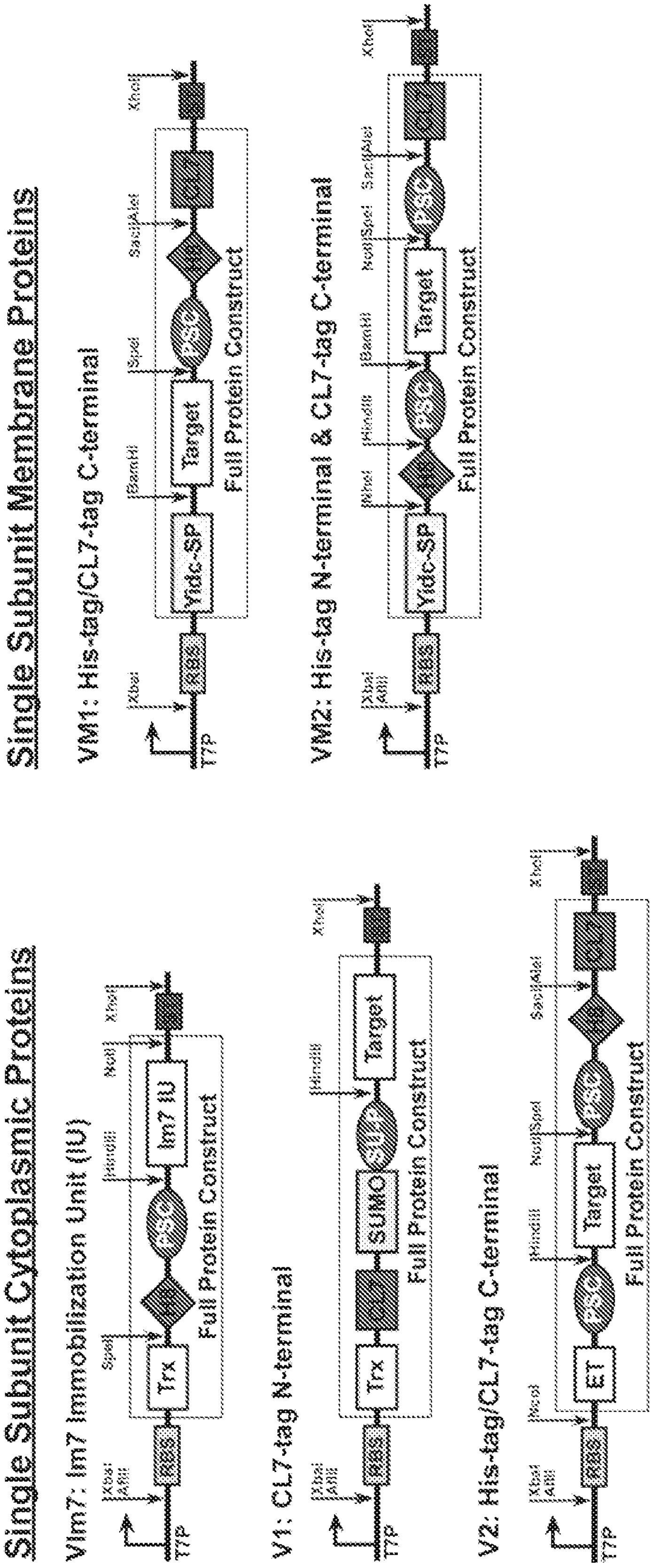
FIG. 4 is a schematic of the vectors constructed for protein expression and purification using a CL7/Im7 (RC/LG) affinity system.

As shown in FIG. 4, numerous vectors have been constructed that allow expression and purification of single-subunit cytoplasmic and membrane proteins, as well as multi-subunit complexes. A pET28a vector from Novagen was used as the template for all of the vectors shown in FIG. 4. The nucleic acid sequence for the Vlm7 vector is set forth herein as SEQ ID NO: 14. The nucleic acid sequence for the V1 vector is set forth herein as SEQ ID NO: 15. The nucleic acid sequence for the V2 vector is set forth herein as SEQ ID NO: 16. The nucleic acid sequence for the VM1 vector comprising a nucleic acid sequence encoding Yidc is set forth herein as SEQ ID NO: 17. The nucleic acid sequence for the VM2 vector comprising a nucleic acid sequence encoding CNX is set forth herein as SEQ ID NO: 18. The nucleic acid sequence for the Vlm7 vector is set forth herein as SEQ ID NO: 19. The multi-subunit vector comprising a nucleic acid sequence encoding ttRNAP is set forth herein as SEQ ID NO: 20. The multi-subunit vector comprising a nucleic acid sequence encoding mtRNAP is set forth herein as SEQ ID NO: 21.

Example II

Figure 6:
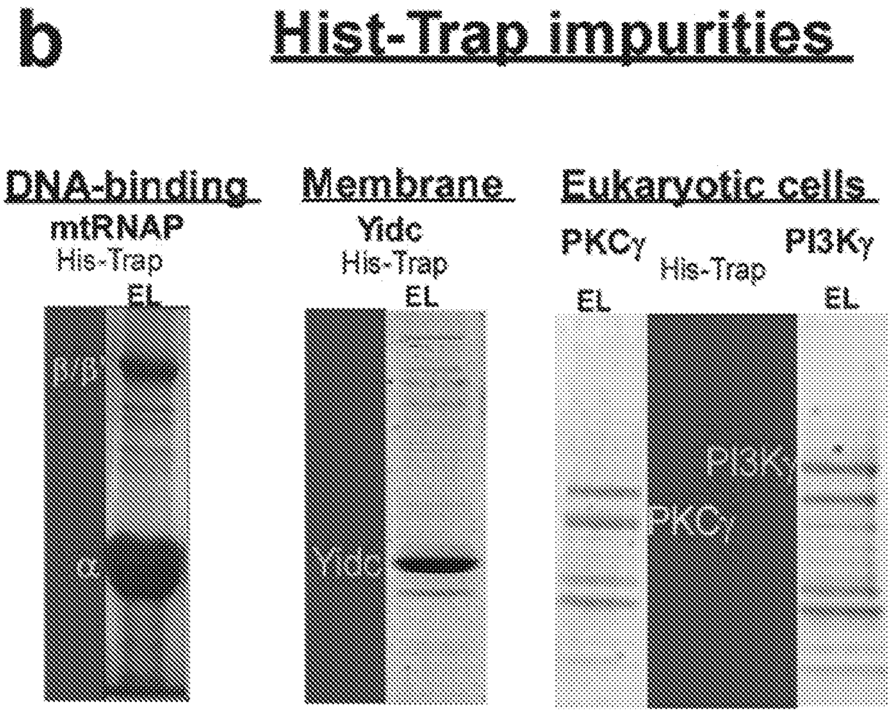
FIG. 6*a* shows the performance of most widely used purification techniques. Comparative results with the CL7/Im7 system are shown. Abbreviations are as follows: CalBD—calmodulin binding domain; MBP—maltose binding protein; GST—gluthathione-S transferase; ChBD—chitin binding domain; CL7/Im7—colicin E7 DNAse domain and its inhibitor, Immunity protein 7; Prot—protein; Pept—short peptide; SM—small molecule; PP—(Price/Performance)=(Price of 1 ml beads)/(Amount of protein bound to 1 ml beads); EL—eluate.
FIG. 6*b* shows the results of using a one-step His-Tag purification of multi-subunit ($\alpha_2\beta\beta'\omega$) DNA-binding *M. tuberculosis* RNA polymerase (mtRNAP; left), bacterial transmembrane integrase, Yidc (middle), and two human kinases expressed in host cells.

Biological approaches such as proteomics, interactomics and in vitro drug screening rely largely on efficient purification of the proteins being studied. Most widely used commercial columns provide modest yields of only a few milligrams (FIG. 6*a*). These yields are barely suitable for structural studies and commercial protein production. Moreover, analysis of the recommended commercial protocols and respective publications suggests that no commercial affinity system exists that tolerates high salt concentrations at the most crucial step of crude lysate loading on the columns (FIG. 6*a*). Most commercial systems tolerate a salt concentration of 0.2M-0.5M, at best. Consistently, trials with the GST, MBP and Step-Tag columns demonstrated that at salt concentrations over ~0.3M only a very small fraction (5-10%) of the tagged proteins binds to the ligands on the column. On the other hand, loading the lysates at a low/medium salt concentration often results in residual contaminations that cannot be washed out entirely afterwards, even with high-salt buffers. Application of these "low-salt" columns, thus, is limited to only a subset of biological targets, which form no salt-dependent interactions with the pool of the untagged cellular molecules (for example, proteins, DNA/RNA).

In fact, among commercially available purification techniques only the His-tag ($Ni^{2+}$-based) approach demonstrates not only H-yield capacity but also allows for high-salt loading of lysates without loss of binding affinities (FIG. 6*a*). However, results show that the His-tag approach possesses relatively high, non-specific, but cooperative affinity to DNA and to DNA-binding proteins, as well as to some cellular proteins, including many membrane proteins and cytosolic proteins from eukaryotic cells (FIG. 6*b*). These contaminations occur largely in a salt-independent manner that often result in only 30-70% purity for these, $Ni^{2+}$ sensitive categories of biological targets (FIG. 6*b*), thus requiring additional purification steps to obtain high purity samples. Thus, protein purification remains a tricky, target-dependent, multi-step process that creates one of the major bottlenecks in biological sciences and their medical/industrial derivatives.

As set forth above, an ultra-high affinity purification system based on the small protein/protein (Colicin E7 DNAse/Immunity Protein 7; CL7/Im7; $K_D$~$10^{-14}$-$10^{-17}$M) complex, with an affinity of 5-8 orders of magnitude higher than that of any other available analogs (FIG. 6*a*) allows for a one-step HHH-purification of the most challenging biological targets (for example, large multi-subunit, DNA/RNA-binding and membrane proteins).

Expression

Unless otherwise specified the same procedures were used for plasmid construction, expression, cell growth and lysis throughout Example II. A commercial pET28a expression vector (Invitrogen (Carlsbad, Calif.)) was used as a template vector and nucleotide gene sequences were inserted using the unique restriction sites of the vector. The gene sequences were designed through the manual inspection and modification of the natural (genomic) sequences to exclude the rare *E. coli* codons and high (G/C) content, where appropriate. The fragments of the designed sequences were synthesized commercially (IDT (Coralville, Iowa)) and then merged together, either through PCR (Phusion polymerase; NEB (Ipswich, Mass.) or through ligation using the unique restriction sites during cloning into the PET28a template vector. The resulting expression plasmids were transformed in BL21-Star (DE3) (Invitrogen) competent cells, colonies were grown overnight (37° C.) and several (2-3) resulting clones were sequenced to confirm that the sequences were correct. The cells were cultivated in TB media (http://www.bio-protech.com.tw/databank/DataSheet/Biochemical/DFU-J869.pdf) at 20° C. for 20-24 hrs in 2 or 4 liter flasks (for 1 or 2 L of culture) according to the following protocol.

The cells were first grown at 37° C. for ~2-2.5 hrs until an $OD_{560}$ of the cultures reached values of ~0.7-0.8. The temperature was then decreased to 20° C. and overexpression was induced by addition of 0.1 mM isopropyl β-D-1-thiogalactopyranoside (IPTG). The overnight cultures were centrifuged at 4,000 g for ~30 minutes, and the cell pellets were frozen at −80° C. For purification, the frozen cell pellet was suspended in the respective lysate buffers (1 g cells→10 ml buffer) and then disrupted using the Nano DeBEE high pressure homogenizer (BEE International) using ~15,000 psi of pressure for ~3 mins (for ~3 g cells) at 4° C. The lysates were then centrifuged at 40,000 g for 20 minutes and filtered through the 45 μm filter. All purifications were carried out using the Acta Prime purification system (GE Healthcare (Atlanta, Ga.)).

Im7 Column Preparation

Figure 7:
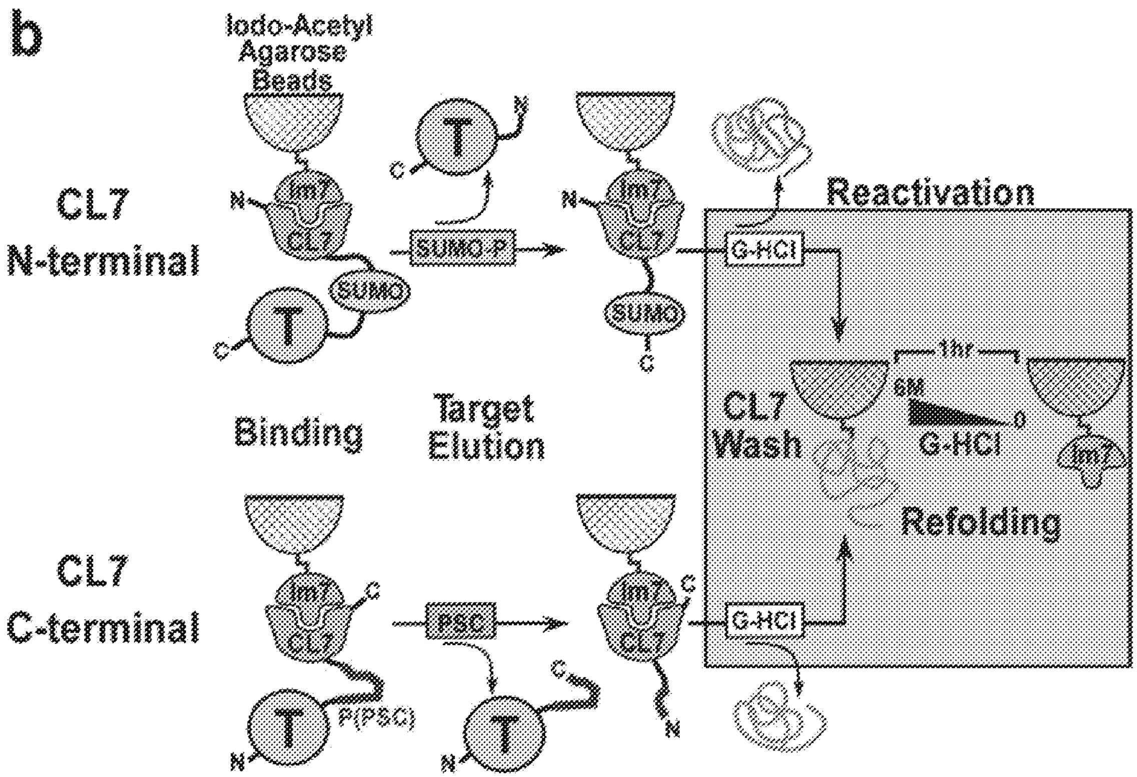
FIG. 7*a* shows the wild-type CL7-DNAse amino acid sequence (SEQ ID NO: 1). Active site residues (H99, H124 and H128 of SEQ ID NO: 1) and DNA-binding residues (R2, K4, K11, K45, K51, K52, S105 of SEQ ID NO: 1) that were modified as set forth herein are highlighted.
FIG. 7*b* shows a schematic protocol for purification of CL7-tagged target proteins using the Im7 protein coupled to Sulfo-Link 6B agarose beads, and expression and purification of purification a 45 kDa protein (Trx→RC→SUMO). Abbreviations are as follows: SUMO, SUMO-P—SUMO domain and SUMO protease, respectively; P(PSC), PSC—precision protease binding site and protease itself, respectively; T—target protein; G-HCl—guanidine hydrochloride; H8—8 histidine tag; Trx—thioredoxine; WCL—whole cell lysate; FT—flow through; EL—eluate.
FIG. 7*c* shows expression and purification of an Im7 immobilization unit.
FIG. 7*d* shows expression and purification of a CL7-tagged protein.
Figure 7:
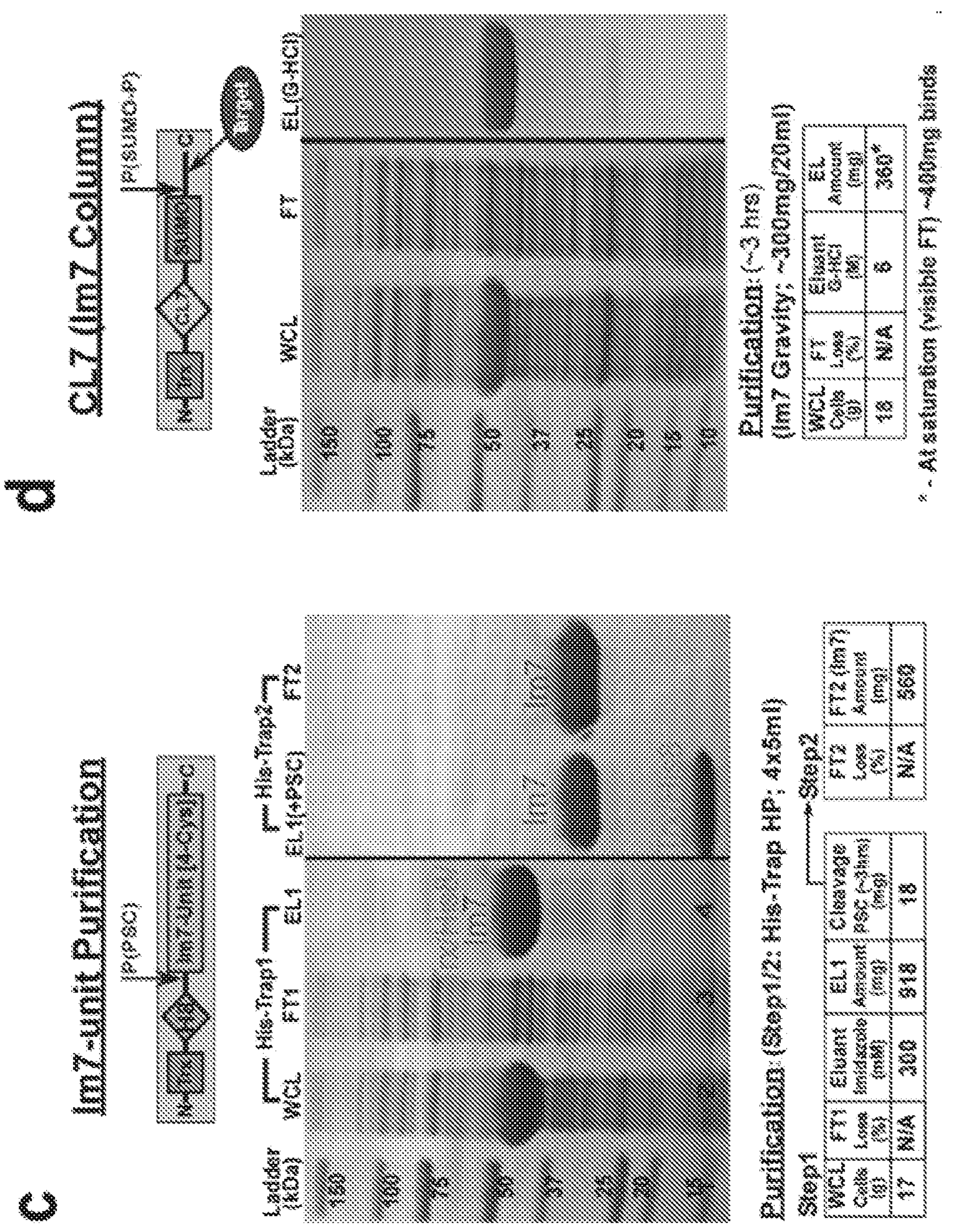

A 1 L culture of a Im7 immobilization unit usually produces ~2 g of cells. Purification was carried out in two chromatographic steps (FIG. 7*c*). First, the cell lysate (lysis buffer: 0.5 M NaCl, 20 mM Tris pH8, 5% glycerol, 0.1 mM PMSF) was loaded on the His-Prep FF (GE Healthcare) column (flow rate 5 ml/min.) in the lysis buffer (buffer A) with addition of 2% buffer B (1M imidazole). After loading, the column was washed by two alternate cycles of applying high/low (1M/0M NaCl) salt buffers with the addition of 5% buffer B, and then eluted in buffer A with addition of 25% buffer B. In the next step, the eluate was dialyzed against buffer A for ~4-5 hrs in presence of purified precision protease (PSC, lab prep) to cleave the expression (thioredoxin, Trx) and His8 tags (FIG. 7*c*). The dialyzed sample was heated at 70° C. for ~45 min to eliminate PSC and was then loaded on the His-Prep column again under the same conditions as the first step. The flow through (FT) at the second step contained the very pure Im7-unit (FIG. 7*c*), which was then concentrated to ~20-25 mg/ml and dialyzed against the coupling buffer recommended by Thermo Fisher (Waltham, Mass.) for protein immobilization to the SulfoLink (iodo-acetyl activated) 6B agarose beads. Immobilization was carried out according to the commercial protocol (http://www.funakoshi.co.jp/data/datasheet/PCC/20401.pdf) in a dark room and the reaction was normally completed in ~20-25 min. The typical concentration of the immobilized Im7-unit was ~15 mg/ml beads (or ~0.8 mM). The Im7-activated beads were then packed in a 20 ml glass, low pressure column, which can be used for purification through respective adaptors, with the Acta Prime system.

Purification of a Model Protein

To test column performance, a model protein (Trx→CL7→SUMO) was used that can also serve as a template for the target proteins with the N-terminal CL7-tag. In other words, a target protein can be cloned in this expression vector right after the SUMO domain using the unique HindIII/XhoI restriction sites. The Im7-column was tested with this model protein multiple times under different loading conditions varying salt (0.3-1.2M NaCl), reducing (β-mercaptoethanol up to 15 mM) and metal chelating (EDTA up to 20 mM) agents, detergent (DDM up to 1.5%) and flow rate (up to 4 ml/min.) and results similar to those shown in FIG. 7*d* were obtained. Upon loading, the column was subjected to a few (2-3) alternate cycles of high/low (1M/0M NaCl) salt buffer washing. The protein was then eluted under denaturing (6M guanidine hydrochloride, G-HCl) conditions, followed by column cleaning/reactivation using the gradient option of Acta Prime (FIG. 7*b*), i.e. gradually exchanging the G-HCl with the physiological buffer (0.5M NaCl, 20 mM Tris pH8, 5% glycerol) in ~1 hr. No significant loss of capacity was detected after multiple (100+) reactivations. The concentrations of the model protein bound to the Im7 column were in the range of ~(15-20) mg/ml beads.

Purification of ttRNAP and mtRNAP

Figure 8:
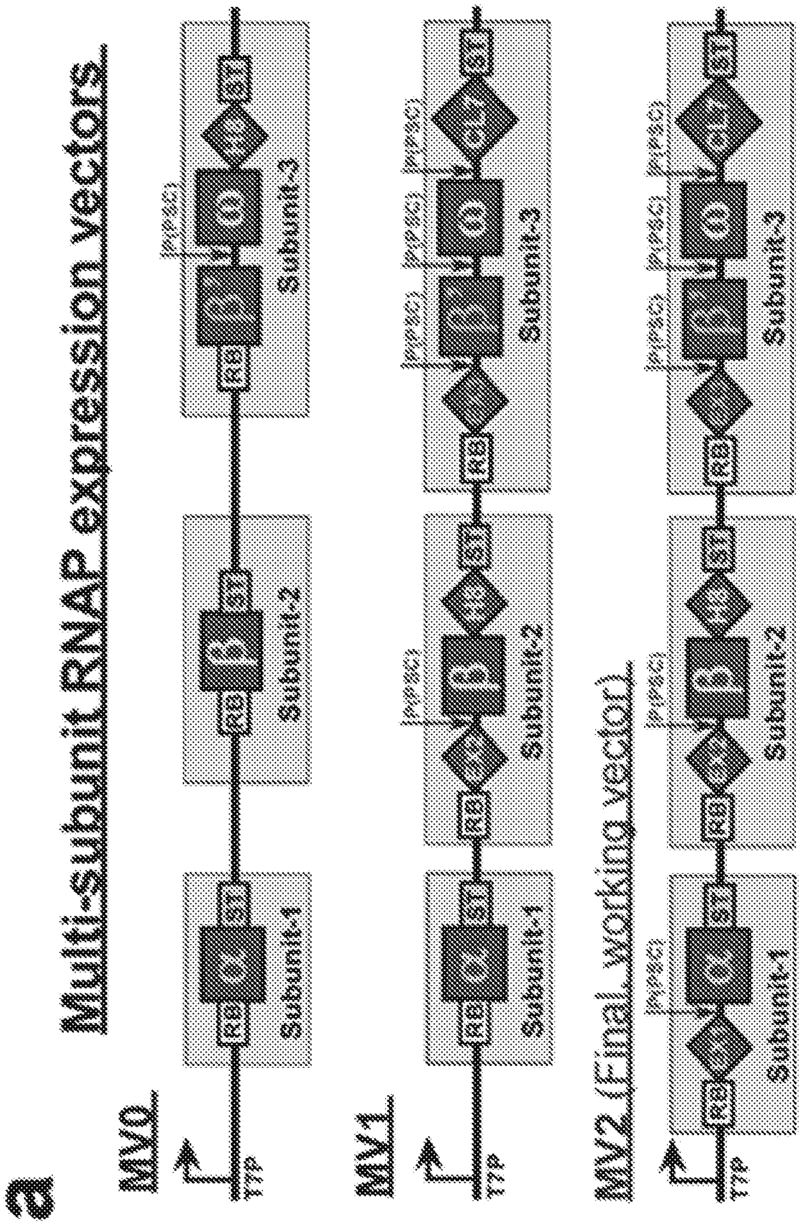
FIG. 8*a* show examples of multi-subunit RNAP expression vectors.
FIG. 8*b* is a gel showing expression levels of ttRNAP using the purification systems described herein.
FIG. 8*c* is a gel showing one-step purification of ttRNAP using the His-tag (left panel) and (CL7/Im7) (right panel) approaches.
FIG. 8*d* shows the results of transcription elongation assays for overexpressed (left panel) and expressed (right panel) ttRNAP from host thermophilic cells. Abbreviations are as follows: T7P—T7 promoter; RB—ribosome stating site; ST—stop codon; EX—the short N-terminal "expression" peptides from the maltose-binding protein (EX1, 25 a.a.), thioredoxin (EX2, 30 a.a.), and NusA (EX3, 30 a.a); H8—8 histidine tag; P(PSC)—prescission protease cleavage site; PSC—prescission protease; WCL—whole cell lysate; WCL1—lysate (WCL) heated at 70 C for ~45 mins; FT—flow through; EL—eluate; RNA18—synthetic 18-mer RNA olig labeled with fluoresceine (FLU) at the 5'-end. T/NT—DNA template (T) and non-template (NT) strands in the synthetic transcription elongation scaffold.
Figure 8:
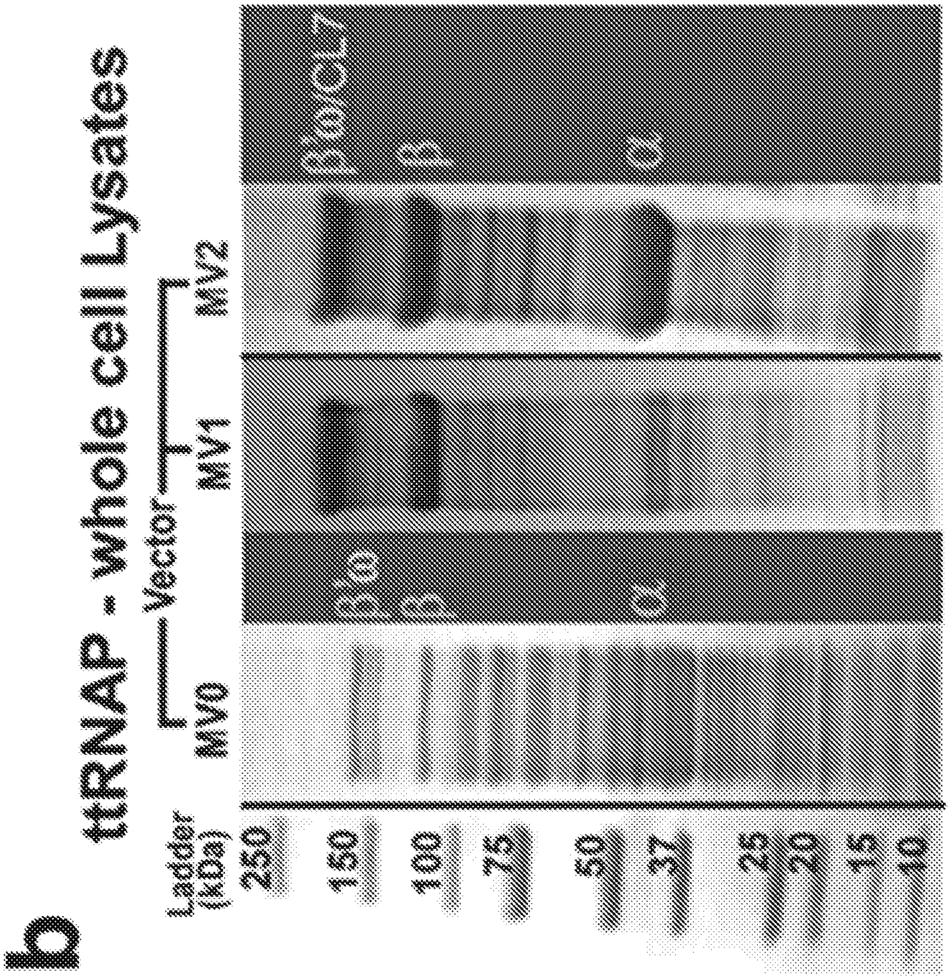
Figure 8:
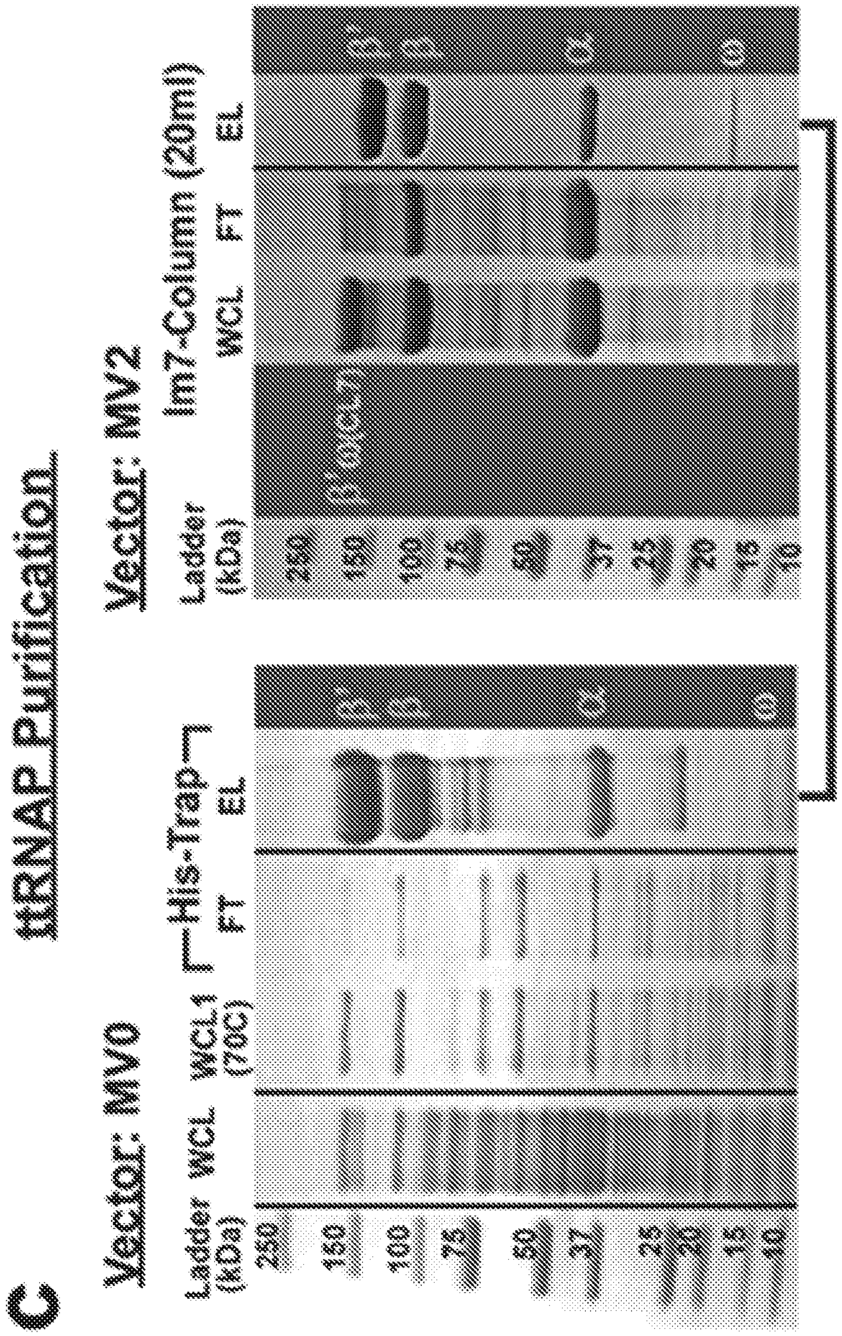
Figure 8:
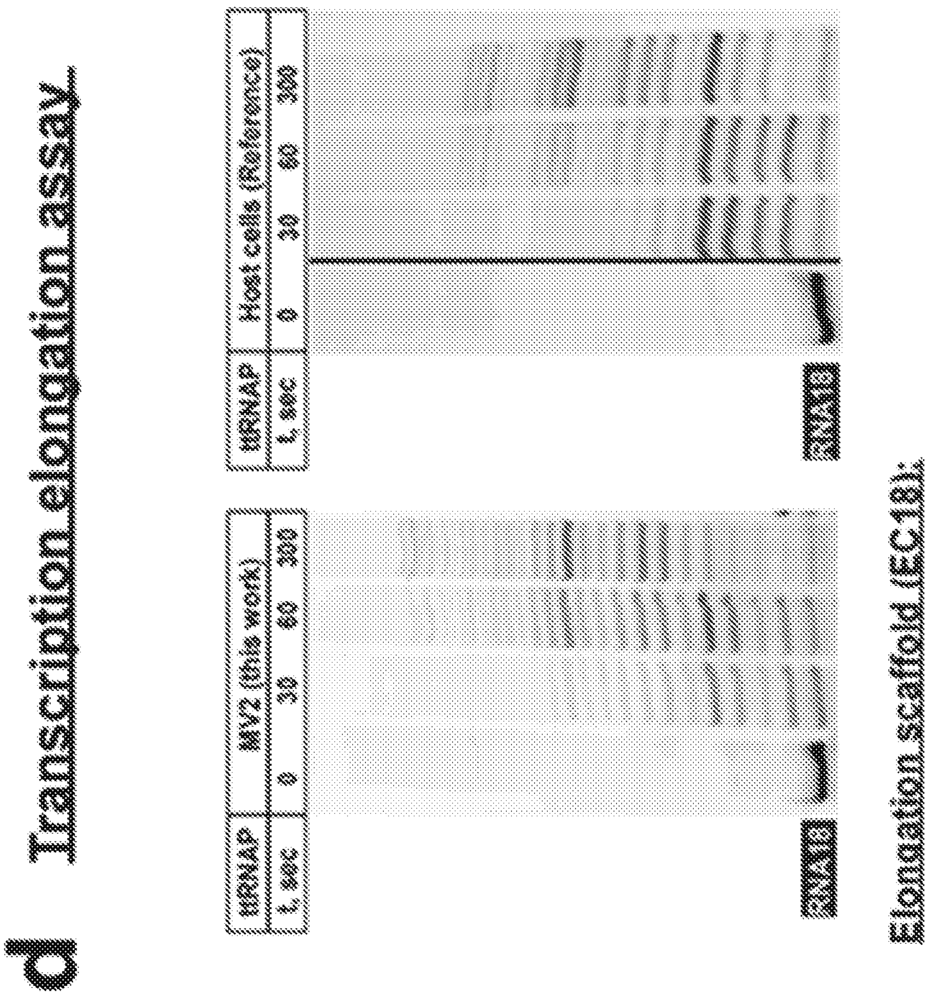
Figure 9:
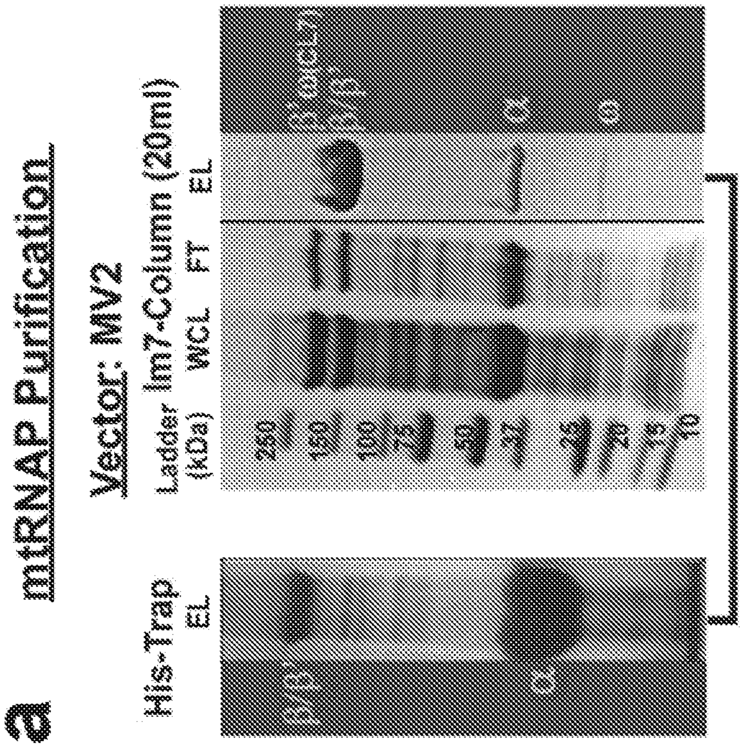
FIG. 9A shows the results of one-step purification of mtRNAP using the His-tag (left panel) and (CL7/Im7) (right panel) approaches.
FIG. 9B shows transcription elongation assays for overexpressed mtRNAP (left panel) and commercial *E. coli* RNAP (ecRNAP, right panel). Abbreviations are as follows: PSC—prescission protease; WCL—whole cell lysate; FT—flow through; EL—eluate; RNA18—synthetic 18-mer RNA olig labeled with fluoresceine (FLU) at the 5'-end. T/NT—DNA template (T) and non-template (NT) strands in the synthetic transcription elongation scaffold.
Figure 9:
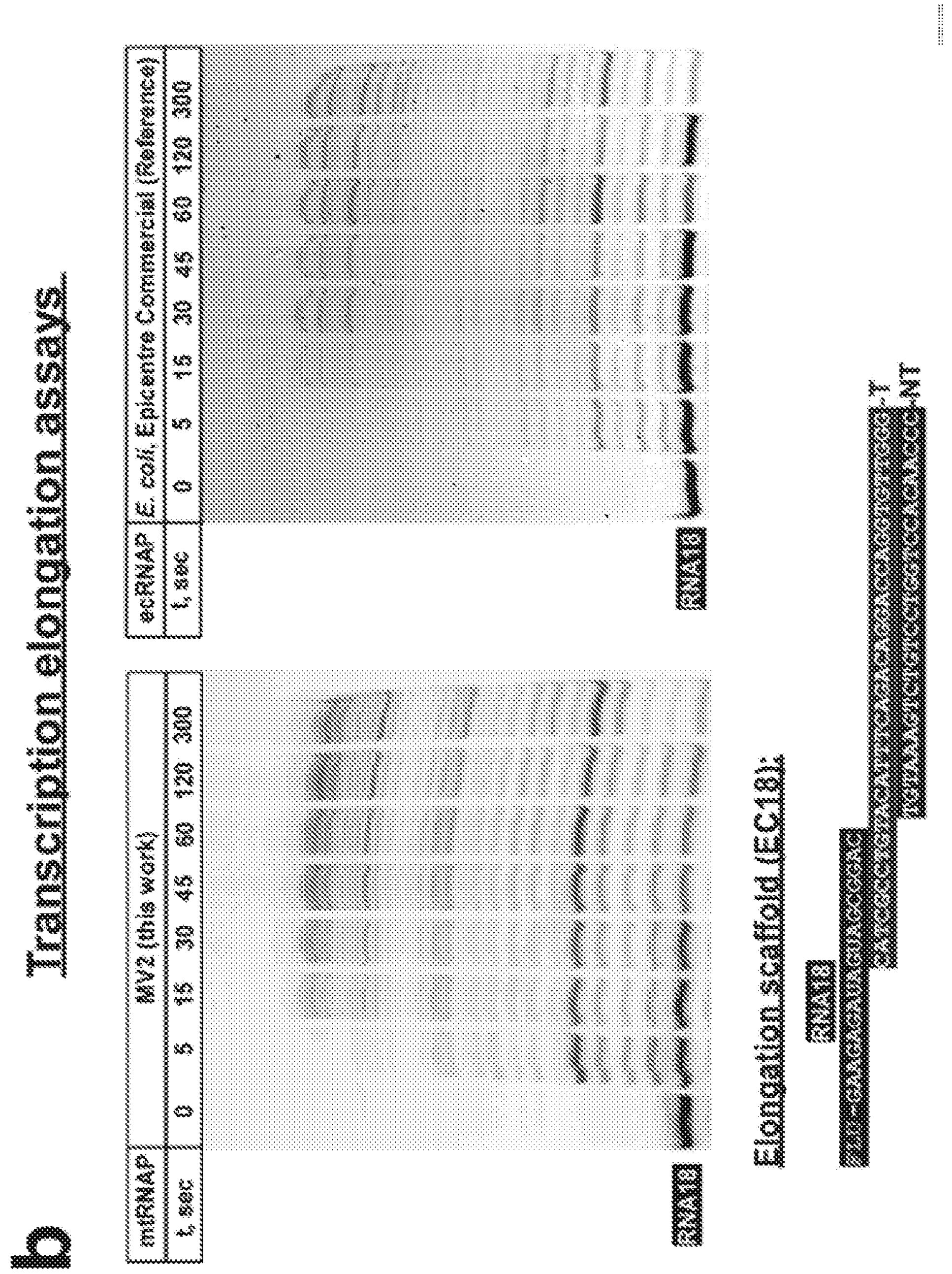

A 1 L culture of ttRNAP or mtRNAP usually produces ~8-1 g cells. The lysis buffer contains 0.1M NaCl, 20 mM Tris pH 8.0, 5% glycerol, 0.5 mM $CaCl_2$, 10 mM $MgCl_2$, 0.1 mM PMSF, ~120-150 μg DNAse I (Grade-I, Roche), and 1 tablet of an inhibitory cocktail for ~3 g cells. The cell lysates were incubated for ~1.5 hr at 4° C. in the lysis buffer, with addition of 0.05 mM PMSF each 30 mins. The lysates were then diluted 2 times with the 2-fold loading buffer containing (2.3M NaCl, 20 mM Tris pH 8.0, 5% glycerol) to increase salt concentration to 1.2M and loaded on the 20 ml Im7-column (flow rate of ~1.5-2 ml/min; FIGS. 8*c* and 9*a*). Upon loading, the column was subjected to a few (2-3) alternate cycles of high/low (1M/0M NaCl) salt buffer washing. The proteins were then eluted using small amounts (~0.3 mg) of PSC slowly (~0.2 ml/min.) loaded on the column in the elution buffer (0.5M NaCl, 20 mM Tris pH 8.0, 5% glycerol, 0.2 mM EDTA). After elution the CL7-tag was washed out with 6M G-HCl and the column was reactivated through a standard gradient refolding procedure.

For the His-tagged ttRNAP construct (vector MV0, FIGS. 8*a* and 8*c*, left panel) purification was carried out under the same conditions as that for the Im7 purification, with the exceptions that 20 mM and 50 mM imidazole were added to the loading and washing buffers, respectively, while the protein was eluted with the elution buffer containing no EDTA and 250 mM imidazole.

Fluorescent Transcription Assays

To assemble transcription elongation complexes, the 18-mer RNA (RNA18) labeled with fluoresceine (FLU) at the 5'-end, Template (T) and Non-Template (NT) oligonucleotides were ordered from IDT. The nucleic acid elongation scaffold was then assembled (FIGS. 8*d* and 9*b*). The transcription elongation reactions were carried out under the following conditions; 0.1M NaCl, 50 mM Tris pH 8.0, 5 mM $MgCl_2$, 100 μM NTPs, ~1.43 μM RNAP, 0.75 μM RNA18 (in the scaffold) at t=20° C. The reactions were stopped by 8M urea and loaded on the denaturing 20% polyacrylamide gels. The gels were then processed by the fluorescent imager, Typhoon Trio (GE Healthcare) and quantitated with the respective ImageQuant program (GE Healthcare).

Purification of the Yidc Protein from the Uninduced Cells

Figure 10:
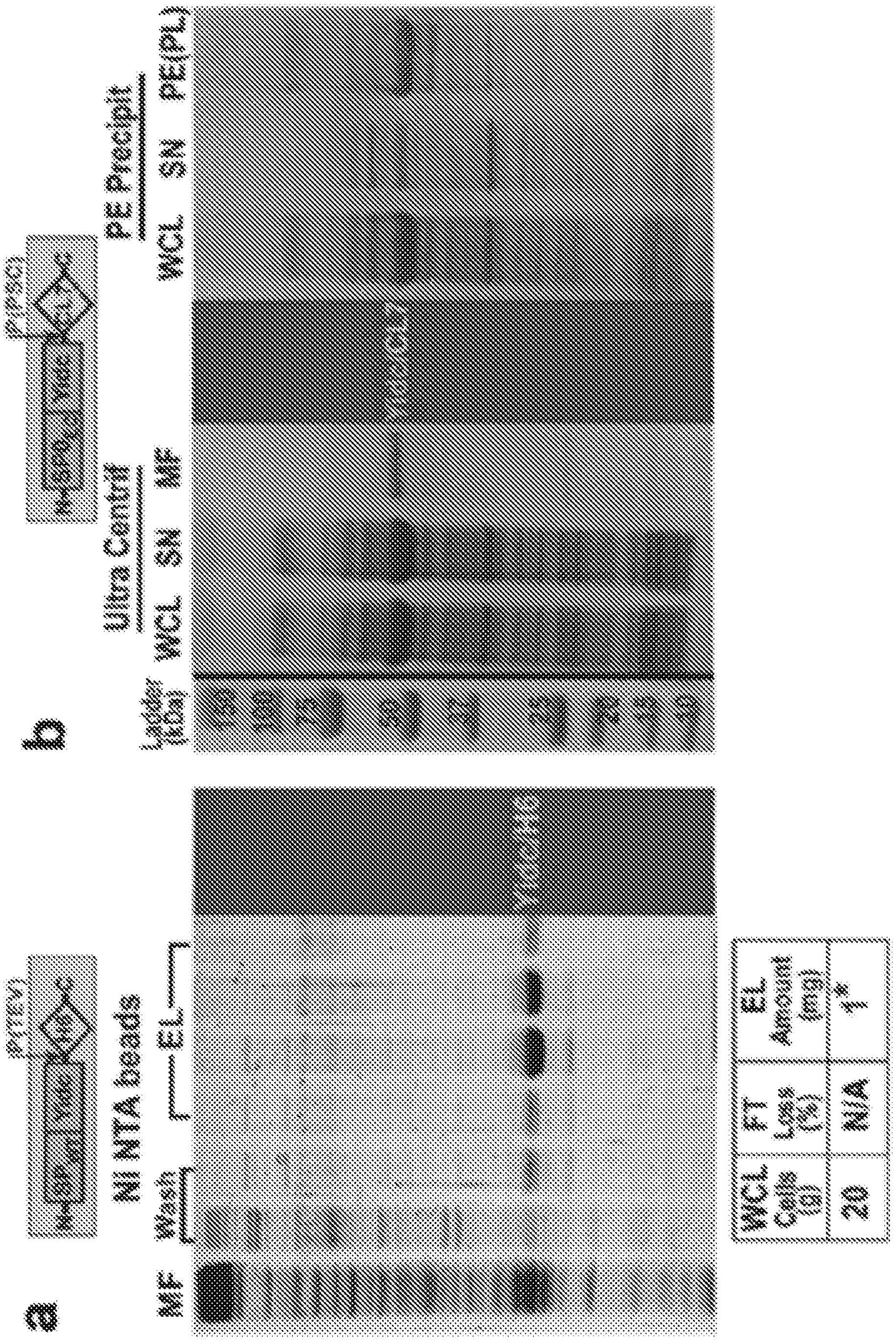
FIG. 10A shows the results of expression and a one-step purification of Yidc using the His-tag approach and the wild-type (WT, not adjusted for the *E. coli* codons) sequence.
FIG. 10B shows the results of expression (with IPTG induction) of Yidc with the gene sequence adjusted for *E. coli* codons and C-terminal C17 tag. With the enhanced expression, Yidc and the other membrane proteins remain in the soluble fraction (SN) upon ultracentrifugation (left panel), but precipitates with DNA upon polyethylenimine (PE) precipitation in ~0.3-0.35M NaCl (right panel).
FIG. 10C shows the results of a one-step purification of Yidc using the (CL7/Im7) approach. Purification using ultracentrifugation of the non-induced cells and the WT signal peptide (SP) sequence, with Cys residue at the N-terminus of the Yidc after cleavage by the signal peptidase is shown. 10D shows the results of a one-step purification of Yidc using the (CL7/Im7) approach. Purification with no ultracentrifuge step but using the PE precipitation instead and with the N-terminal Cys/Ser mutation is shown. Abbreviations are as follows: H6—6 histidine tag; PSC—prescission protease; P(TEV)/P(PSC)—TEV/PSC cleavage sites; MF—membrane fraction (ultra-centrifuge pellet dissolved in 1.5% dodecyl-maltopyranoside, DDM); Wash—column wash with 30/50 mM imidazole; WCL—whole cell lysate; SN—supernatant (soluble fractions); PE(PL)—supernatant after PE pellet is washed with the buffer containing 0.6M NaCl and 1.5% DDM; Cells (3/20 hrs)—uninduced (no IPTG) cells after 3/20 hrs proliferation; FT—flow through; EL—eluate; $SP_{WT}$, $SP0_{Ec}$, $SP1_{EC}$—Yidc signal peptide with the WT ($SP_{WT}$), adjusted for *E. coli* codons ($SP0_{EC}$) gene sequences, and with *E. coli* adjusted sequence containing the (C/S) mutation.
Figure 10:
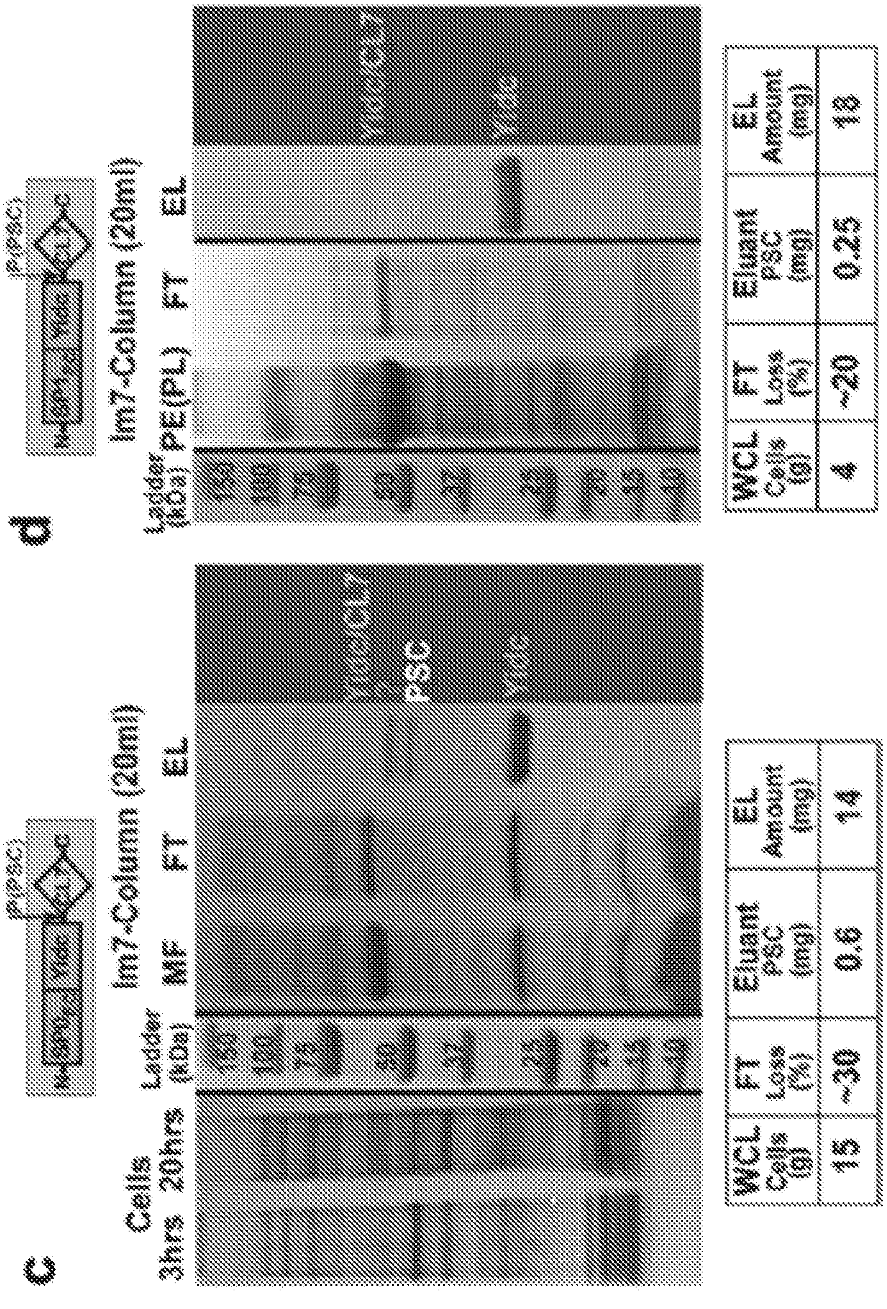

Cells were grown as described above, except that, after cell density reached $OD_{560}$~0.7-0.8 at 37° C., the temperature was decreased to 20° C. with no IPTG addition. The 1 L culture of uninduced Yidc produced ~2 g cells. The 200 ml of clear (filtered) lysate (lysis buffer: 0.5M NaCl, 20 mM Tris pH 8.0, 5% glycerol, 0.1 mM PMSF, 4 inhibitory tablets (Roche Catalogue No. 04 693 132 001 (Basel, Switzerland)) were ultracentrifuged at 120,000 g for 1.5 hrs. The pellet containing the membrane fraction (FIG. 10*c*) was then dissolved in ~100 ml loading buffer (0.9M NaCl, 20 mM Tris pH 8.0, 5% glycerol, 0.1 mM PMSF, 1.5% DDM) and ultracentrifuged again at 120,000 g for 30 min. The supernatant was loaded on the 20 ml Im7-column (flow rate of ~1.5 ml/min; FIG. 10*c*). Upon loading, the column was subjected to washing with a few (2-3) alternate cycles of high/low (1M/0M NaCl) salt buffers containing 0.1% DDM. The proteins were then eluted using the small amounts (~0.6 mg) of PSC slowly (~0.2 ml/min.) loaded on the column in the elution buffer (0.5M NaCl, 20 mM Tris pH 8.0, 5% glycerol, 0.2 mM EDTA, 0.1% DDM). After elution the CL7-tag was washed out with 6M G-HCl and the column was reactivated through the standard gradient refolding procedure (see above).

Purification of the Yidc and Calnexin Proteins from the Induced Cells

Figure 11:
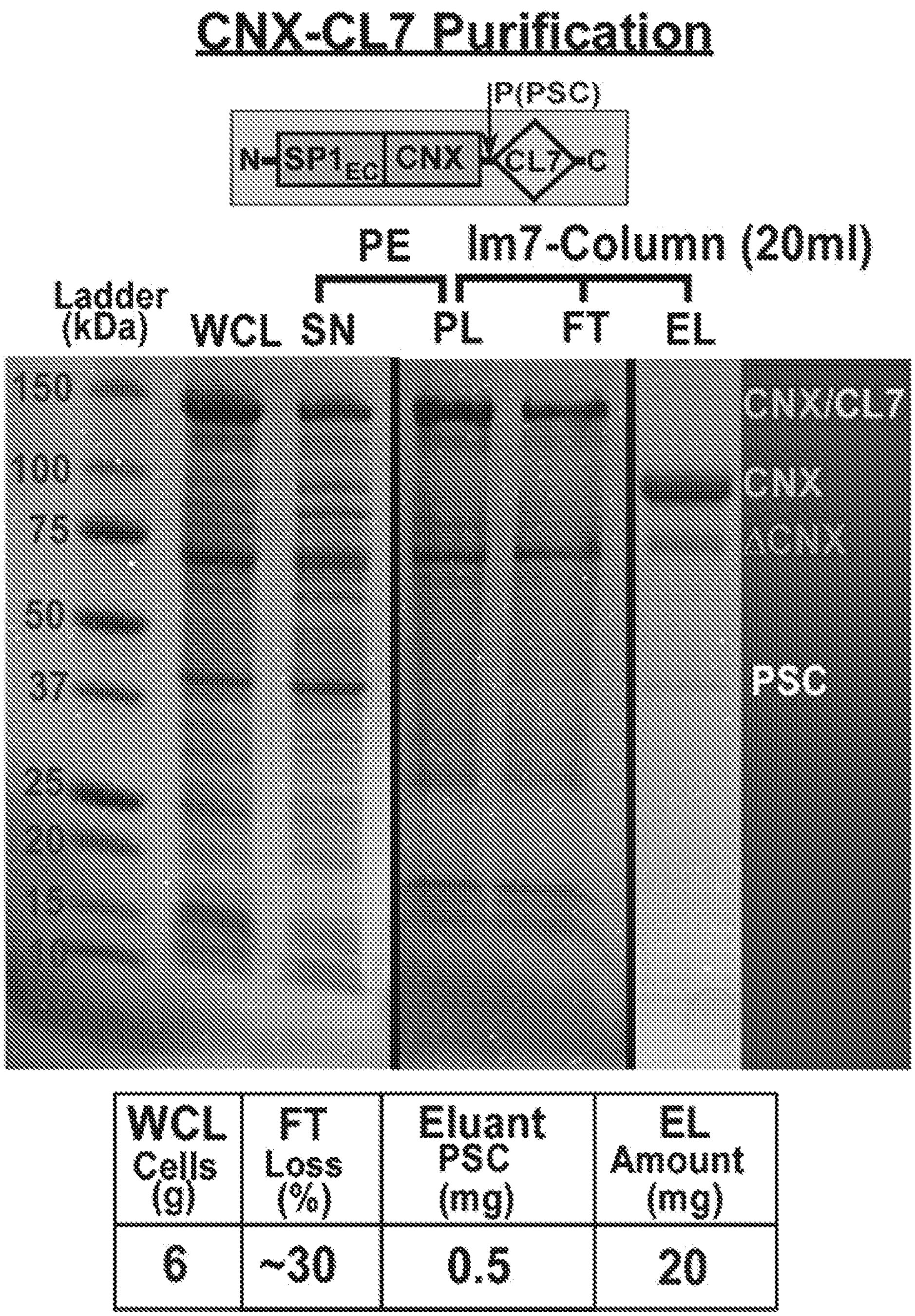
FIG. 11 shows the results of expression and a one-step (CL7/Im7) purification of human chaperone, calnexin (CNX). Abbreviations are as follows: PSC—prescission protease; P(PSC)—PSC cleavage sites; WCL—whole cell lysate; PE—polyethyleniimine; SN/PL—supernatant (SN) and washed (0.6M NaCl; 1.5% DDM); pellet after PE precipitation; FT—flow through; EL—eluate; ACNX—truncation of the CNX protein; $SP1_{EC}$—Yidc signal peptide with the adjusted for *E. coli* codons gene sequence, and containing the (C/S) mutation at the N-terminal position of a protein cleaved by signal peptidase.

The cells for both the Yidc and calnexin (CNX) proteins were grown as described above with a standard overexpression induction (0.1 mM IPTG). The 1 L cultures of the induced Yidc and CNX produced ~1 g cells. The lysates in the lysis buffers containing 0.35M/0.45M NaCl (for Yidc/CNX), 20 mM Tris pH 8.0, 5% glycerol, 0.1 mM PMSF, 1 inhibitory tablet) for ~3 g cells were subjected to polyethylenimine (PE) precipitation (FIG. 10*b*, right panel, and (FIG. 11) according to the following protocol. The PE was added to lysates in the three steps (0.02% PE at each) to a final concentration of 0.06%. At each step, the lysates were gently mixed for ~10 mins. After the final step, the suspension was centrifuged at 5,000 g for 15 mins. A larger amount of the CNX protein (FIG. 11) remaining in the soluble fraction after the PE precipitation than that of Yidc (FIG. 10*b*) likely accounts for a higher salt concentration in the CNX lysate (0.45M vs 0.35M NaCl). The PE pellets were then washed with the solution containing 0.6M NaCl, 20 mM Tris pH 8.0, 5% glycerol and 1.5% DDM. The supernatant (soluble fraction) was diluted 10 times with the DDM-free high salt loading buffer to yield 0.9M NaCl, 20 mM Tris pH 8.0, 5% glycerol and 0.15% DDM. This diluted supernatant was loaded on the 20 ml Im7-column (flow rate of ~1.5 ml/min; FIGS. 10*d* and 11). Upon loading, the column was subjected to washing with a few (2-3) alternate cycles of high/low (1M/0M NaCl) salt buffers containing 0.1% DDM. The proteins were then eluted using the small amounts (~0.25 mg) of PSC slowly (~0.2 ml/min.) loaded on the column in the elution buffer (0.5M NaCl, 20 mM Tris pH 8.0, 5% glycerol, 0.2 mM EDTA, 0.1% DDM). After elution the CL7-tag was washed out with 6M G-HCl and the column was reactivated through the standard gradient refolding procedure (see above).

Results

The (CL7/Im7) Chromatographic System

A family of colicins containing the DNAse domains (CL2, CL7, CL8, CL9) belong to a category of highly toxic enzymes. Their activity in host cells must be entirely suppressed, as this determines ultra-high affinity (4 to 7 orders of magnitude higher, for example, as compared to antibody/ligand complexes) to immunity proteins (Ims), the natural cognate inhibitors of the colicins. A number of other toxic enzymes are known and are characterized by similar ultra-high affinity to their inhibitors (for example, a group of colicins containing RNAse domains, eukaryotic DNAses, RNAses and proteases). All of them, therefore, can also be used as a basis for construction of ultra-high affinity columns. A major problem, however, is that the natural enzymes can be expressed only in the presence of their inhibitors. Their expression levels remain poor due to their toxicity, while their natural activities may affect purification of the target proteins. On the other hand, genetic inactivation of these enzymes is likely to result in substantial loss of affinity to their inhibitors, which in most cases target the enzymes' active sites. In this regard, the colicin DNAses (CLs) appear to be unique, since their cognate immunity proteins (Ims) bind remotely to the active/DNA-binding sites and sterically block DNA binding rather than activity of the enzymes. Using this unique feature of the (CL7/Im7) affinity pair and structural modeling, a CL7 variant, which entirely lacks catalytic and DNA binding activities (FIG. 7*a*) while retaining full binding affinity to its Im7 counterpart was constructed. CL7-tagged vectors were constructed. In these vectors, a target protein can be inserted either C-terminal (after the CL7 is fused to SUMO domain) or N-terminal to the CL7-tag, with the possibility for tag cleavage by the SUMO (SUMO-P) or precision (PSC) proteases, respectively (FIG. 7*b*). An expression vector for large scale purification of the Im7-construct (FIG. 7*c*) extended with the non-functional coiled-coil domain containing 4 Cys-residues was also designed. This Im7-construct was purified and covalently coupled to ~20 ml of iodo-acetyl agarose beads (Sulfo-Link, Thermo Fisher). The expressed CL7-tagged proteins can be efficiently loaded on (bound to) a column from a lysate and washed under a variety of conditions. The target proteins are eluted from the CL7-column upon protease (SUMO-P/PSC) cleavage. The column is then cleaned/re-activated through elution of the CL7 tag under denaturing (for example, 6M guanidine-hydrochloride; G-HCl) conditions followed by ~1 hr gradient refolding of Im7 (FIG. 7*b*). The Im7 column repeatedly allowed for large-scale purification (about 360-400 mg, nearly equimolar ratio) from the lysate of a model protein and possesses no non-specific binding (contaminations) to any of the untagged cellular components (FIG. 7*d*). The column restores ~100% capacity upon re-activation, as revealed by a nearly identical purification yield for this model protein after the Im7 column was used 100+ times.

For the majority of the commercially available chromatographic systems, performance is typically determined based on purification of a limited number of the well-known, small or mid-size, stable and easily purified proteins. The actual performance, therefore, may drop dramatically once applied to the complex, non-trivial biological molecules. To avoid this technological caveat, for the studies described herein, complex, biologically significant targets were chosen from the three major categories. These targets are most refractory to HHH-purification for different reasons. A first group include large, multi-subunit proteins, which are often difficult to overexpress and purify due to potential truncations, large interacting area and flexible and/or poorly folded domains that increase the probability of non-specific interactions with cellular proteins, thus resulting in contaminations. A second group includes nucleic acid binding proteins that exhibit non-specific, yet significant (cooperative) DNA/RNA-binding affinities that cause major impurities and affect the binding capacity of a column. The membrane proteins constitute a third group of targets, for which the purification process is usually quite tricky and exhausting. Their hydrophobic nature results in non-specific binding to each other as well as cytosolic cellular proteins upon lysis, thus requiring the presence of high concentrations of detergents during purification to avoid contaminations. This group of proteins is also characterized by typically low overexpression levels that additionally complicate purification due to a poor signal-to-noise ratio in the crude cell extracts.

Expression and Purification of DNA/RNA-Binding Bacterial Multi-Subunit RNA Polymerases With respect to purification, multi-subunit RNA polymerases (RNAPs) are most complex since they combine characteristics of large multi-subunit and DNA/RNA-binding proteins. Two bacterial RNAPs core enzymes from evolutionary distinct organisms, *T. thermophilus* (ttRNAP) and pathogenic *M. tuberculosis* (mtRNAP) were selected for the following reasons. First, these proteins are very big (MW 400 kDa) multi-subunit protein complexes of five subunits ($\alpha_2\beta\beta'\omega$). Stoichiometric expression is virtually impossible to achieve using the overexpression protocols in the *E. coli* host. The unbalanced expression creates the first line of complications for purification. Second, the largest β- and β'-subunits usually undergo transcription/translation-coupled truncations during overexpression. The resulting incomplete, loosely active RNAP molecules produce the second potential purification problem, which can only be resolved using affinity chromatography. Third, RNAPs contain at least four spatially distinct DNA-binding sites that are non-specific, but cooperatively bind strongly to cellular nucleic acids upon cell lysis. This results in major contamination by DNA/RNA and by DNA/RNA-binding proteins, respectively. In fact, after ~2 hours of lysate (with overexpressed RNAPs) incubation in a medium (~0.5M) salt buffer one can observe precipitation of the RNAP/DNA aggregates. These DNA/RNA-related impurities cannot be eliminated, for example, through a single His-Trap step, which is typically used for RNAP purification in the currently available overexpression systems, because His-Trap column itself possesses significant affinity to DNA (FIG. 6*a* and see below).

These impurities cannot be removed by any other single step chromatography, often requiring a time consuming, multi-step process that uses several columns, thus increasing time and effort. Also, this process often affects yield and activity of the final samples. Finally, multi-subunit RNAP is at the heart of transcription machinery, with high biological and medical significance. This protein has been extensively studied by various techniques, including high-resolution crystallographic analysis, for which HHH-purification is of central importance.

To establish an efficient protocol for the large-scale production and HHH-isolation of RNAPs, a multi-subunit, polycystronic expression vector following the two major criteria was designed. The vector can be used as a template for cloning of RNAPs from various species and presumably for other multi-subunit proteins, and enhance expression levels of the key (or each) individual subunits. A vector including ttRNAP was designed, since it was the most difficult target for overexpression in *E. coli*. Its nucleotide sequence is abundant of the *E. coli* rare codons and has exceedingly high G/C (~70%) content, which together could result in the overall poor expression level coupled with many translational truncations. To minimize these potential challenges, the gene sequences of the RNAP subunits were manually designed and synthesized. Rare codons were eliminated, while the GC-content was decreased to a reasonable level for *E. coli* (about 59%). To test the expression performance of the vector as well as to have a reference point in purification for comparison with the developed (CL7/Im7) system, only a His-tag at the C-terminus of the largest β'-subunit was introduced. The resulting vector (FIG. 8*a*; MV0) demonstrated clear, yet modest expression levels of the intact RNAP molecules (FIG. 8*b*). However, multiple attempts of His-trap purification under the different loading/washing conditions failed to provide a reasonably pure sample even though a preliminary heated sample (free from most of the *E. coli* proteins) was used (FIG. 8*c*).

The vector was then modified to relocate the His-tag to the second largest β-subunit and to replace it with the CL7-tag (cleavable by PSC protease) at the C-terminus of the β'-subunit. In addition, the short N-terminal (also cleavable by PSC protease) "expression" tags were introduced. These tags were designed to increase the expression levels of each of the co-expressed subunits (FIG. 8*a*; MV2). For this, slightly modified (to avoid hydrophobic residues) short N-terminal sequences of the three proteins, known to improve expression when fused to the N-termini of the target proteins (FIG. 8*a*; MV2), were used. Assuming that these short peptides improve expression levels through stabilization of translation initiation as well as the respective full length proteins, a major advantage of this approach is that all tags ("expression" and purification) might be removed in a single step, by the same protease. The N-terminal peptide impurities can then be eliminated through a simple dialysis step from a final sample. The expression of all RNAP subunits was substantially improved, with the β'-subunit showing the lowest expression level of (FIG. 8*b*), which allowed use of the Im7-column as a first and only purification step to obtain the large amount (~37 mg) of pure and intact RNAP sample (FIG. 8*c*). The activity tests using the synthetic elongation scaffold showed that the recombinant ttRNAP was as active as the one purified from the host thermophilic cells with ~95-97% of the active (elongating) complexes (FIG. 8*d*).

After establishing efficient expression and one-step HHH-purification protocols for ttRNAP, the identical expression (FIG. 8*a*; MV2) and purification approaches were used to obtain essentially the same results, i.e. the enhanced expression levels and the HHH-sample obtained in one-step purification through the Im7 column (FIG. 9*a*) for mtRNAP. The purified enzyme possessed high (~95%) activity in the elongation assay similar to, or better than that of commercial *E. coli* RNAP (FIG. 9*b*).

Notably, multiple purification trials with ttRNAP demonstrated that the best purity of ttRNAP, using both His-Trap and (CL7/Im7) approaches can be achieved if the lysates are first processed with DNAse and then loaded on the columns in high (1-1.2M) salt buffers. In particular, loading the lysates at a lower (0.5-0.8M) salt concentrations provided somewhat contaminated samples, even if the column was washed by the extra-high salt (2M) buffers after loading. Overall, these results showed that the HHH-samples of the big, multi-subunit DNA/RNA-binding proteins (RNAPs) can be obtained in one step and within only 5-6 hours. This demonstrates a dramatic improvement over the previously utilized approaches. For comparison, purification of untagged *T. thermophilus* RNAP from the host cells takes ~8-10 days, requires up to 5 different columns, with a final yield of only ~20 mg protein from ~6 g cells. Large scale purification of His-tagged RNAPs also requires several (2-3) days and a number of distinct purification steps, which affect the final yield and often results in loss of activity of the enzyme.

Expression and Purification of Membrane Proteins

Transmembrane proteins constitute up to 40% of a total protein pool in living cells. Most are of functional and clinical significance, yet only a few membrane proteins are well studied, much less studied at high-resolution. To a large extent, this deficit is related to challenges which occur at in the first, expression and/or purification steps of in vitro studies. The HHH-purification of membrane proteins required for crystallographic analysis is not trivial, mostly due to the unique hydrophobic nature and poor expression levels of the protein, even if an overexpression protocol is used. For these studies, two membrane proteins from different, prokaryotic and eukaryotic organisms, which also drastically differ in their configuration, size and function, were selected.

Bacterial Yidc membrane integrase (MW ~32 kDa) is an all-membrane protein that contains no bulky outer-membrane domains. Its structure has been determined. This protein served as a reference in purification trials, as all parameters of traditional (His-Trap) purification were already known. According to the published results, the Yidc purification required three chromatographic steps (His-Trap1→[TEV-protease cleavage of His-tag]→His-Trap2→Gel-Filtration) to yield ~1 mg pure protein from ~15-2 g cells in ~2-4 days. In particular, the first His-Trap step resulted in only ~60% purity protein as the membrane proteins are known to have substantial binding affinities to the $Ni^{2+}$-activated base (FIG. 10*a*). A poor final yield likely accounts not only for low overexpression levels that are typical for membrane proteins, but also for a loss of material during sequential purification steps.

In the studies described herein, a sequence of the Yidc gene was designed. This sequence was adjusted to *E. coli* codons and a vector was constructed with a PSC-cleavable CL7-tag fused at the C-terminus, as was done for the RNAPs (FIG. 10*b*). Surprisingly, this approach greatly improved the Yidc expression level as compared to published studies (FIG. 10*a*). Another surprise was that ultra-centrifugation, a traditional first step of the membrane proteins purification, which is always used to isolate the membrane fraction from the cytosolic proteins and nucleic acids, did not work at all. Not only was almost all of the overexpressed Yidc retained in a soluble fraction, but the pellet itself was very small and contained only a small amount of the cellular membrane proteins (FIG. 10*b*; left panel). The only explanation for this effect was that abundant overexpression of Yidc resulted in membrane fractionation upon lysis in the very small pieces, and the size/weight of the pieces did not allow them to precipitate, even under a huge, ultracentrifugal force. To check this possibility and to perform purification of Yidc under the standard, commonly used conditions, Yidc was expressed with no induction by IPTG since the vector that was used is characterized by promoter leaking. This approach solved the ultracentrifugation problem and allowed a high-purity Yidc sample to be obtained in one step using the Im7-column from the membrane fraction loaded on the column under high (0.9M) salt and detergent (dodecyl-maltopyranoside; DDM; 1.5%) concentrations. However, the amount of the purified sample was relatively modest (~14 mg protein from ~2 g cells), albeit much better than in the previously published work. Further, a small (~5-7%) but visible impurity was observed on a final gel (FIG. 10*c*). This impurity might have accounted for the covalent linking of the protein to the membrane components through the Cys residue, which becomes the N-terminal residue upon cleavage by a signal peptidase. In previous studies, others introduced the TEV protease cleavage site immediately after this Cys residue to remove it after the first step of purification. In the studies described herein, the Cys residue was mutated to Ser, which often occurs in this (cleavage) position in signal peptides and, thus, should not affect the activity of a signal peptidase.

Studies were conducted to improve the purification yield using the lysate of the induced cells in purification, for which ultracentrifugation step was skipped. First, the cell lysate was loaded directly on the Im7-column, in essentially the same conditions that were used for membrane fraction purification. This run, however, resulted in a contaminated sample, in which, a substantial trace of DNA was observed, suggesting that the protein might have significant affinity to nucleic acids. Following this hypothesis, its DNA-binding affinity was analyzed through polyethylenimine (PE) precipitation and fit was found that Yidc precipitates almost entirely with DNA in ~0.3-0.35 M salt (FIG. 10*b*; right panel). The following wash of the PE pellet in the higher-salt (0.6M) buffer containing 1.5% DDM fully released the Yidc protein in solution, while largely eliminating the nucleic acid component (FIG. 10*b*; right panel). Loading of the resulting supernatant on the Im7 column in high (~0.9M) salt provided a high purity sample, but in relatively low quantity (~4-5 mg from the 1 g cells). Most of it remained in the flow-through fraction. One possible reason for this might be in the high protein/DDM concentrations that cause a protein with micelles to form huge dynamic aggregates, both in solution and on a column to sterically block the Im7 active groups from the CL7-tag binding. To check this hypothesis, the lysate was diluted 10-fold with the detergent-free high (0.9M) salt buffer that greatly decreased both the protein and DDM concentrations. Though this approach increased purification time, it allowed for ~4-fold improvement in yield (~18 mg) from the same (4 g) amount of cells (FIG. 10*d*). The purified sample was also free of impurity observed in the protein with the wild-type signal peptide. At the same time, the size of the proteins (on a gel) were identical suggesting that the (C/S) mutation did not affect the signal peptide cleavage. Overall, these results provide a major improvement of Yidc purification over the previous, standard protocol (Kumakazi et al. "Crystallization and preliminary X-ray diffraction analysis of YidC, a membrane-protein chaperone and insertase from *Bacillus halodurans," Acta Crystallogr F Struct Biol Commun* 70: 1056-1060 (2014)).

A human calnexin (CNX) protein is a chaperone of substantially larger size (MW ~65 kDa) than Yidc, which contains a short (~35 residues long) transmembrane segment, and two soluble, outer membrane domains on both sides of the membrane. Markedly, full size CNX has never been overexpressed and purified in large quantities CNX likely forms a physiological complex with the HIV Nef protein in vivo. Therefore, this could be a promising target for anti-AIDS drug design. The detailed functional and structural studies of these interactions can be performed only in an in vitro model, for which HHH-purification of CNX is of central importance. To design the CNX overexpression vector, an identical purification approach was used. In particular, the natural CNX signal peptide was replaced with the mutated Yidc one, which could have accounted for improved expression levels of Yidc. Accordingly, the CNX expression level was high. The purification procedure, including the PE precipitation step, appeared to be very similar to that of Yidc and yielded ~20 mg of high purity protein (FIG. 11). The only minor contamination (~5-7%) observed in the purified CNX sample is not related to purification itself, but rather represents a truncated fragment of CNX. The binding activity of CNX to the Nef protein was further confirmed by the results of the surface plasmon resonance (SPR) and isothermal titration calorimetry (ITC) experiments. Notably, similar to that of RNAPs, loading of these membrane proteins on the Im7 column at high salt (about 0.9M) concentrations resulted in higher purity samples, since the lower salt concentrations produced contaminated proteins.

The protein purification systems provided herein allow high efficiency purification of proteins and large protein complexes from whole cell extracts using a single reusable chromatography column. The system employs a tag comprising a modified colicin DNAse domain that has extraordinary affinity for a colicin immunity protein. Genetic modifications eliminate the activities of the tag (colicin DNAse domain) except for its ability to bind, with high affinity to its receptor protein (colicin immunity protein). With the systems provided herein, it is possible to isolate cellular components with a level of purity that allows mass spectroscopy analysis of the contents. The immunity protein has been modified for efficient, covalent linkage to a broad range of solid supports, including, but not limited to, agarose beads and magnetic beads. Further, the tag (~20 kDa) can be introduced at a C- or N-terminus of a wide range of proteins including membrane proteins. The one column system also works with high yield expressing plasmids to yield significant levels of multiprotein complexes (MPCs), which, until the present invention, have been difficult to purify in significant quantities. In addition, cells can be genetically modified, for example, using the CRISPR system, to genetically fuse a nucleic acid encoding the tag directly to a nucleic acid encoding a target protein in eukaryotic cells. The systems provided herein can be used to isolate a variety of proteins and MPCs from a single tissue, tissue culture preparations or genetically modified cells. These studies also show that the ultra-high affinity (CL7/Im7) approach can facilitate studies of protein-protein interactions by surface plasmon resonance (SPR) spectroscopy, an essential technique for characterizing binding partners in physiological complexes and to validate results of foreseeable drug screening. The SPR approach requires one molecule to be immobilized on a sensor chip whereas solution with its binding partner is flowed over the sensor surface. One of the major problems with this technique is, in fact, practically identical to that of bioaffinity chromatography. Upon non-specific, chemical cross-linking to the sensor chip the biological units may lose most of their binding activities and this can significantly affect a signal-to-noise ratio, reproducibility and/or reliability of the SPR results. In the immobilization approach provided herein, a highly specific cross-linking protocol was used. This resulted in nearly 100% of the immobilized Im7 protein molecules retaining full binding activity to the CL7 counterparts. The (CL7/Im7) chromatography approach, thus, may be readily used for construction of reusable (in contrast to disposable chemical chips) Im7-activated SPR biosensors to which various C7-tagged targets can be immobilized under physiological conditions and with high-concentrations.

```
SEQUENCES
SEQ ID NO: 1-Wild-type CL7 DNAse domain
KRNKPGKATG KGKPVNNKWL NNAGKDLGSP VPDRIANKLR DKEFKSFDDF RKKFWEEVSK     60

DPELSKQFSR NNNDRMKVGK APKTRTQDVS GKRTSFELHH EKPISQNGGV YDMDNISVVT    120

PKRHIDIH

SEQ ID NO: 2-Wild-type CL2 DNAse domain
KRNKPGKATG KGKPVGDKWL DDAGKDSGAP IPDRIADKLR DKEFKNFDDF RKKFWEEVSK     60

DPDLSKQFKG SNKTNIQKGK APFARKKDQV GGRERFELHH DKPISQDGGV YDMNNIRVTT    120

PKRHIDIH

SEQ ID NO: 3-Wild-type CL8 DNAse domain
KRNKPGKATG KGKPVGDKWL DDAGKDSGAP IPDRIADKLR DKEFKNFDDF RRKFWEEVSK     60

DPELSKQFNP GNKKRLSQGL APRARNKDTV GGRRSFELHH DKPISQDGGV YDMDNLRITT    120

PKRHIDIH

SEQ ID NO: 4-Wild-type CL9 DNAse domain
KRNKPGKATG KGKPVGDKWL DDAGKDSGAP IPDRIADKLR DKEFKSFDDF RKAVWEEVSK     60

DPELSKNLNP SNKSSVSKGY SPFTPKNQQV GGRKVYELHH DKPISQGGEV YDMDNIRVTT    120

PKRHIDIH

SEQ ID NO: 5 (72 amino acid linker)
GGTSDGLEVL FQGPNGEDNQ SNHHHHHHHH NQAENSAANN ASDDGNQSSN ESSSDGEQAN     60

TDSAHEGGTA GS

SEQ ID NO: 6 modified CL7 plus linker
GGTSDGLEVLFQGPNGEDNQSNHHHHHHHHNQAENSAANNASDDGNQSSNESSSDGEQANTDSAHEGGTAGSKSN

EPGKATGEGKPVNNKWLNNAGKDLGSPVPDRIANKLRDKEFESFDDFRETFWEEVSKDPELSKQFSRNNNDRMKV

GKAPKTRTQDVSGKRTSFELNHQKPIEQNGGVYDMDNISVVTPKRNIDIEG

SEQ ID NO: 7 modified CL2 plus linker
GGTSDGLEVLFQGPNGEDNQSNHHHHHHHHNQAENSAANNASDDGNQSSNESSSDGEQANTDSAHEGGTAGSKSN

EPGKATGEGKPVGDKWLDDAGKDSGAPIPDRIADKLRDKEFENFDDFRETFWEEVSDPDLSKQFKGSNKTNIQKG

KAPFARKKDQVGGRERFELNHDKPIEQDGGVYDMNNIRVTTPKRNIDIN

SEQ ID NO: 8 modified CL8 plus linker
GGTSDGLEVLFQGPNGEDNQSNHHHHHHHHNQAENSAANNASDDGNQSSNESSSDGEQANTDSAHEGGTAGSKSN

EPGKATGEGKPVGDKWLDDAGKDSGAPIPDRIADKLRDKEFENFDDFRETFWEEVSKDPELSKQFNPGNKKRLSQ

GLAPRARNKDTVGGRRSFELNHDKPIEQDGGVYDMDNLRITTPKRNIDIN

SEQ ID NO: 9 modified CL9 plus linker
GGTSDGLEVLFQGPNGEDNQSNHHHHHHHHNQAENSAANNASDDGNQSSNESSSDGEQANTDSAHEGGTAGSEEE

RENNPGKATGEGKPVGDKWLDDAGKDSGAPIPDRIADKLRDKEFESFDDFREAVWEEVSKDPELSKNLNPSNKSS

VSKGYSPFTPKNQQVGGRKVYELNHDQPMWQGGEVYDMDNIRVTTPRRNIEIG

SEQ ID NO: 10 wildtype Im7
MELKNSISDYTEAEFVQLLKEIEKENVAATDDVLDVLLEHFVKITEHPDGTDLIYYPSDN

RDDSPEGIVKEIKEWRAANGKPGFKQG

SEQ ID NO: 11 wildtype Im9
MELKASISDYTEAEFLQLVTTICNADTSSEEELVKLVTHFEEMTEHPSGSDLIYYPKEGD

DDSPSGIVNTVQQWRAANGKSGFKQ

SEQ ID NO: 12 Im7 immobilization unit
MSDKIIHLTDDSFDTDVLKADGAILVDFWAEWCGPCKMIAPILDEIADEYQGKLIVAKLNIDQNPGTAPKYGIRG
```

-continued

IPTLLLFKNGEVAATKVGALSKGQLKEFLDANLAGDTSGTGAEGRRGEEAGKHHHHHHHHGKGAEEGRRGEAGLE

VLFQGPGQASGTTMGKIEEGKQETWNNGDKGYNGRAEDGGCGGAIEELEEEVRRHQMRLMALQLEEQLMGGCGDV

GDMEFRNSISDYTEEEFVRLLRGIERENVAATDDRLDWMLEHFVEITEHPDGIDLIYYPSDNRDDSPEGIVEEIR

EWREANGRPGFKQGGSTDGGDVGEERNRRCEELNEEIEEHRERLRQLEETREECRT

SEQ ID NO: 13: Im9 immobilization unit
MSDKIIHLTDDSFDTDVLKADGAILVDFWAEWCGPCKMIAPILDEIADEYQGKLTVAKLNIDQNPGTAPKYGIRG

IPTLLLFKNGEVAATKVGALSKGQLKEFLDANLAGDTSGTGAEGRRGEEAGKHHHHHHHHGKGAEEGRRGEAGLE

VLFQGPGQASGTTMGKIEEGKQETWNNGDKGYNGRAEDGGCGGAIEELEEEVRRHQMRLMALQLEEQLMGGCGDV

GDMEFRDSISDYTEEEFLRLVTSICNADTSSEEELVWMVTHFEEITEHPSGSDLIYYPREGD

DDSPSGIVNTVRQWREANGRSGFQQ GSTDGGDVGEERNRRCEELNEEIEEHRERLRQLEETREECRT

---

What is claimed is:

1. A polypeptide comprising a wild-type colicin-DNAse domain modified to comprise one or more mutations selected from the group consisting of a mutation that reduces DNAse activity, a mutation that decreases DNA binding and a mutation that increases thermostability of the polypeptide, wherein the one or more mutations comprise one or more mutations selected from the group consisting of R2S, K4E, K11E, K45E, K51E, K52T, H99N, S105E, H124N and H128E mutation in SEQ ID NO: 1.

2. The polypeptide of claim 1, wherein the mutations comprise R2S, K4E, K11E, K45E, K51E, K52T, H99N, S105E, H124N and H128E mutation in SEQ ID NO: 1.

3. The polypeptide of 1, wherein the polypeptide further comprises a cleavable polypeptide sequence in operable linkage with the colicin-DNAse domain, wherein the cleavable polypeptide sequence is at least about fifty amino acids in length.

4. The polypeptide of claim 3, wherein the polypeptide comprises SEQ ID NO: 6, SEQ ID NO: 7, SEQ ID NO: 8 or SEQ ID NO: 9.

5. The polypeptide of claim 3, further comprising a heterologous protein operably linked to the cleavable polypeptide sequence, wherein the cleavable polypeptide sequence links the heterologous polypeptide with the colicin-DNAse domain.

6. A nucleic acid encoding the polypeptide of claim 1.

7. A vector comprising the nucleic acid of claim 6.

8. A cell comprising the vector of claim 7.

9. A method of purifying a heterologous protein comprising:

a) transfecting in a cell culture medium a cell with a vector, wherein the vector comprises a nucleic acid encoding a first polypeptide under conditions in which the first polypeptide is expressed, wherein the first polypeptide is the polypeptide of claim 5;

b) harvesting the cell culture medium comprising the expressed first polypeptide;

c) lysing the cells to obtain a supernatant comprising the expressed first polypeptide;

d) contacting the supernatant with an affinity matrix comprising a substrate and a second polypeptide, wherein the second polypeptide comprises a colicin immunity protein with one or more mutations, e) washing the matrix to remove biological molecules non-specifically bound to the first expressed polypeptide and the matrix;

f)) eluting the heterologous protein from the matrix, comprising enzymatically cleaving the heterologous protein from the first polypeptide.

10. A method of purifying a heterologous protein comprising:

a) transfecting in cell culture medium a cell with a vector comprising a nucleic acid encoding a first polypeptide, wherein the first polypeptide comprises the polypeptide of claim 5 under conditions in which the first polypeptide comprising the heterologous protein is expressed;

b) harvesting the cell culture medium comprising the expressed first polypeptide comprising a heterologous protein;

c) contacting the harvested cell culture medium with an affinity matrix, wherein the affinity matrix comprises a substrate and a second polypeptide comprising a colicin immunity protein with one or more mutations;

d) washing the matrix to remove biological molecules non-specifically bound to the expressed first polypeptide comprising a heterologous protein and the matrix;

e) eluting the heterologous protein from the matrix, comprising enzymatically cleaving the heterologous protein from the first polypeptide.

11. A method of genetically modifying the genome of a cell to encode a chimeric polypeptide comprising a protein of interest and a modified colicin DNAse domain comprising:

A) introducing into a population of cells (i) a guide RNA (gRNA) comprising a first nucleotide sequence that hybridizes to a target DNA in the genome of the cell, wherein the target DNA is the coding sequence or a nucleic acid sequence adjacent to the N-terminus or the C-terminus of the coding sequence for the protein of interest, and a second nucleotide sequence that interacts with a site-directed nuclease;

(ii) a recombinant site-directed nuclease, wherein the site-directed nuclease comprises an RNA-binding portion that interacts with the second nucleotide sequence of the gRNA, wherein the site-directed nuclease specifically binds and cleaves the target DNA to create a double-stranded break before the N-terminus or after the C-terminus of the coding sequence for the protein; and (iii) a donor nucleic acid sequence comprising (a) a third nucleotide sequence that encodes the polypeptide of any of claim 3 and (b) a fourth nucleotide sequence that hybridizes to a genomic sequence flanking the double stranded break in the target DNA, wherein (A)(i), (A)(ii) and (A)(iii) are introduced into the cells under conditions that allow homology-directed repair and integration of the third nucleotide sequence into the target DNA to form a genetically modified cell.

* * * * *

UNITED STATES PATENT AND TRADEMARK OFFICE

CERTIFICATE OF CORRECTION

PATENT NO. : 10,759,830 B2
APPLICATION NO. : 16/060753
DATED : September 1, 2020
INVENTOR(S) : Dmitry Vassylyev et al.

It is certified that error appears in the above-identified patent and that said Letters Patent is hereby corrected as shown below:

In the Claims

Line 26, Claim 3, please insert the word --claim-- before the number 1.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*